US011478470B2

(12) United States Patent
Yang et al.

(10) Patent No.: US 11,478,470 B2
(45) Date of Patent: Oct. 25, 2022

(54) COMBINATION PRODUCT OF BCL-2 INHIBITOR OR BCL-2/BCL-XL DUAL INHIBITOR AND BTK INHIBITOR AND USE THEREOF IN THE PREVENTION AND/OR TREATMENT OF DISEASES

(71) Applicant: ASCENTAGE PHARMA (SUZHOU) CO., LTD., Suzhou (CN)

(72) Inventors: Dajun Yang, Suzhou (CN); Yifan Zhai, Suzhou (CN); Douglas Dong Fang, Suzhou (CN); Guangfeng Wang, Suzhou (CN); Guoqin Zhai, Suzhou (CN)

(73) Assignee: ASCENTAGE PHARMA (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 16/648,603

(22) PCT Filed: Jul. 30, 2019

(86) PCT No.: PCT/CN2019/098252
§ 371 (c)(1),
(2) Date: Mar. 18, 2020

(87) PCT Pub. No.: WO2020/024916
PCT Pub. Date: Feb. 6, 2020

(65) Prior Publication Data
US 2020/0222393 A1 Jul. 16, 2020

(30) Foreign Application Priority Data
Jul. 31, 2018 (CN) .......................... 201810867251.8

(51) Int. Cl.
| A61K 31/496 | (2006.01) |
| A61P 35/00 | (2006.01) |
| A61K 31/519 | (2006.01) |
| A61K 45/06 | (2006.01) |

(52) U.S. Cl.
CPC .......... *A61K 31/496* (2013.01); *A61K 31/519* (2013.01); *A61K 45/06* (2013.01); *A61P 35/00* (2018.01)

(58) Field of Classification Search
CPC .. A61K 31/496; A61K 31/519; A61K 31/635; A61K 31/662; A61P 29/00; A61P 35/00; A61P 37/06
See application file for complete search history.

(56) References Cited

U.S. PATENT DOCUMENTS

| 8,546,399 B2 | 10/2013 | Bruncko et al. |
| 10,213,433 B2 | 2/2019 | Catron et al. |
| 10,221,174 B2 | 3/2019 | Wang et al. |
| 2010/0305122 A1 | 12/2010 | Bruncko et al. |
| 2011/0124628 A1 | 5/2011 | Bruncko et al. |
| 2012/0028925 A1 | 2/2012 | Tao et al. |
| 2012/0157470 A1 | 6/2012 | Catron et al. |
| 2015/0329541 A1 | 11/2015 | Bruncko et al. |

FOREIGN PATENT DOCUMENTS

| CN | 101918420 A | 12/2010 |
| CN | 103402521 B | 1/2016 |
| CN | 105246882 A | 1/2016 |
| CN | 105061315 B | 10/2017 |
| CN | 106794171 B | 3/2020 |
| JP | 2013526612 A | 6/2013 |
| JP | 2013540823 A | 11/2013 |
| JP | 2013543894 A | 12/2013 |
| WO | WO 2005/049593 A2 | 6/2005 |
| WO | WO 2008/030836 A2 | 3/2008 |
| WO | WO 2008/070663 A2 | 6/2008 |
| WO | WO 2010/065824 A2 | 6/2010 |
| WO | WO 2010/065865 A2 | 6/2010 |
| WO | WO 2010/093742 A1 | 8/2010 |
| WO | WO 2010/138588 A2 | 12/2010 |
| WO | WO 2011/068863 A1 | 6/2011 |
| WO | WO 2011/149492 A1 | 12/2011 |
| WO | WO 2012/058392 A1 | 5/2012 |
| WO | WO 2012/071374 A1 | 5/2012 |
| WO | WO 2012/103059 A2 | 8/2012 |
| WO | WO 2014/113413 A1 | 7/2014 |
| WO | WO 2015/130585 A1 | 9/2015 |
| WO | WO 2015/161032 A1 | 10/2015 |
| WO | WO 2016/024230 A1 | 2/2016 |
| WO | WO 2017/037579 A1 | 3/2017 |
| WO | WO 2018/027097 A1 | 2/2018 |
| WO | WO 2020/024820 A1 | 2/2020 |
| WO | WO 2020/024826 A1 | 2/2020 |
| WO | WO 2020/024834 A1 | 2/2020 |
| WO | WO 2020/024916 A1 | 2/2020 |

(Continued)

OTHER PUBLICATIONS

Barf et. al., The J. Pharm. & Exp. Ther., vol. 363, pp. 240-252, publ. Nov. 2017 (Year: 2017).*
Ackler et al., "The Bcl-2 inhibitor ABT-263 enhances the response of multiple chemotherapeutic regimens in hematologic tumors in vivo." *Cancer Chemotherapy and Pharmacology.*, vol. 66, No. 5, (Jan. 2010), pp. 869-880.
Adams et al., "The Bcl-2 apoptotic switch in cancer development and therapy," *Oncogene*, 26(9), pp. 1324-1337, (2007).
Adams et al., "The Bcl-2 protein family: arbiters of cell survival," *Science*, 281 (5381), pp. 1322-1326, (1998).

(Continued)

*Primary Examiner* — Sarah Pihonak
(74) *Attorney, Agent, or Firm* — Barnes & Thornburg LLP

(57) ABSTRACT

Provided herein is a combination product comprising a Bcl-2 inhibitor (or a Bcl-2/Bcl-xl dual inhibitor) and a BTK inhibitor, the combination product providing a use in the prevention and/or treatment of a disease (e.g., cancer, autoimmune disease and inflammatory disease.).

11 Claims, 9 Drawing Sheets

(56) References Cited

FOREIGN PATENT DOCUMENTS

WO    WO 2020/103921 A1    5/2020

OTHER PUBLICATIONS

Aguilar et al., "Discovery of 4-((3'R,4'S,5'R)-6"-Chloro-4'-(3-chloro-2-fluorophenyl)-1'-ethyl-2"-oxodispiro[cyclohexane-1,2'-pyrrolidine-3',3"-indoline]-5'-carboxamido)bicycle[2,2,2]octane-1-carboxylic Acid (AA-115/APG-115): A Potent and Orally Active Murine Double Minute 2 (MDM2) Inhibitor in Clinical Development," *J. Med. Chem.* 2017, 60, pp. 2819-2839.

Amundson et al., "An informatics approach identifying markers of chemosensitivity in human cancer cell lines," *Cancer Res.*, 60(21), pp. 6101-6110, (2000).

Bai L., et al., "BM-1197: A Novel and Specific Bcl-2/Bcl-xL Inhibitor Inducing Complete and Long-Lasting Tumor Regression In Vivo," *PloS ONE*, vol. 9, No. 6, (Jun. 2014), pp. 399404-e99404.

Bingham et al., "Over one hundred solvates of sulfathiazole," *Chem. Commun.*, pp. 603-604, (2001).

Bogenberger et al., "Combined venetoclax and alvocidib in acute myeloid leukemia," *Oncotarget.*, vol. 8, No. 63, (Nov. 2017), pp. 107206-107222.

Caira et al., "Preparation and crystal characterization of a polymorph, a monohydrate, and an ethyl acetate solvate of the antifungal fluconazole," *J. Pharm. Sci.*, 93(3), pp. 601-611, (2004).

Cang et al., "ABT-199 (venetoclax) and BCL-2 inhibitors in clinical development," *J. Hematol. Oncol.*, 8, pp. 129, (2015).

Chen et al., "The Bcl-2/Bcl-X-L/Bcl-w Inhibitor, Navitoclax, Enhances the Activity of Chemotherapeutic Agents In Vitro and In Vivo," *Molecular Cancer Therapeutics.*, vol. 11, No. 12, (Sep. 2011), pp. 2340-2349.

Danial et al., "Cell death: critical control points," *Cell*, 116(2), pp. 205-219, (2004).

Dey et al., "Voruciclib, a clinical stage oral CDK9 inhibitor, represses MCL-1 and sensitizes high-risk Diffuse Large B-cell Lymphoma to BCL2 inhibition," *Scientific Reports* 7:18007, pp. 1-11, (2017).

Dorwald F.A., "Side Reactions in Organic Synthesis," *Wiley: VCH, Weinheim*, pp. IX of Preface pp. 1-15, (2005).

Huang, "Fluorescence polarization competition assay: the range of resolvable inhibitor potency is limited by the affinity of the fluorescent ligand," *J. Biomol. Screen.*, 8(1), pp. 34-38, (2003).

Inoue-Yamauchi, Akane et al., "Targeting the differential addiction to anti-apoptotic bcl-2 family for cancer therapy," *Nature Communications*, vol. 8, (Jul. 2017), pp. 1-14.

International Search Report and Written Opinion for PCT/CN2019/096968, dated Oct. 22, 2019.

International Search Report and Written Opinion for PCT/CN2019/097028, dated Oct. 22, 2019.

International Search Report and Written Opinion for PCT/CN2019/097081, dated Oct. 29, 2019.

International Search Report and Written Opinion for PCT/CN2019/098252, dated Nov. 4, 2019.

International Search Report and Written Opinion for PCT/CN2019/120144, dated Feb. 24, 2020.

International Search Report for PCT/US2017/045428, dated Nov. 17, 2017.

Kirkin et al., "The role of Bcl-2 family members in tumorigenesis," *Biochem. Biophys. Acta.*, 1644(2-3), pp. 229-249, (2004).

Kojima et al., "Concomitant Inhibition of MDM2 and Bcl-2 Protein Function Synergistically Induce Mitochondrial Apoptosis in AML," *Cell Cycle*, vol. 5, Iss. 23, pp. 2778-2786, (Dec. 2006).

Lehmann, Christian et al, "Superior anti-tumor activity of the MDM2 antagonist idasanutlin and the Bcl-2 inhibitor venetoclax in p53 wild-type acute myeloid leukemia models," Journal of Hematology & Oncology, (2016), 9:50; pp. 1-13.

Metro, G. and Cappuzzo, Federico, "Emerging drugs for small-cell lung cancer," *Expert Opin. Emerging Drugs*, 14(4), pp. 591-606, (2009).

Moss, "Basic terminology of stereochemistry," *Pure & Appl. Chem.*, 68(12), pp. 2193-2222, (1996).

Nakayama et al., "Targeted disruption of Bcl-2 alpha beta in mice: occurrence of gray hair, polycystic kidney disease, and lymphocytopenia," *Proc. Natl. Acad. Sci. USA*, 91(9), pp. 3700-3704, (1994).

Nikolovska-Coleska et al., "Development and optimization of a binding assay for the XIAP BIR3 domain using fluorescence polarization," *Anal. Biochem.*, 332(2), pp. 261-273, (2004).

Pan et al., "Activation of p56 By Novel MDM2 Antagonist RG7388 Overcomes AML Inherent and Acquired Resistance to Bcl-2 Inhibitor ABT-199 (GDC-0199)," *Blood*, 124:2162; (2014).

Portell et al., "Abstract B40: Synergistic cytotoxicity of ibrutinib and the BCL2 antagonist ABT-199 in mantle cell lymphoma and chronic lymphocytic leukemia: Molecular analysis reveals mechanisms of target interactions," *Hematologic Malignancies*, vol. 21, Issue 17, (Sep. 2015).

Reed et al., "BCL-2 family proteins: regulators of cell death involved in the pathogenesis of cancer and resistance to therapy," *J. Cell Biochem.*, 60(1), pp. 23-32, (1996).

Reed, "Bcl-2 family proteins: strategies for overcoming chemoresistance in cancer," *Adv. Pharmacol.*, 41, pp. 501-532, (1997).

Seymour et al., "Venetoclax plus rituximab in relapsed or refractory chronic lymphocytic leukaemia: a phase 1b study," *Lancet Onco.* (Feb. 2017) 18(2), pp. 230-240.

Souers et al., "ABT-199, a potent and selective BCL-2 inhibitor, achieves antitumor activity while sparing platelets," *Nat. Med.*, 19(2), pp. 202-208, (2013).

Tse et al., "ABT-263: a potent and orally bioavailable Bcl-2 family inhibitor," *Cancer Res.*, 68(9), pp. 3421-3428, (2008).

van Delft et al., "The BH3mimetic ABT-737 targets selective Bcl-2 proteins and efficiently induces apoptosis vai Bak/Bax if Mcl-1 is neutralized," *Cancer Cell*, 10(5), pp. 389-399, (2006).

Van Goethem et al., "Dual targeting of MDM2 and BCL2 as a therapeutic strategy in neuroblastoma," *Oncotarget*, vol. 8, No. 34, (2017), pp. 57047-57057.

van Tonder et al., "Preparation and physicochemical characterization of 5 niclosamide solvates and 1 hemisolvate," *AAPS PharmSciTech.*, 5(1), E12, (2004).

Venclexta, Venclexta tablets label, Translation (Dec. 14, 2017).

Venkatesh, J., "Role of the Development Scientist in Compound Lead Selection and Optimizatin" *J. Pharm. Sci.*, vol. 89, No. 2, pp. 145-154, (2000).

Willis et al., "Apoptosis initiated when BH3 ligands engage multiple Bcl-2 homologs, not Bax or Bak," *Science*, 315(5813), pp. 856-859, (2007).

Written Opinion of the International Searching Authority for PCT/US2017/045428, dated Nov. 17, 2017.

Zelenetz et al., "Results of a Phase 1b Study of Venetoclax Plus R-or G-CHOP in Patients with B-Cell Non-Hodgkin Lymphoma," *Blood*, (Dec. 2016), vol. 128(22), pp. 3032-3035.

Zhang, "Apoptosis-based anticancer drugs," *Nat. Rev. Drug Discov.*, 1(2), pp. 101-102, (2002).

Zinzani et al., "Phase 2 Study of Venetoclax Plus Rituximab or Randomized Ven Plus Bendamustine+Rituximab (BR) Versus BR in Patients ith Relapsed/Refractory Follicular Lymphoma: Interim Data," *Blood*, (Dec. 2016), vol. 128(22), pp. 617-620.

\* cited by examiner

A.

B.

A.

B.

A.

B.

| | DOHH2$^{R\text{-ibrutinib}}$ Compound 6 | DOHH2$^{R\text{-ibrutinib}}$ ABT-199 | DOHH2 Compound 6 | DOHH2 ABT-199 |
|---|---|---|---|---|
| IC$_{50}$(μM) | 0.648 | 1.189 | 0.04837 | 0.0511 |

| | DOHH2$^{R\text{-ibrutinib}}$ Compound 88 | DOHH2 Compound 88 |
|---|---|---|
| IC$_{50}$(μM) | 0.01707 | 0.4284 |

COMBINATION PRODUCT OF BCL-2 INHIBITOR OR BCL-2/BCL-XL DUAL INHIBITOR AND BTK INHIBITOR AND USE THEREOF IN THE PREVENTION AND/OR TREATMENT OF DISEASES

CROSS-REFERENCE TO RELATED APPLICATIONS

This application is a national phase application of PCT/CN2019/098252, filed Jul. 30, 2019, which application claims the benefit of and priority to Chinese Patent Application No. 201810867251.8, filed Jul. 31, 2018, the entire contents of each of which are incorporated by reference herein.

TECHNICAL FIELD

The invention belongs to the technical field of medicine, and particularly relates to a combined product comprising a Bcl-2 inhibitor or a Bcl-2/Bcl-xL dual inhibitor and a BTK inhibitor and a use thereof in the prevention and/or treatment of a disease (for example, cancers, autoimmune diseases and inflammatory diseases).

BACKGROUND ART

Apoptosis (programmed cell death) is a natural pathway for the body to clear abnormal or unwanted cells, which can cause various diseases such as cancer if affected.

Anti-apoptotic Bcl-2 proteins are associated with many diseases. Bcl-2 family proteins are key regulators in the mitochondria-mediated apoptotic pathway. Escape from apoptosis is one of the characteristics of human cancer and is a common cause of clinical drug resistance.

Bruton's tyrosine kinase (BTK) belongs to the members of Tec family. It consists of a unique N-terminal domain, i.e., PH (pleckstrin homology) domain, a TH (Tec homology) homology domain, a SH3 (Src homology 3) domain, a SH2 (Src homology 2) domain, and a catalytic domain, also called SH 1/TK (Src homology 1/Tyrosine kinase) domain or kinase domain (Akinley et al: Ibrutinib and novel BTK inhibitors in clinical development, Journal of Hematology & Oncology 2013, 6:59). During the normal development of B lymphocytes, the correct expression of different protein regions of BTK gene plays a key role in the function of B cells and various transduction pathways.

There are a variety of receptors at BTK function downstream, including growth factor, B cell antigen, chemokine, and innate immune receptor, which initiate a diverse range of cellular processes such as cell proliferation, survival, differentiation, movement, angiogenesis, cytokine production, antigen expression, and the like. Therefore, BTK plays an important role in many hematopoietic signaling pathways, and is also important in B cell activation, development, survival, and signaling (Kurosaki, Molecular mechanisms in B cell antigen receptor signaling. Curr OP Imm, 1997, 9 (3): 309-18).

Evidence for the role of BTK in autoimmune diseases has been provided by tests of BTK-deficient mice and BTK-sufficient mice model (Kil L P, et al: Bruton's tyrosine kinase mediated signaling enhances leukemogenesis in a mouse model for chronic lymphocytic Leukemia. Am J Blood Res 2013, 3(1): 71-83). In a mouse model of chronic lymphocytic leukemia (CLL), the BTK-deficient mice completely abolish chronic lymphocytic leukemia, and the overexpression of BTK accelerates the onset of leukemia and increases mortality.

With the advancement of molecular biology, molecular targeting therapy has become a hotspot in medical researches (especially tumor research). The biological behavior of most tumors is not dominated by a single signaling pathway, but multiple signaling pathways. Thus, there is a need in the art for protocols and products for the combination of different target proteins and/or different signaling pathways that are capable of reducing the dose of single drug, reducing single drug side effects and/or acting in a synergistic manner for the purpose of preventing and/or treating diseases.

CONTENTS OF THE INVENTION

In order to meet the needs in the prior art, the present invention provides a combination product comprising a Bcl-2 inhibitor or a Bcl-2/Bcl-xL dual inhibitor and a BTK inhibitor and its use in the treatment and/or prevention of a disease (for example, cancer, autoimmune disease and inflammatory disease).

In particular, a first aspect of the invention relates to a combination product comprising a Bcl-2 inhibitor or a Bcl-2/Bcl-xL dual inhibitor and a BTK inhibitor.

In particular, another aspect of the invention relates to a method of treating a disease (e.g., cancer, autoimmune disease, and inflammatory disease) in a subject in need thereof, comprising administering a therapeutically effective amount of a Bcl-2 inhibitor or a Bcl-2/Bcl-xL dual inhibitor to the subject, wherein the subject is refractory or is resistant to a BTK inhibitor. In certain embodiments, the subject is refractory or is resistant to ibrutinib.

In some embodiments, the Bcl-2 inhibitor is a compound of Formula I-A, or a pharmaceutically acceptable salt thereof:

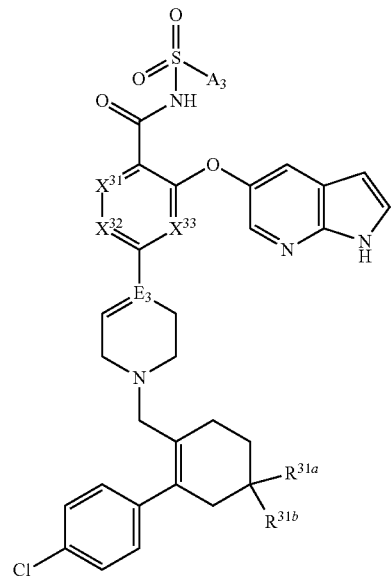

I-A wherein:
A3 is

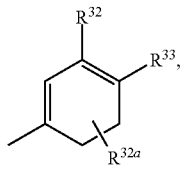
A-1

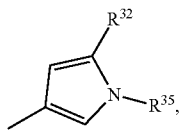
A-2

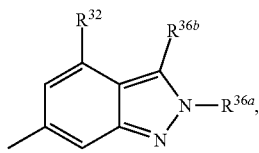
A-3

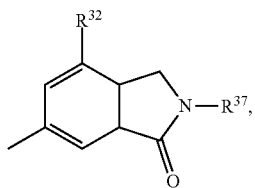
A-4

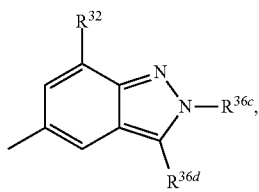
A-5

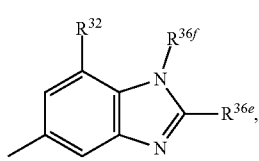
A-6

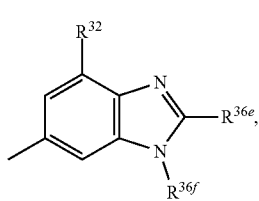
A-7

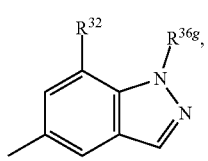
A-8

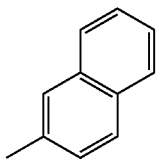
A-9 and

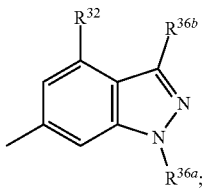
A-10

E3 is a carbon atom and ═ is a double bond; or

E3 is a —C(H)— and ═ is a single bond; or

E3 is a nitrogen atom and ═ is a single bond;

X31, X32 and X33 are each independently selected from the group consisting of —CR38═ and —N═;

R31a and R31b taken together with the carbon atom to which they are attached form a 3-, 4-, or 5-membered optionally substituted aliphatic ring;

R31a and R31b taken together with the carbon atom to which they are attached form a 4- or 5-membered optionally substituted heterocyclo;

R32 is selected from the group consisting of —NO2, —SO2CH3, and —SO2CF3,

R32a is selected from the group consisting of hydrogen and X;

R33 is selected from the group consisting of hydrogen, —CN, —C≡CH, and —N(R34a)(R34b);

R34a is selected from the group consisting of optionally substituted C1-6 alkyl, optionally substituted $C_3$-6 cycloalkyl, heterocyclo, heteroalkyl, cycloalkylalkyl, and heterocycloalkyl;

R34b is selected from the group consisting of hydrogen and C1-4 alkyl;

R35 is selected from the group consisting of optionally substituted C1-6 alkyl, heterocyclo, cycloalkylalkyl, and heterocycloalkyl;

R36a, R36c, R36e, R36f, and R36g are each independently selected from the group consisting of hydrogen, optionally substituted C1-6 alkyl, optionally substituted $C_3$-6 cycloalkyl, optionally substituted aryl, optionally substituted heteroaryl, heterocyclo, heteroalkyl, cycloalkylalkyl, and heterocycloalkyl;

R36b and R36d are each independently selected from the group consisting of hydrogen, C1-4 alkyl, and halogen;

R37 is selected from the group consisting of optionally substituted $C_1$-6 alkyl, heterocyclo, heteroalkyl, cycloalkylalkyl, and heterocycloalkyl;

R38 is selected from the group consisting of hydrogen and halogen.

In some embodiments, the Bcl-2 inhibitor is selected from the group consisting of a compound or a pharmaceutically acceptable salt or solvate thereof:

5
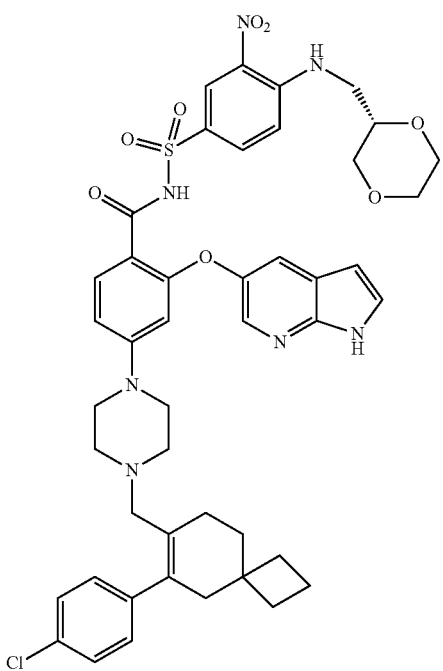
,
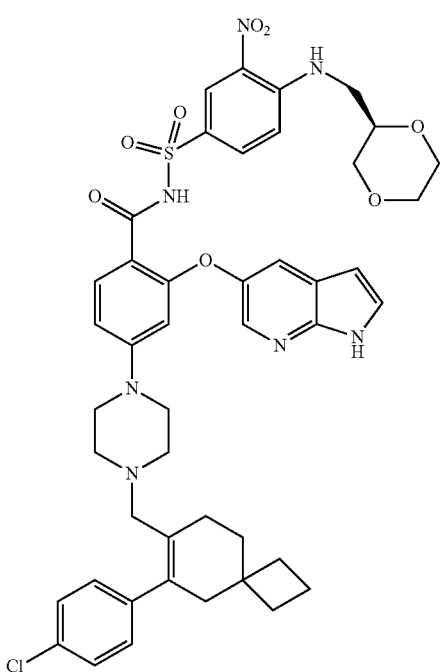
or
6
-continued
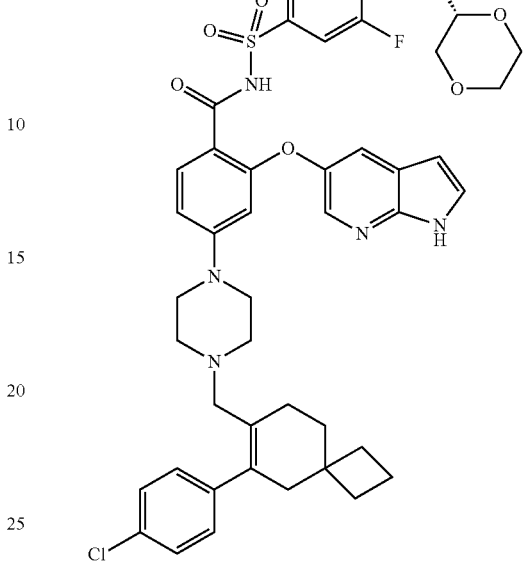
.
In some embodiments, the Bcl-2 inhibitor is the following compound or a pharmaceutically acceptable salt or solvate thereof:
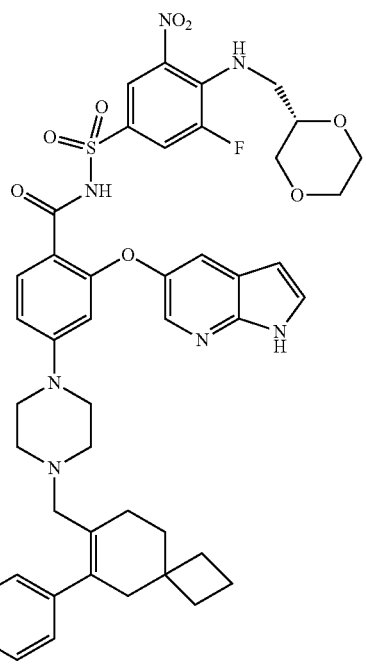
.
In some embodiments, the Bcl-2/Bcl-xL dual inhibitor is a compound of formula (I), (II), (III) or (IV), or a pharmaceutically acceptable salt or solvate thereof:

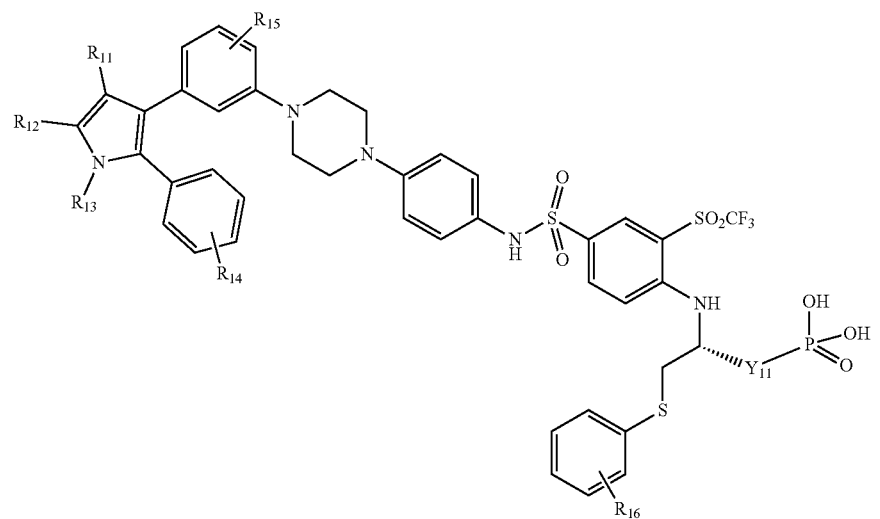
(I)
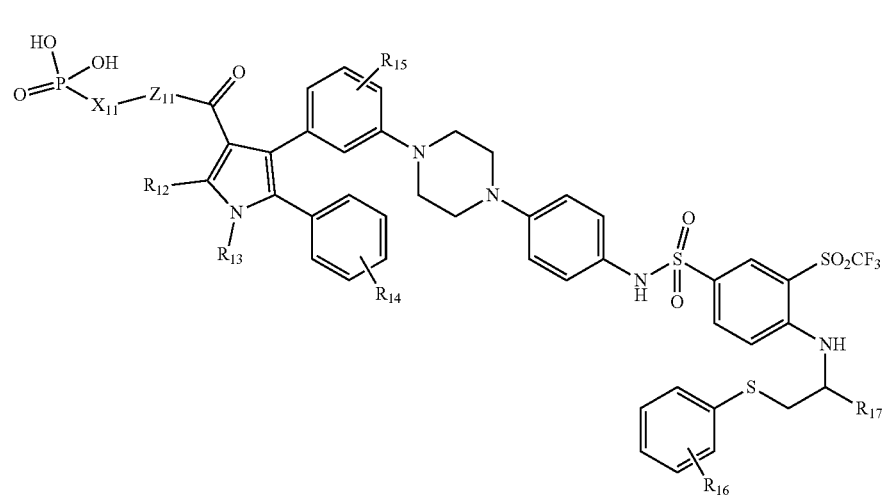
(II)
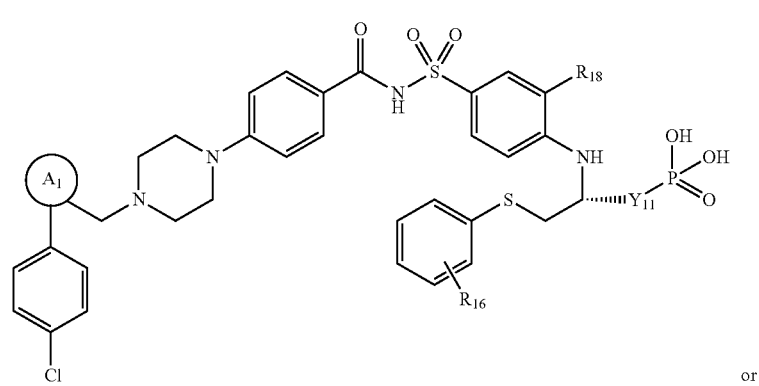
(III)
or

-continued

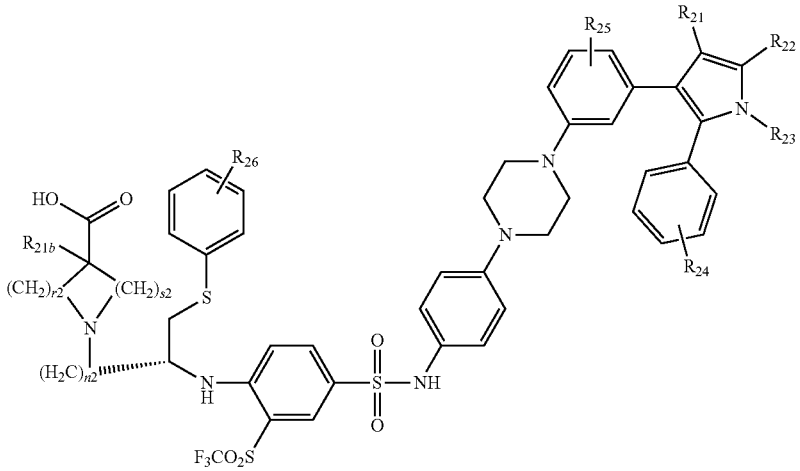
(IV)

wherein:
A₁ ring is

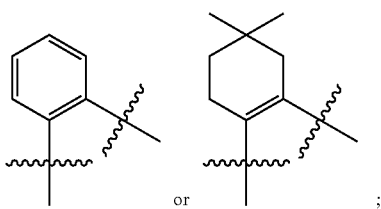

X11, substituted or unsubstituted, is selected from the group consisting of alkylene, alkenylene, cycloalkylene, cycloalkenylene and heterocycloalkylene;
Y11 is selected from the group consisting of (CH2)n-N(R11a)2 and

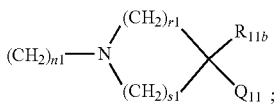

Q11 is selected from the group consisting of O, O(CH2)1-3, NR11c, NR11c(C1-3 alkylene), OC(=O)(C1-3 alkylene), C(=O)O, C(=O)O(C1-3 alkylene), NHC(=O)(C1-3 alkylene), C(=O)NH, and C(=O)NH(C1-3 alkylene);
Z11 is O or NR11c,
R11 and R12, independently, are selected from the group consisting of H, CN, NO2, halo, alkyl, cycloalkyl, alkenyl, cycloalkenyl, alkynyl, aryl, heteroaryl, heterocycloalkyl, OR1', SR1', NR1'R1", COR1', CO2R1', OCOR1', CONR1R1", CONR1'SO2R1', NR1'COR1", NR1'CONR1"R1'", NR1'C=SNR1"R1'", NR1'SO2R1", SO2R1', and SO2NR1'R1",
R13 is selected from the group consisting of H, alkyl, cycloalkyl, alkenyl, cycloalkenyl, alkynyl, aryl, heteroaryl, heterocycloalkyl, OR1', NR1R1", OCOR1', CO2R1', COR1', CONR1R1", CONR1'SO2R1", C1-3 alkyleneCH(OH)CH2OH, SO2R1', and SO2NR1'R1",
R1', R1", and R1'", independently are H, alkyl, cycloalkyl, alkenyl, cycloalkenyl, alkynyl, aryl, heteroaryl, C1-3 alkyleneheterocycloalkyl, or heterocycloalkyl;

R1' and R1", or R1" and R1'", can be taken together with the atom to which they are bound to form a 3 to 7-membered ring;
R14 is hydrogen, halo, C1-3 alkyl, CF3, or ON;
R15 is hydrogen, halo, C1-3 alkyl, substituted C1-3 alkyl, hydroxyalkyl, alkoxy, or substituted alkoxy;
R16 is selected from the group consisting of H, CN, NO2, halo, alkyl, cycloalkyl, alkenyl, cycloalkenyl, alkynyl, aryl, heteroaryl, heterocycloalkyl, OR1', SR1', NR1'R1", CO2R1', OCOR1', CONR1'R1", CONR1'SO2R1", NR1'COR1", NR1'CONR1"R1'", NR1'C=SNR1"R1'", NR1'SO2R1", SO2R1', and SO2NR1'R1";
R17, substituted or unsubstituted, is selected form the group consisting of hydrogen, alkyl, alkenyl, (CH2)0-3-cycloalkyl, (CH2)0-3-cycloalkenyl, (CH2)0-3-heterocycloalkyl, (CH2)0-3-aryl, and (CH2)0-3-heteroaryl;
R18 is selected form the group consisting of hydrogen, halo, NO2, CN, CF3SO2, and CF3;
R11a is selected from the group consisting of hydrogen, alkyl, heteroalkyl, alkenyl, hydroxyalkyl, alkoxy, substituted alkoxy, cycloalkyl, cycloalkenyl, and heterocycloalkyl;
R11 b is hydrogen or alkyl;
R11c is selected from the group consisting of hydrogen, alkyl, substituted alkyl, hydroxyalkyl, alkoxy, and substituted alkoxy; and
n1, r1, and s1, independently are 1, 2, 3, 4, 5, or 6;
R21 is SO2R2';
R22 is alkyl, preferably C1-4 alkyl, more preferably methyl, propyl, or isopropyl;
R23 is alkyl, preferably C1-4 alkyl, more preferably methyl, propyl, or isopropyl;
R24 is halogen, preferably fluoride, chloride;
R25 is halogen, preferably fluoride, chloride;
R26 is selected from H, halogen and alkyl, preferably fluoride, chloride, C1-4 alkyl, more preferably methyl, propyl, isopropyl;
R21b is H or alkyl, preferably C1-4 alkyl, more preferably methyl, propyl, or isopropyl;
n2, r2 and s2 are independently 1, 2, 3, 4, 5 or 6, more preferably, r2 and s2 are both 2 and n2 is 3, 4 or 5, more preferably, all of n2, r2 and s2 are 2, and
R2' is alkyl, preferably C1-4 alkyl, more preferably methyl, propyl, or isopropyl.

In some embodiments, the Bcl-2/Bcl-xL dual inhibitor is selected from the compounds of Table 2. In some embodiments, the Bcl-2/Bcl-xL dual inhibitor is selected from the group consisting of Compound 72 and Compound 88.

In some embodiments, the BTK inhibitor is selected from the group consisting of: Ibrutinib, ICP-022, Acalabrutinib (ACP-196), BGB3111, ONO/GS-4059, Spebrutinib (CC-292 or AVL-292), CNX-774, Olmutinib (HM61713, BI1482694), M7583, HM71224, PCI-32765 Racemate, GDC-0853, ONO-4059, Zanubrutinib, RN486, PCI-32765, CGI-1746, QL47, LFM-A13, (±)-Zanubrutinib, SNS-062, BMS-935177, Btk inhibitor 2, Evobrutinib, Ibrutinib-biotin, BMX-IN-1, GDC-0834 and CB1763.

In some embodiments, the combination product is in the form of a pharmaceutical composition.

In some embodiments, the Bcl-2 inhibitor and the BTK inhibitor are each in a separate preparation, or wherein the Bcl-2/Bcl-xL dual inhibitor and the BTK inhibitor are each in a separate preparation.

In some embodiments, the Bcl-2 inhibitor and the BTK inhibitor are administered simultaneously or sequentially, or wherein the Bcl-2/Bcl-xL dual inhibitor and the BTK inhibitor are administered simultaneously or sequentially.

In some embodiments, the combination product further comprises a pharmaceutically acceptable carrier, diluent or excipient.

In some embodiments, the combination product is in the form of tablet, capsule, granule, syrup, powder, lozenge, sachet, cachet, elixir, suspension, emulsion, solution, syrup, aerosol, ointment, cream and injection.

A second aspect of the invention relates to the use of a Bcl-2 inhibitor or a Bcl-2/Bcl-xL dual inhibitor and a BTK inhibitor in the manufacture of a medicament for the prevention and/or treatment of a disease selected from the group consisting of cancer, autoimmune disease and inflammatory disease.

A third aspect of the invention relates to a combination product for preventing and/or treating a disease, in which the combination product comprises a Bcl-2 inhibitor or a Bcl-2/Bcl-xL dual inhibitor and a BTK inhibitor, and the disease is selected from the group consisting of cancer, autoimmune disease and inflammatory disease.

A fourth aspect of the invention relates to a method of preventing and/or treating a disease comprising administering to a subject in need thereof a prophylactically and/or therapeutically effective amount of a Bcl-2 inhibitor or a Bcl-2/Bcl-xL dual inhibitor and a BTK inhibitor, wherein the disease is selected from cancer, autoimmune disease and inflammatory disease.

In some embodiments, the cancer is a hematological malignancy.

Preferably, the hematological malignancy is selected from the group consisting of acute myeloid leukemia (AML), acute lymphoblastic leukemia (ALL), diffuse large B-cell lymphoma (DLBCL), follicular lymphoma (FL), chronic lymphocytic leukemia (CLL)/small lymphocytic lymphoma (SLL), marginal zone lymphoma (MZL), chronic myelogenous leukemia (CML), mantle cell lymphoma (MCL), Waldenstrom's macroglobulinemia (WM), multiple myeloma (MM), small cell lung cancer (SCLC). More preferably, the hematological malignancy is diffuse large B-cell lymphoma (DLBCL) or follicular lymphoma (FL).

In some embodiments, the method of preventing and/or treating a disease, comprising administering the Bcl-2 inhibitor, the Bcl-2/Bcl-xL dual inhibitor or a pharmaceutically acceptable salt or solvate thereof in an amount of from about 0.0025 to 1500 mg per day.

In some embodiments, the method of preventing and/or treating a disease, comprising administering the BTK inhibitor or a pharmaceutically acceptable salt or solvate thereof in an amount of from about 0.0025 to 1000 mg per day.

DETAILED DESCRIPTION OF THE INVENTION

FIG. 1 shows the inhibitory effect of Ibrutinib alone and the combination of Ibrutinib and Compound 6 on proliferation in malignant tumor cells in WST experiment: OCI-LY8 (diffuse large B-cell lymphoma (DLBCL)), SU-DHL-4 (diffuse large B-cell lymphoma (DLBCL)), OCI-LY1 (diffuse large B-cell lymphoma (DLBCL)), DOHH2 (follicular lymphoma (FL)), RPMI-8226 (multiple myeloma (MM)), KMS-11 (multiple myeloma (MM)), Z-138 (mantle cell lymphoma (MCL)).

FIGS. 6A and 6B represents the cell viability test from human FL DOHH-2 and DLBCL OCI-LY1, respectively.

Figure 7:
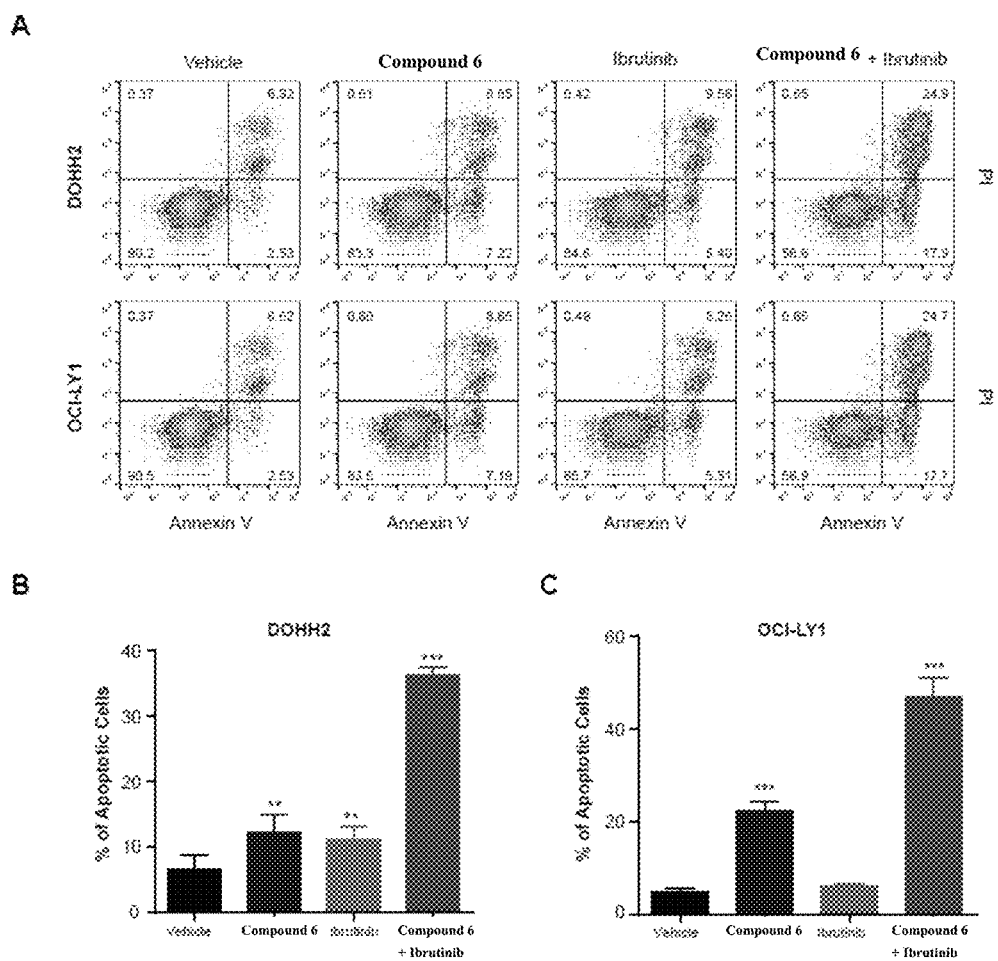

FIG. 7 shows the synergistic induction of apoptosis of FL (follicular lymphoma, FL) and DLBCL (diffuse large B-cell lymphoma (DLBCL)) cells by combination treatment with Compound 6 and ibrutinib in vitro. FIG. 7A shows Flow cytometry analysis of apoptotic cells by Annexin V and propidium iodide (PI) co-staining in DOHH-2 and OCI-LY1 cell lines treated with 10 nM (DOHH-2) or 15 nM (OCI-LY1) Compound 6, 100 nM (DOHH-2) or 150 nM (OCI-LY1) ibrutinib, or the combination for 24 hours. FIG. 7B shows the percentages of Annexin V-positive, PI-positive, or double positive DOHH-2 according to FIG. 7A. FIG. 7c shows the percentages of Annexin V-positive, PI-positive, or double positive OCI-LY1 according to FIG. 7A.

Figure 8:
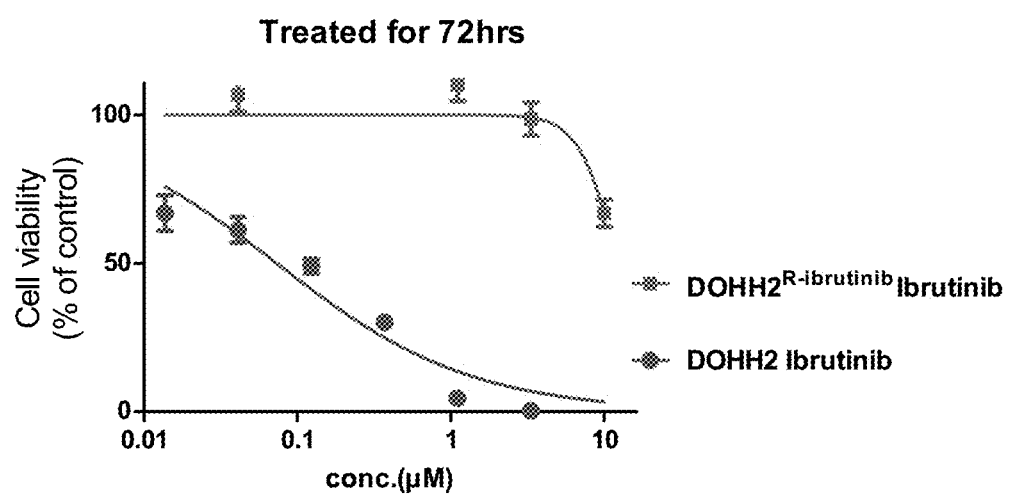

FIG. 8 shows the inhibitory effect of ibrutinib on the growth of DOHH2 cells and DOHH2R-ibrutinib cells. DOHH2R-ibrutinib cells shows resistance to ibrutinib.

Figure 9:
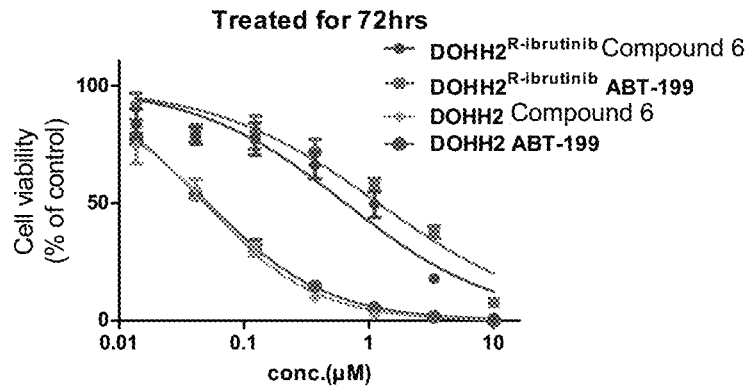

FIG. 9 shows the inhibitory effect of Compound 6 and ABT-199 on the growth of DOHH2 cells and DOHH2R-ibrutinib cells.

Figure 10:
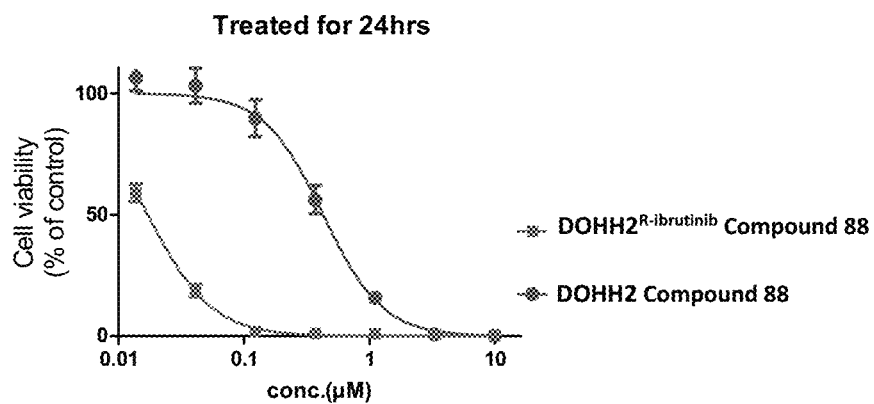

FIG. 10 shows the inhibitory effect of Compound 88 on the growth of DOHH2 cells and DOHH2R-ibrutinib cells.

DEFINITIONS

The term "BTK inhibitor" as used herein refers to a substance that inhibits the activity of a BTK enzyme, or a substance that degrades a BTK enzyme, or a genetic tool that reduces the level of a BTK enzyme.

The term "resistance" as used herein refers to be resistant or non-responsive to a therapeutic agent (e.g., a BTK inhibitor, ibrutinib). For example, the number of tumor cells still increases despite of receiving the treatment with a therapeutic agent.

The term "pharmaceutically acceptable salt" as used herein, refers to a salt of a free acid or a free base, usually prepared by reacting the free base with a suitable organic or inorganic acid or by reacting the acid with a suitable organic or inorganic base. This term can be used in any of the compounds of the invention. Representative salts include: acetate, besylate, benzoate, bicarbonate, hydrogen sulfate, hydrogen tartrate, borate, bromide, calcium edetate, camphorsulfonate, carbonate, chloride, clavulanate, citrate, dihydrochloride, edetate, ethanedisulfonate, estolate, esylate, fumarate, glucoheptonate, gluconate, glutamate, glycolylarsanilate, hexylresorcinate, hydrabamine, hydrobromide, hydrochloride, hydroxynaphthoate, iodide, isethionate, lactate, lactobionate, laurate, malate, maleate, mandelate, methanesulfonate, methylbroide, methylnitrate, methylsulfate, monopotassium maleate, mucate, naphthalenesulfonate, nitrate, N-methylglucosamine salt, oxalate, pamoate (dihydroxylnaphthalate), palmitate, pantothenate, phosphate/diphosphate, polygalacturonate, potassium salt, salicylate, sodium salt, stearate, subacetate, succinate, tannate, tartrate, teoclate, p-toluenesulfonate, triethiodide, trimethylamine salt and valerate. When an acidic substituent is present, such as —COOH, an ammonium salt, morpholine salt, sodium salt, potassium salt, barium salt, calcium salt or the like can be formed for use in a dosage form. When a basic group is present (for example, in a limonoid compound or a 1,1-dimethylbiguanide), such as an amino group or basic heteroaryl group such as a pyridyl group, an acidic salt can be formed, such as hydrochloride, hydrobromide, phosphate, sulfate, trifluoroacetate, trichloroacetate, acetate, oxalate, maleate, pyruvate, malonate, succinate, citrate, tartrate, fumarate, mandelate, benzoate, cinnamate, methanesulfonate, ethanesulfonate, picrate, and the like.

The term "prevention/preventing" as used herein refers to a compound or medicament (e.g, a combination product as claimed herein) can reduce a frequency of a symptom of a medical condition in a subject or delay the onset thereof when it is applied to a disease or condition (e.g., cancer), in comparison with a subject to which the compound or medicament is not applied.

The term "treatment/treating" as used herein refers to reducing, alleviating or ameliorating a symptoms of a disease or condition, ameliorating a symptom caused by a potential metabolism, inhibiting a disease or symptom, such as preventing a disease or a disorder from progression, ameliorating a disease or condition, causing regression of a disease or condition, alleviating a condition caused by a disease or condition, or preventing a symptom of a disease or condition.

The term "cancer" as used herein refers to a new neoplasm or tumor caused by abnormal, uncontrolled cell growth. Non-limiting examples include those exemplary cancers described in the description of the invention. The term "cancer" includes diseases involving both pre-malignant cancer cells and malignant cancer cells.

The term "solvate" as used herein is a combination, physical binding, and/or solvation of a compound of the invention with a solvent molecule, such as a disolvate, a monosolvate, a hemisolvate. The compounds of the present invention may be in a solvate form with a pharmaceutically acceptable solvent such as water, methanol, ethanol, etc., which does not significantly affect the pharmacological activity or toxicity of the compounds and which may act as a pharmacological equivalent.

The term "subject" as used herein refers to including humans (e.g, patients) and animals (e.g, mice, rats, dogs, cats, rabbits, chickens, monkeys, etc.). When the subject is a human patient (usually calculated as body weight of 60 kg), a dose described herein can be obtained by conversion performed with a conversion factor for an experimental animal (e.g, human dose=mouse dose/12.3) unless otherwise stated (Kin Tam. "Estimating the "First in human" dose-a revisit with particular emphasis on oncology drugs, ADMET & DMPK 1 (4) (2013) 63-75). Those of ordinary skill in the art can reasonably adjust the dose based on common sense and according to the specific weight of subject, the type and severity of disease, and other factors, and all of these adjusted technical solutions fall within the scope of the technical solutions claimed in the present invention.

The term "effective amount" or "prophylactically and/or therapeutically effective amount" as used herein refers to a sufficient amount (e.g, a dose) of a medicament or compound to be administered that will alleviate one or more symptoms of a disease or condition to be treated to some extent. The result can be a reduction and/or alleviation in the cause of condition or disease or any other desired changes in biological system. For example, an "effective amount" for therapeutic use is an amount of a compound or medicament (e.g, a combination product as claimed herein) that provides a significant reduction in the clinical symptoms of the disease or condition without causing excessive toxic side effects.

The term "dose" as used herein refers to a weight (e.g, milligrams (mg)) of an active substance per kilogram (kg) of a subject's body weight.

The term "IC50" as used herein refers to an amount, concentration or dose of a particularly tested compound or medicament that achieves a 50% inhibition of maximum effect in an assay that measures such effect, for example inhibition of BCL-2 or BTK.

The term "room temperature" as used herein refers to 25° C.±1° C. At the same time, if the experimental temperature is not specified, it is room temperature.

The term "about" as used herein refers to ±10%, more preferably ±5%, and most preferably ±2% of the value modified by the term, so that one of ordinary skill in the art can clearly determine the scope of the term "about" according to the modified value.

The terms "aliphatic ring", "heterocycle", "heterocycloalkyl", "heteroalkyl", "cycloalkylalkyl" and "halogen" as used herein have the ordinary meanings in the art, and a person of ordinary skill in the art will be able to understand the meaning thereof by the general knowledge or by reference to the prior art (for example, WO 2018/027097, the entire disclosure of which is incorporated herein by reference).

The term "Ibrutinib" as used herein is a compound having the structure:

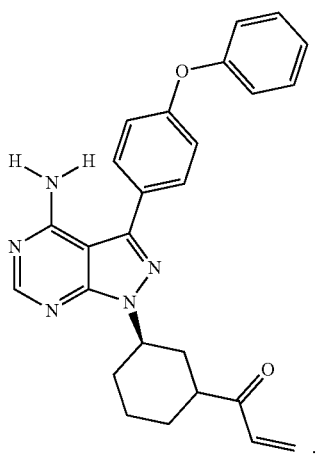 [SMILES: C=CC(=O)C1CCC[C@@H](n2nc(-c3ccc(Oc4ccccc4)cc3)c3c(N)ncnc32)C1]

DETAILED DESCRIPTION OF THE INVENTION

In a first aspect of the invention relates to a combination product comprising or consisting of a Bcl-2 inhibitor and a BTK inhibitor. In a first aspect of the invention relates to a combination product comprising or consisting of a Bcl-2/Bcl-xL dual inhibitor and a BTK inhibitor.

In another aspect of the invention relates to a method of treating a disease (e.g., cancer, autoimmune disease, and inflammatory disease) in a subject in need thereof, comprising administering to the subject a therapeutically effective amount of the Bcl-2 Inhibitor or the Bcl-2/Bcl-xL dual inhibitor, wherein the subject is refractory or is resistant to a BTK inhibitor. In certain embodiments, the subject is refractory or is resistant to ibrutinib.

In some embodiments, the Bcl-2 inhibitor is a compound of Formula I-A, or a pharmaceutically acceptable salt or solvate thereof:

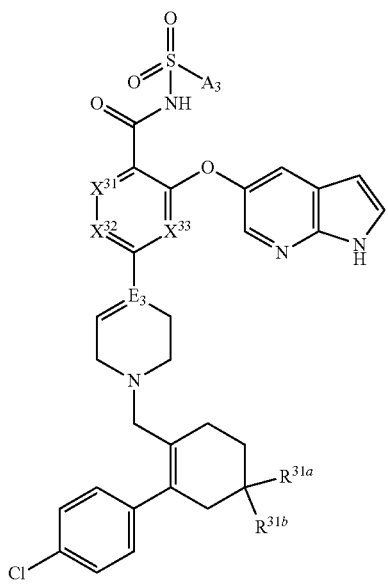

I-A wherein:

A3 is

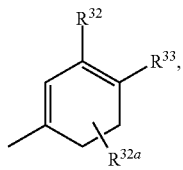  A-1

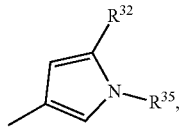  A-2

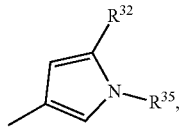  A-3

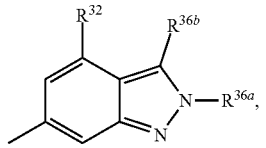  A-4

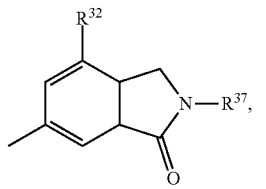  A-5

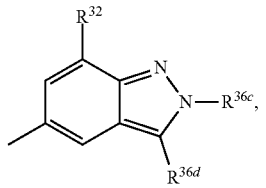  A-6

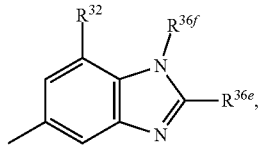  A-7

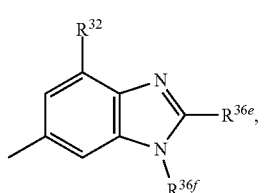  A-8

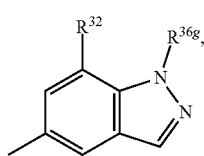

A-9 and

A-10

E3 is a carbon atom and ═ is a double bond; or
E3 is a —C(H)— and ═ is a single bond; or
E3 is a nitrogen atom and ═ is a single bond;
X31, X32 and X33 are each independently selected from the group consisting of —CR38═ and —N═;
R31a and R31b taken together with the carbon atom to which they are attached form a 3-, 4-, or 5-membered optionally substituted aliphatic ring;
R31a and R31b taken together with the carbon atom to which they are attached form a 4- or 5-membered optionally substituted heterocyclo;
R32 is selected from the group consisting of —NO2, —SO2CH3, and —SO2CF3;
R32a is selected from the group consisting of hydrogen and X;
R33 is selected from the group consisting of hydrogen, —CN, —C≡CH, and —N(R34a)(R34b);
R34a is selected from the group consisting of optionally substituted C1-6 alkyl, optionally substituted C3-6 cycloalkyl, heterocyclo, heteroalkyl, cycloalkylalkyl, and heterocycloalkyl;
R34b is selected from the group consisting of hydrogen and C1-4 alkyl;
R35 is selected from the group consisting of optionally substituted C1-6 alkyl, heterocyclo, cycloalkylalkyl, and heterocycloalkyl;
R36a, R36c, R36e, R36f, and R36g are each independently selected from the group consisting of hydrogen, optionally substituted C1-6 alkyl, optionally substituted C3-6 cycloalkyl, optionally substituted aryl, optionally substituted heteroaryl, heterocyclo, heteroalkyl, cycloalkylalkyl, and heterocycloalkyl;
R36b and R36d are each independently selected from the group consisting of hydrogen, C1-4 alkyl, and halogen;
R37 is selected from the group consisting of optionally substituted C1-6 alkyl, heterocyclo, heteroalkyl, cycloalkylalkyl, and heterocycloalkyl;
R38 is selected from the group consisting of hydrogen and halogen.
In the above compound of Formula I-A, the "X" in the definition of variant R32a refers to halogen. Further, halogen mentioned above refers to F, Cl, Br, or I.

In some embodiments, the Bcl-2 inhibitor is a compound of Formula I-A, wherein: A3 is selected from the group consisting of A-1, A-2, A-3, A-4, A-5, A-6, A-7, A-8, and A-9; R34a is selected from the group consisting of optionally substituted C1-6 alkyl, heterocyclo, heteroalkyl, cycloalkylalkyl, and heterocycloalkyl; R36a, R36c, R36e, R36f and R36g are each independently selected from the group consisting of hydrogen, optionally substituted C1-6 alkyl, heterocyclo, heteroalkyl, cycloalkylalkyl, and heterocycloalkyl.

In some embodiments, the Bcl-2 inhibitor is a compound of Formula I-b, or a pharmaceutically acceptable salt or solvate thereof, I-b wherein:
E3 is a carbon atom and ═ is a double bond; or E3 is —C(H)— and ═ is a single bond; or E3 is a nitrogen atom and ═ is a single bond;
R31a and R31b together with the carbon atom connected thereto form a 3-, 4-, or 5-membered optionally substituted aliphatic ring; or
R31a and R31b together with the carbon atom connected thereto form a 4- or 5-membered optionally substituted heterocyclo;
R32 is selected from the group consisting of —NO2, —SO2CH3, and —SO2CF3;
R33 is selected from the group consisting of hydrogen, —CN, —C≡CH, and —N(R34a)(R34b);
R34a is selected from the group consisting of optionally substituted C1-6 alkyl, heterocyclo, cycloalkylalkyl, and heterocycloalkyl;
R34b is selected from the group consisting of hydrogen and C1-4 alkyl.

In some embodiments, the Bcl-2 inhibitor is a compound of Formula I-c, or a pharmaceutically acceptable salt or solvate thereof,

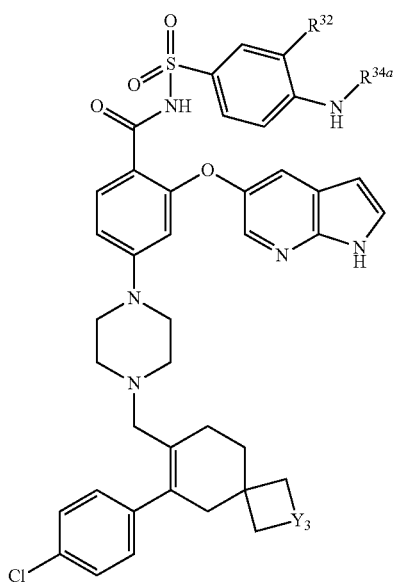

I-c wherein:

Y3 is selected from the group consisting of —CH2— and —O—, and R32 and R34a are as defined in connection with Formula I-b.

In some embodiments, the Bcl-2 inhibitor is a compound of Formula I-d, or a pharmaceutically acceptable salt or solvate thereof,

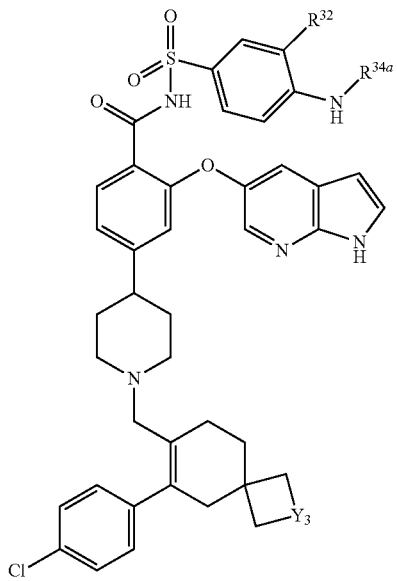

I-d wherein:

Y3 is selected from the group consisting of —CH2— and —O—, and R32 and R34a are as defined in connection with Formula I-b.

In some embodiments, the Bcl-2 inhibitor is a compound of Formula I-e, or a pharmaceutically acceptable salt or solvate thereof,

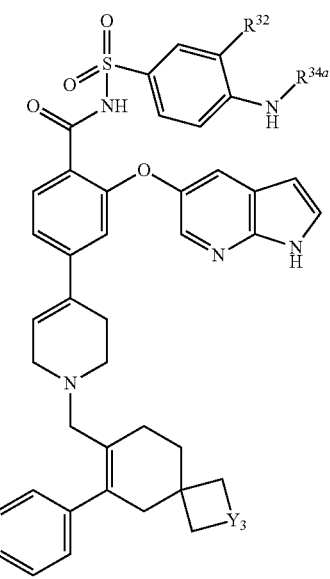

I-e wherein:

Y3 is selected from the group consisting of —CH2— and —O—, and R32 and R34a are as defined in connection with Formula I-b.

In some embodiments, the Bcl-2 inhibitor is a compound of Formula I-f, or a pharmaceutically acceptable salt or solvate thereof,

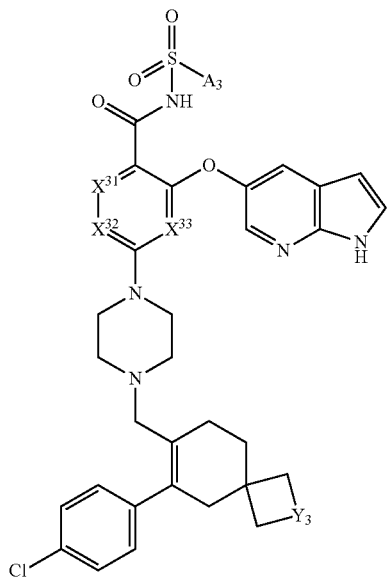

I-f wherein:

Y3 selected from the group consisting of —CH2— and —O—, and A3, X31, X32, and X33 are as defined in connection with Formula I-A.

In some embodiments, the Bcl-2 inhibitor is a compound of Formula I-g, or a pharmaceutically acceptable salt or solvate thereof,

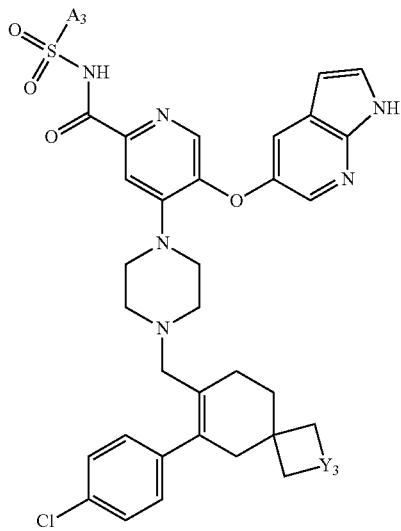

I-g

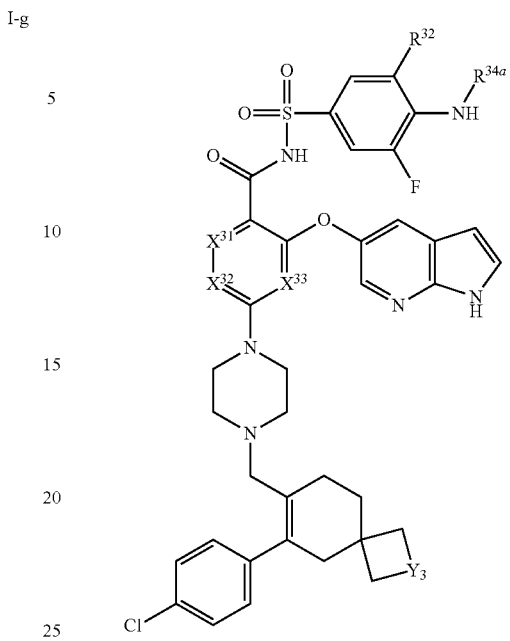

I-h wherein

Y3 selected from the group consisting of —CH2— and —O—, and A3 is as defined in connection with Formula I-A.

In some embodiments, the Bcl-2 inhibitor is a compound of Formula I-A, I-f or I-g, or a pharmaceutically acceptable salt or solvate thereof, wherein A3 is A-1.

In some embodiments, the Bcl-2 inhibitor is a compound of Formula I-A, I-f or I-g, or a pharmaceutically acceptable salt or solvate thereof, wherein A3 is A-2.

In some embodiments, the Bcl-2 inhibitor is a compound of Formula I-A, I-f or I-g, or a pharmaceutically acceptable salt or solvate thereof, wherein A3 is A-3.

In some embodiments, the Bcl-2 inhibitor is a compound of Formula I-A, I-f or I-g, or a pharmaceutically acceptable salt or solvate thereof, wherein A3 is A-4.

In some embodiments, the Bcl-2 inhibitor is a compound of Formula I-A, I-f or I-g, or a pharmaceutically acceptable salt or solvate thereof, wherein A3 is A-5.

In some embodiments, the Bcl-2 inhibitor is a compound of Formula I-A, I-f or I-g, or a pharmaceutically acceptable salt or solvate thereof, wherein A3 is A-6.

In some embodiments, the Bcl-2 inhibitor is a compound of Formula I-A, I-f or I-g, or a pharmaceutically acceptable salt or solvate thereof, wherein A3 is A-7.

In some embodiments, the Bcl-2 inhibitor is a compound of Formula I-A, I-f or I-g, or a pharmaceutically acceptable salt or solvate thereof, wherein A3 is A-8.

In some embodiments, the Bcl-2 inhibitor is a compound of Formula I-A, I-f or I-g, or a pharmaceutically acceptable salt or solvate thereof, wherein A3 is A-9.

In some embodiments, the Bcl-2 inhibitor is a compound of Formula I-A, I-f or I-g, or a pharmaceutically acceptable salt or solvate thereof, wherein A3 is A-10.

In some embodiments, the Bcl-2 inhibitor is a compound of Formula I-h, or a pharmaceutically acceptable salt or solvate thereof, wherein Y3 selected from the group consisting of —CH2— and —O—, and X31, X32, X33, R32, and R34a are as defined in connection with Formula I-A.

In some embodiments, the Bcl-2 inhibitor is a compound of Formula I-A, I-f or I-h, or a pharmaceutically acceptable salt or solvate thereof, wherein all X31, X32, and X33 —CH═.

In some embodiments, the Bcl-2 inhibitor is a compound of Formula I-A, I-f or I-h, or a pharmaceutically acceptable salt or solvate thereof, wherein X1 is —CF═, and both X32 and X33 are —CH═.

In some embodiments, the Bcl-2 inhibitor is a compound of Formula I-A, I-f or I-h, or a pharmaceutically acceptable salt or solvate thereof, wherein both X31 and X33 are —CH═, and X32 is —CF═.

In some embodiments, the Bcl-2 inhibitor is a compound of Formula I-A, I-f or I-h, or a pharmaceutically acceptable salt or solvate thereof, wherein both X31 and X32 are —CH═, and X33 is —CF═.

In some embodiments, the Bcl-2 inhibitor is a compound of Formula I-A, I-f or I-h, or a pharmaceutically acceptable salt or solvate thereof, wherein X31 is —N═, and both X32 and X33 are —CH═.

In some embodiments, the Bcl-2 inhibitor is a compound of Formula I-A, I-f or I-h, or a pharmaceutically acceptable salt or solvate thereof, wherein X31 and X33 are each —CH═, and X32 is —N═.

In some embodiments, the Bcl-2 inhibitor is a compound of Formula I-A, I-f or I-h, or a pharmaceutically acceptable salt or solvate thereof, wherein both X31 and X32 are —CH═, and X33 is —N═.

In some embodiments, the Bcl-2 inhibitor is a compound of any one of Formulae I-c to I-h, or a pharmaceutically acceptable salt or solvate thereof, wherein Y3 is —O—.

In some embodiments, the Bcl-2 inhibitor is a compound of any one of Formulae I-c to I-h, or a pharmaceutically acceptable salt or solvate thereof, wherein Y3 is —CH2—.

In some embodiments, the Bcl-2 inhibitor is a compound of any one of Formulae I-A or I-h, or a pharmaceutically acceptable salt or solvate thereof, wherein R32 is —NO2.

In some embodiments, the Bcl-2 inhibitor is a compound of any one of Formulae I-g, or a pharmaceutically acceptable salt or solvate thereof, wherein R34a is selected from the group consisting of:

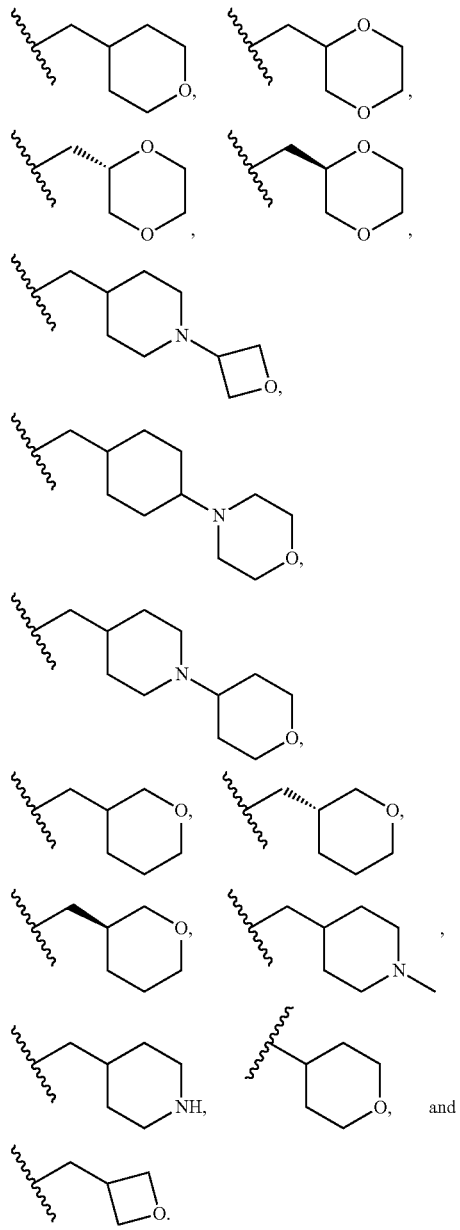

and

In some embodiments, the Bcl-2 inhibitor is a compound of any one of Formulae I-A or I-f to I-h, or a pharmaceutically acceptable salt or solvate thereof, wherein $R^{34A}$, $R^{35}$, $R^{36a}$, and $R^{37}$ are each independently selected from the group consisting of:

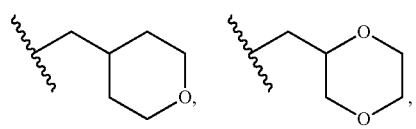

-continued

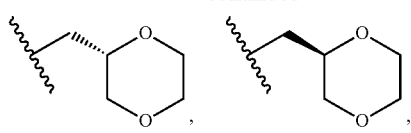

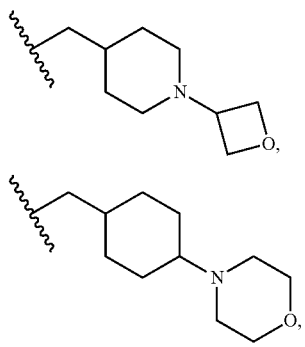

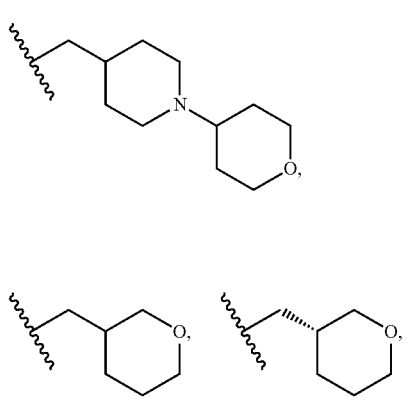

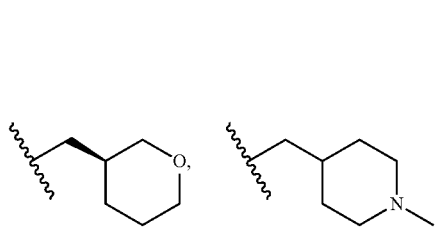

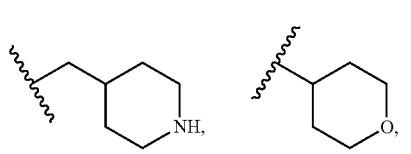

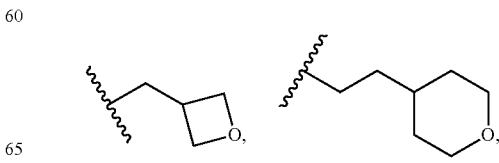

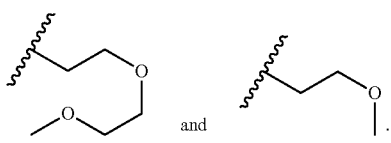 and 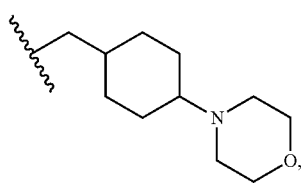

In some embodiments, the Bcl-2 inhibitor is a compound of Formula I-i, or a pharmaceutically acceptable salt or solvate thereof, wherein $R^{32a}$ is hydrogen or fluoro and $R^{34a}$ is as defined in connection with Formula I-A.

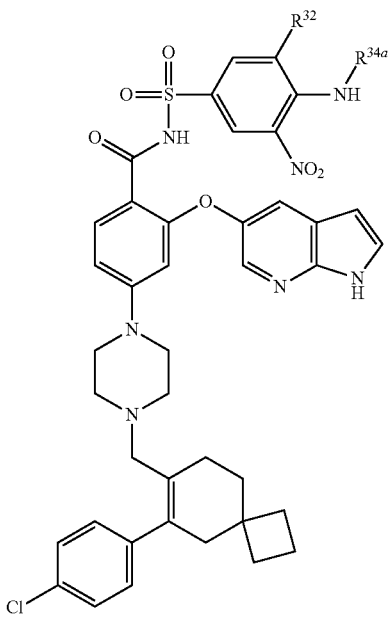

I-i

In some embodiments, the Bcl-2 inhibitor is a compound of Formula I-i, or a pharmaceutically acceptable salt or solvate thereof, wherein $R^{34a}$ is selected from the group consisting of:

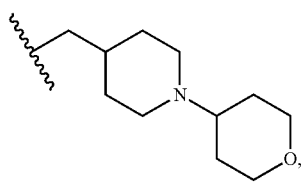

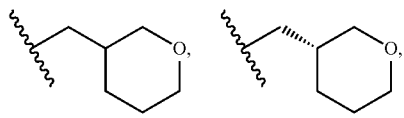

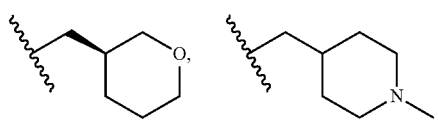

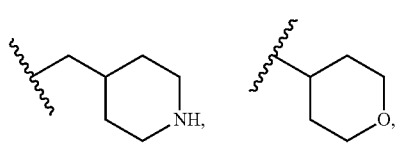

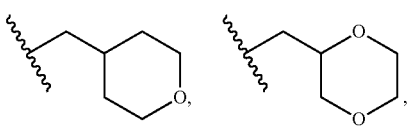 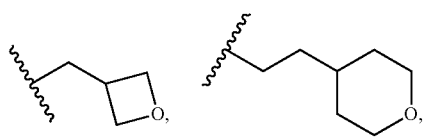

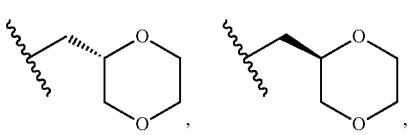

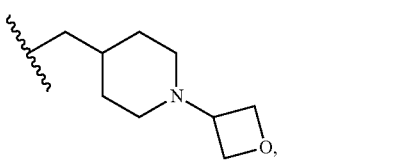

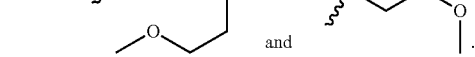

In some embodiments, the Bcl-2 inhibitor is a compound selected from one or more of the compounds of Table 1, or a pharmaceutically acceptable salt or solvate thereof.

TABLE 1

| Cpd. No. | Structure | Name |
|---|---|---|
| 1 | 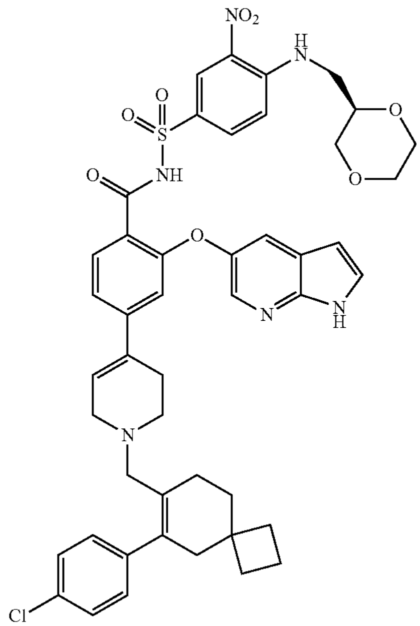 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CCC4)CC3)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)benzamide |
| 2 | 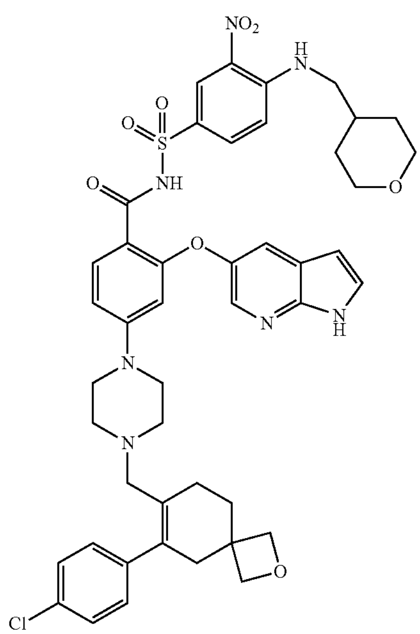 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)-N-((3-nitro-4-(((tetrahydro-2H-pyran-4-yl)methyl)amino)phenyl)sulfonyl)benzamide |

TABLE 1-continued
| Cpd. No. | Structure | Name |
|---|---|---|
| 3 | 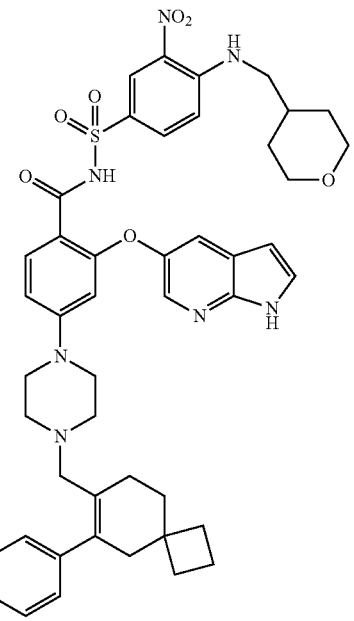 | 2-((1H-pyrrolo[2,3-b]pyridin-5-yl)oxy)-4-((4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide |
| 4 | 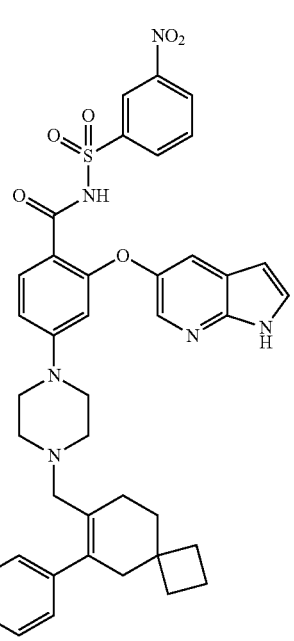 | 2-((1H-pyrrolo[2,3-b]pyridin-5-yl)oxy)-4-((4-((6-(4-chlorophenyl)spiro[3.5]non-6-en-7-yl)methyl)piperazin-1-yl)-N-((3-nitrophenyl)sulfonyl)benzamide |

TABLE 1-continued

| Cpd. No. | Structure | Name |
|---|---|---|
| 5 | 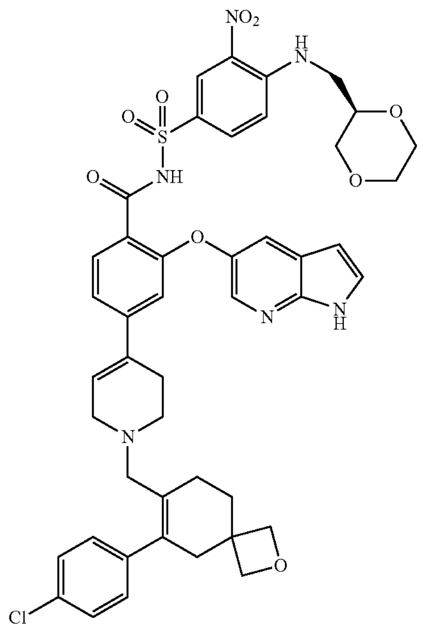 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CC3)COC4)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)benzamide |
| 6 | 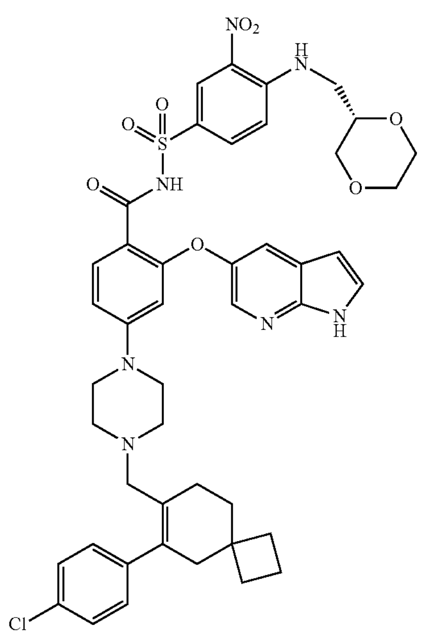 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-continued
| Cpd. No. | Structure | Name |
|---|---|---|
| 7 | 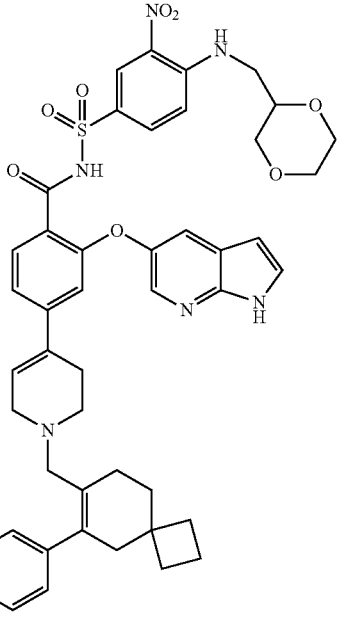 | 2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |
| 8 | 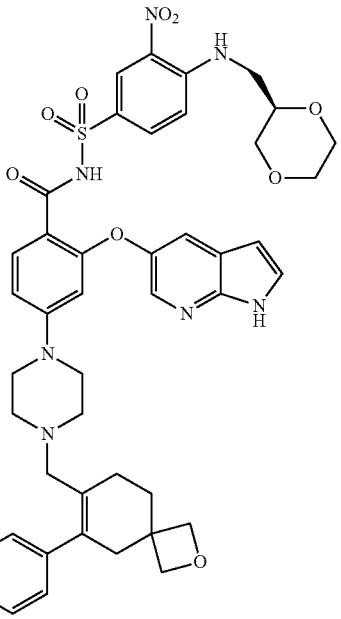 | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzamide |

TABLE 1-continued

| Cpd. No. | Structure | Name |
|---|---|---|
| 9 | 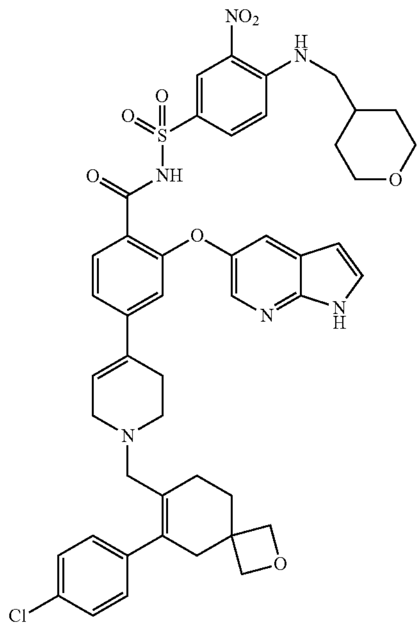 [SMILES: O=C(NS(=O)(=O)c1ccc(NCC2CCOCC2)c([N+](=O)[O-])c1)c1ccc(C2=CCN(CC3=C(c4ccc(Cl)cc4)CC4(CC3)COC4)CC2)cc1Oc1cnc2[nH]ccc2c1] | 2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |
| 10 | 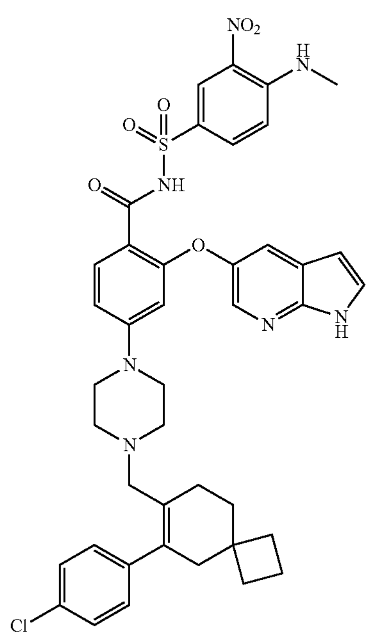 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(methylamino)-3-nitrophenyl)sulfonyl)benzamide |

TABLE 1-continued

| Cpd. No. | Structure | Name |
|---|---|---|
| 11 | 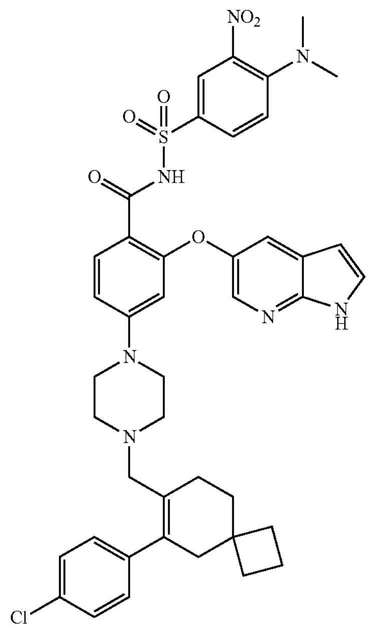 [SMILES: CN(C)c1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(dimethylamino)-3-nitrophenyl)sulfonyl)benzamide |
| 12 | 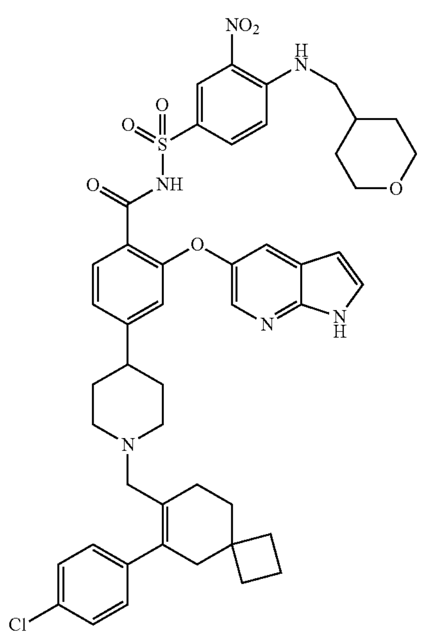 [SMILES: O=C(NS(=O)(=O)c1ccc(NCC2CCOCC2)c([N+](=O)[O-])c1)c1ccc(C2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(1-((6-(4-chlorophenyl)spiro[3.5]non-6-en-7-yl)methyl)piperidin-4-yl)-N-((3-nitro-4-(((tetrahydro-2H-pyran-4-yl)methyl)amino)phenyl)sulfonyl)benzamide |

TABLE 1-continued
| Cpd. No. | Structure | Name |
|---|---|---|
| 13 | 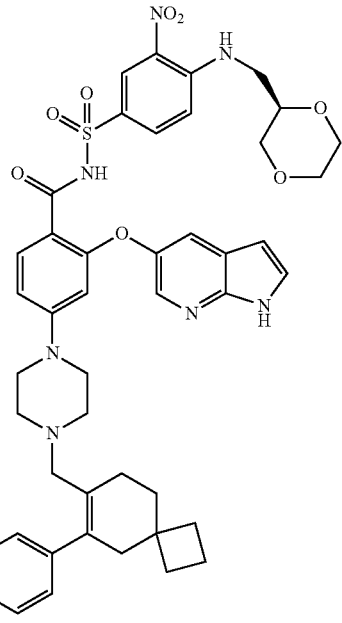 | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 14 | 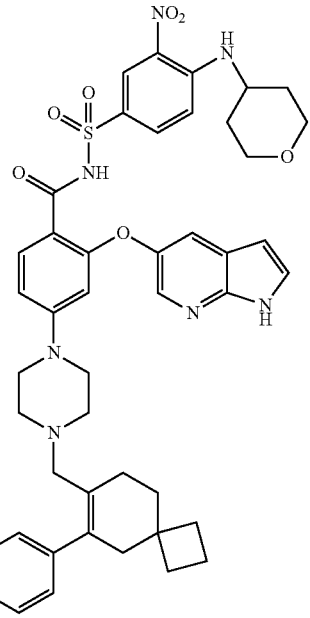 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((tetrahydro-2H-pyran-4-yl)amino)phenyl)sulfonyl)benzamide |

TABLE 1-continued
| Cpd. No. | Structure | Name |
|---|---|---|
| 15 | 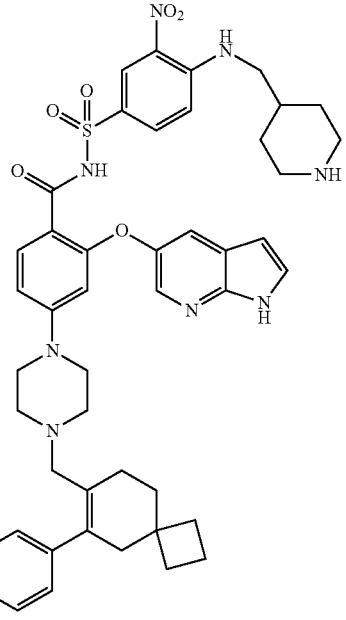 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((piperidin-4-ylmethyl)amino)phenyl)sulfonyl)benzamide |
| 16 | 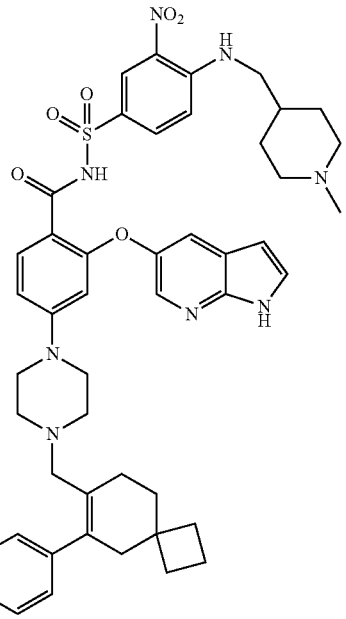 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(((1-methylpiperidin-4-yl)methyl)amino)-3-nitrophenyl)sulfonyl)benzamide |

TABLE 1-continued

| Cpd. No. | Structure | Name |
|---|---|---|
| 17 | 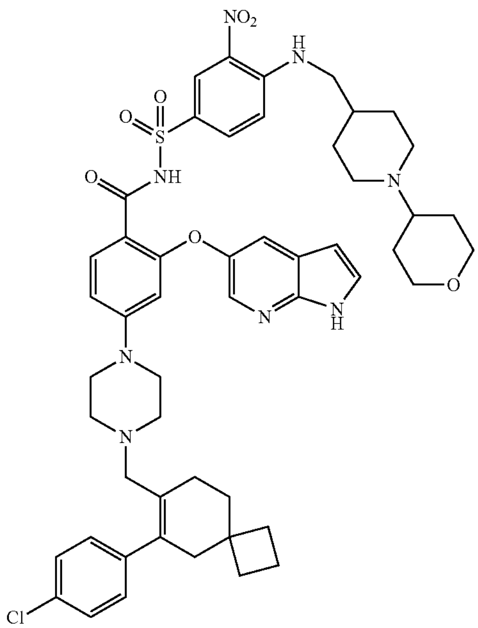 [SMILES: O=C(NS(=O)(=O)c1ccc(NCC2CCN(C3CCOCC3)CC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((1-(tetrahydro-2H-pyran-4-yl)piperidin-4-yl)methyl)amino)phenyl)sulfonyl)benzamide |
| 18 | 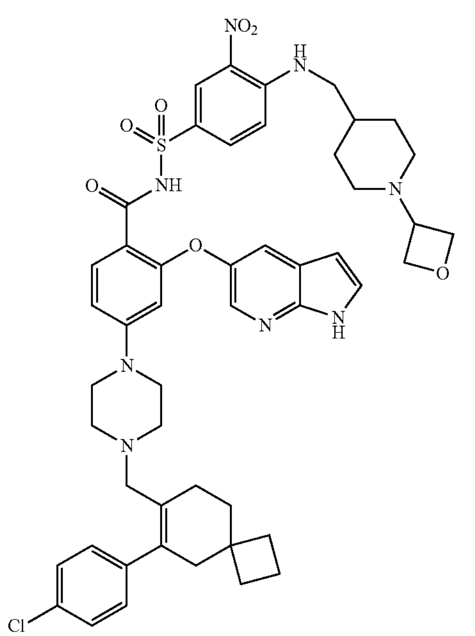 [SMILES: O=C(NS(=O)(=O)c1ccc(NCC2CCN(C3COC3)CC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((1-(oxetan-3-yl)piperidin-4-yl)methyl)amino)phenyl)sulfonyl)benzamide |

TABLE 1-continued

| Cpd. No. | Structure | Name |
|---|---|---|
| 19 | 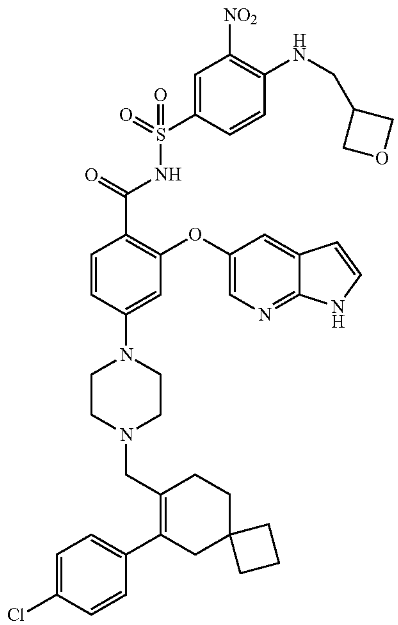 [SMILES: O=C(NS(=O)(=O)c1ccc(NCC2COC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((oxetan-3-ylmethyl)amino)phenyl)sulfonyl)benzamide |
| 20 | 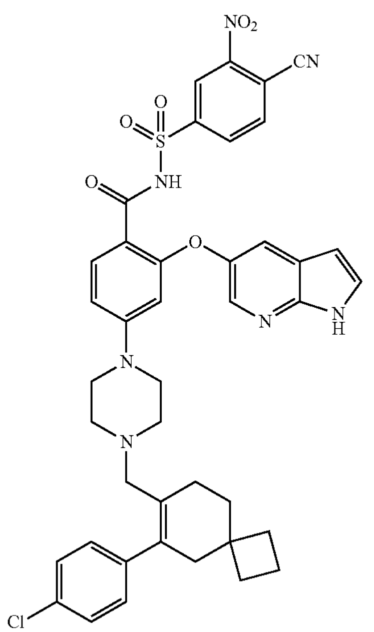 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-cyano-3-nitrophenyl)sulfonyl)benzamide |

| Cpd. No. | Structure | Name |
|---|---|---|
| 21 | 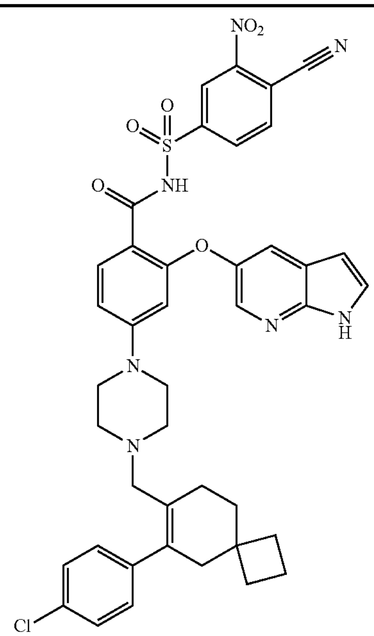 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-ethynyl-3-nitrophenyl)sulfonyl)benzamide |

In some embodiments, the Bcl-2 inhibitor is a compound selected from one or more of the compounds of Table 1-A, or a pharmaceutically acceptable salt or solvate thereof.

TABLE 1-A

| Cpd. No. | Structure | Name |
|---|---|---|
| 22 | 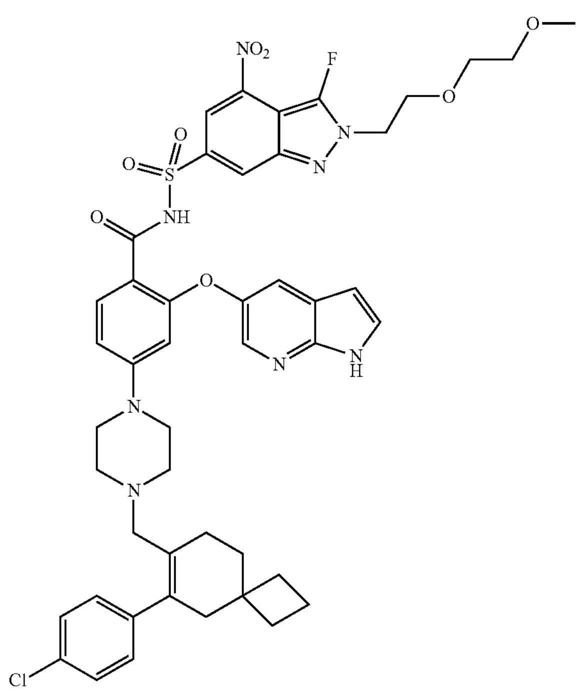 [SMILES: COCCOCCn1nc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2c1F] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-fluoro-2-(2-(2-methoxyethoxy)ethyl)-4-nitro-2H-indazol-6-yl)sulfonyl)benzamide |

TABLE 1-A-continued
| Cpd. No. | Structure | Name |
|---|---|---|
| 23 | 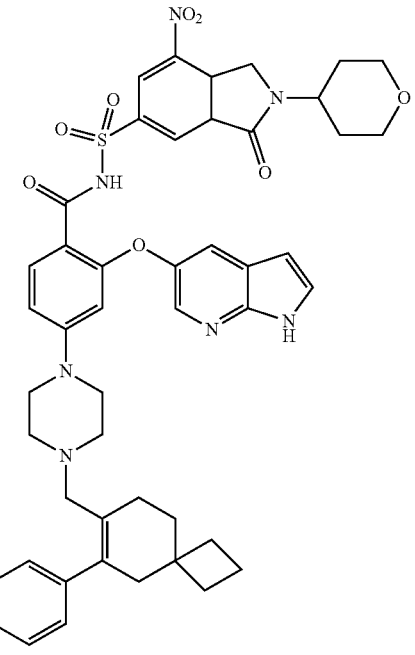 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-3-oxo-2-(tetrahydro-2H-pyran-4-yl)-2,3,3a,7a-tetrahydro-1H-isoindol-5-yl)sulfonyl)benzamide |
| 24 | 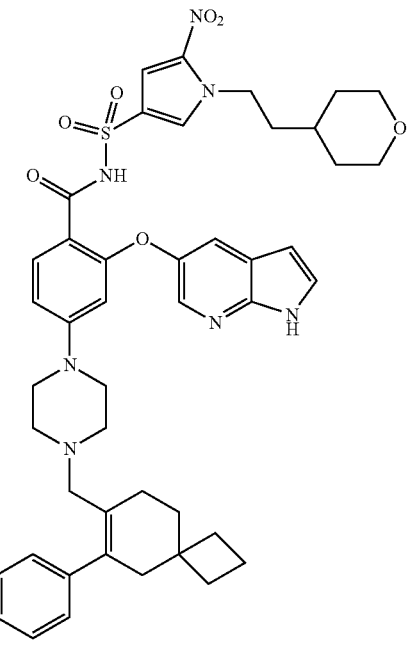 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((5-nitro-1-(2-(tetrahydro-2H-pyran-4-yl)ethyl)-1H-pyrrol-3-yl)sulfonyl)benzamide |

TABLE 1-A-continued
| Cpd. No. | Structure | Name |
|---|---|---|
| 25 | 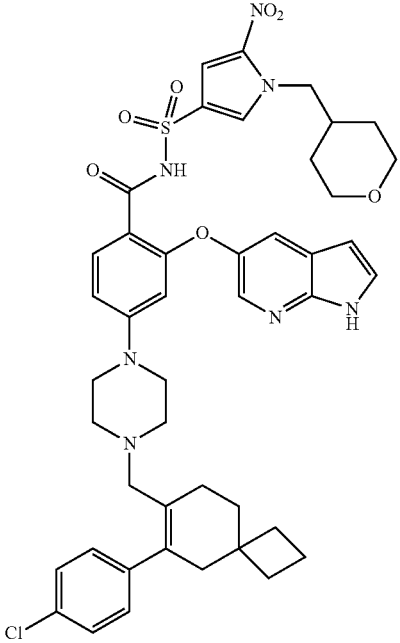 [SMILES: O=C(NS(=O)(=O)c1cc([N+](=O)[O-])n(CC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-((6-(4-chlorophenyl)spiro[3.5]non-6-en-7-yl)methyl)piperazin-1-yl)-N-((5-nitro-1-((tetrahydro-2H-pyran-4-yl)methyl)-1H-pyrrol-3-yl)sulfonyl)benzamide |
| 26 | 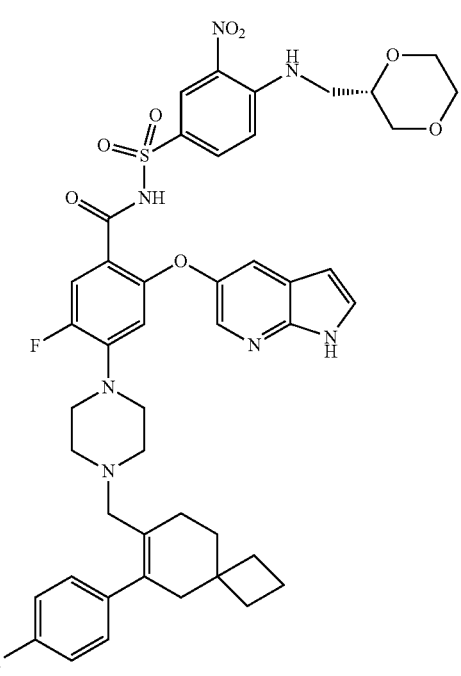 | (S)-N-((4-(((1,4-dioxan-2-yl)methyl)amino)-3-nitrophenyl)sulfonyl)-2-((1H-pyrrolo[2,3-b]pyridin-5-yl)oxy)-4-((6-(4-chlorophenyl)spiro[3.5]non-6-en-7-yl)methyl)piperazin-1-yl)-5-fluorobenzamide |

TABLE 1-A-continued
| Cpd. No. | Structure | Name |
|---|---|---|
| 27 | 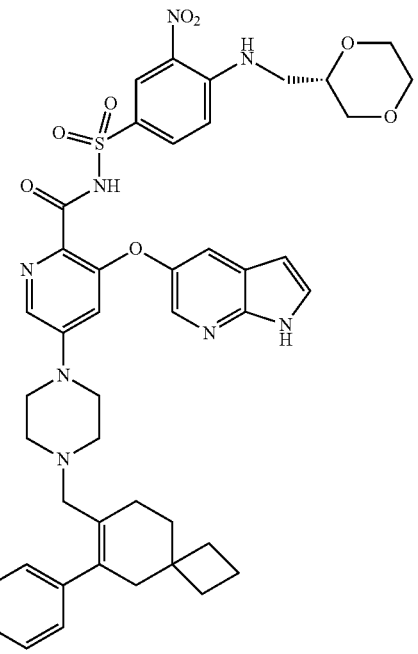 | (S)-N-((4-(((1,4-dioxan-2-yl)methyl)amino)-3-nitrophenyl)sulfonyl)-3-((1H-pyrrolo[2,3-b]pyridin-5-yl)oxy)-5-(4-((6-(4-chlorophenyl)spiro[3.5]non-6-en-7-yl)methyl)piperazin-1-yl)picolinamide |
| 28 | 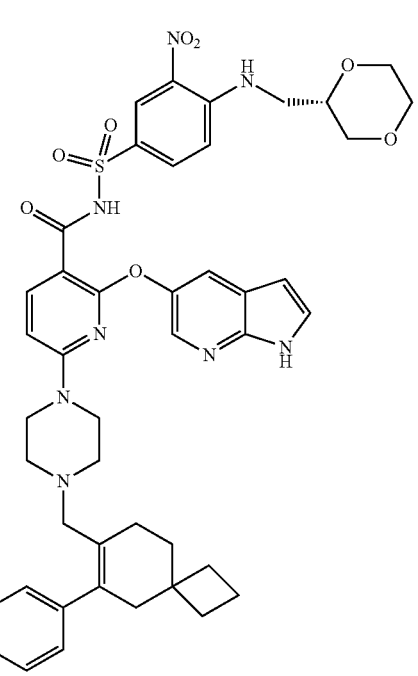 | (S)-N-((4-(((1,4-dioxan-2-yl)methyl)amino)-3-nitrophenyl)sulfonyl)-2-((1H-pyrrolo[2,3-b]pyridin-5-yl)oxy)-6-(4-((6-(4-chlorophenyl)spiro[3.5]non-6-en-7-yl)methyl)piperazin-1-yl)nicotinamide |

TABLE 1-A-continued

| Cpd. No. | Structure | Name |
|---|---|---|
| 29 | 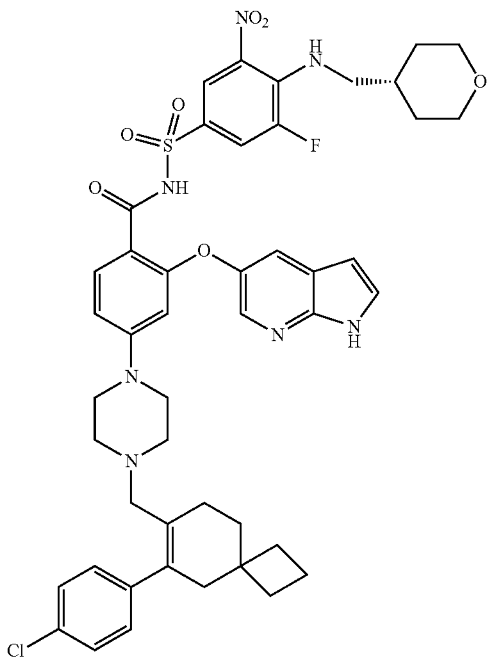 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-fluoro-5-nitro-4-(((tetrahydro-2H-pyran-4-yl)methyl)amino)phenyl)sulfonyl)benzamide |
| 30 | 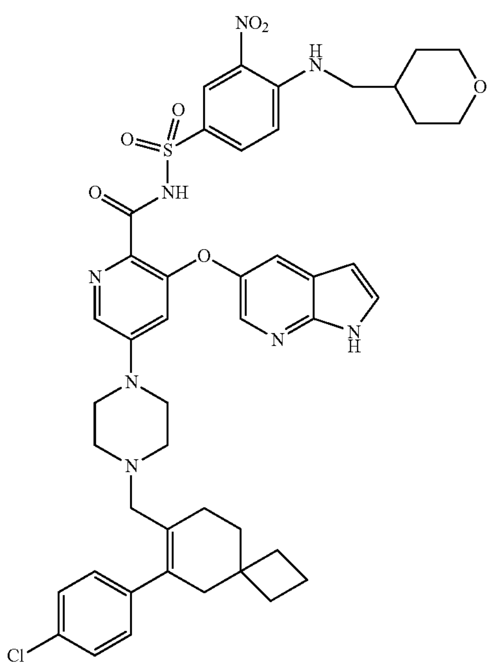 [SMILES: O=C(NS(=O)(=O)c1ccc(NCC2CCOCC2)c([N+](=O)[O-])c1)c1ncc(N2CCN(CC3=C(c4ccc(Cl)cc4)CC4(CCC4)CC3)CC2)cc1Oc1cnc2[nH]ccc2c1] | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)picolinamide |

TABLE 1-A-continued
| Cpd. No. | Structure | Name |
|---|---|---|
| 31 | 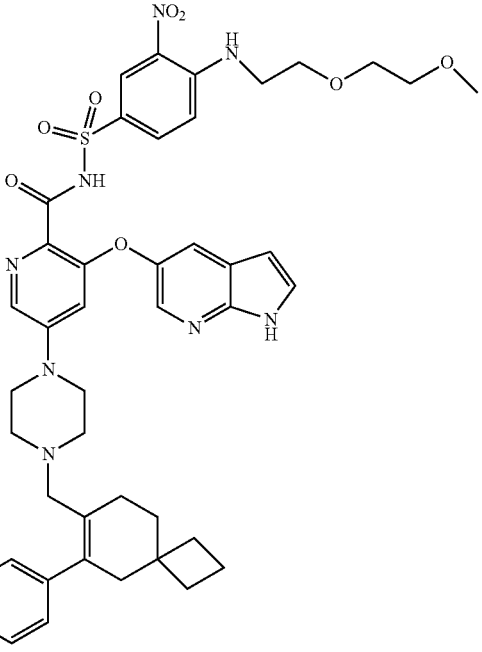 | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)picolinamide |
| 32 | 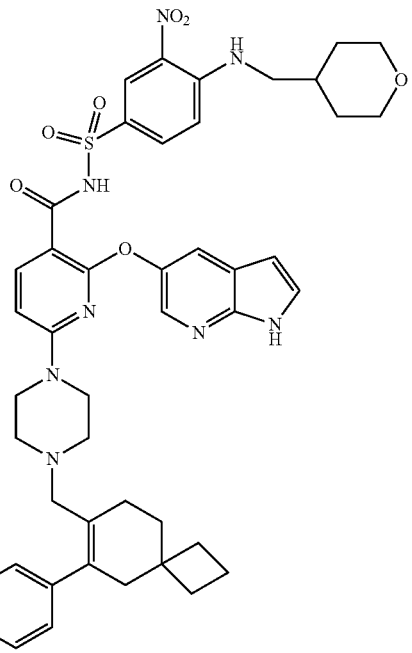 | 2-((1H-pyrrolo[2,3-b]pyridin-5-yl)oxy)-6-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)nicotinamide |

TABLE 1-A-continued

| Cpd. No. | Structure | Name |
|---|---|---|
| 33 | 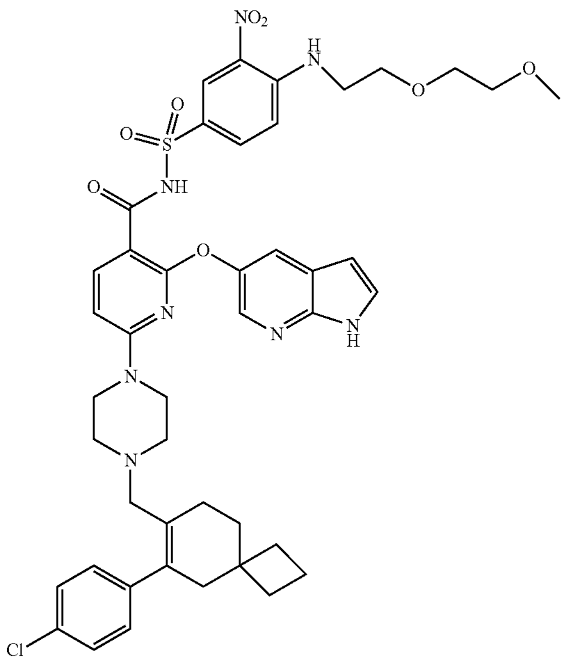 [SMILES: COCCOCCNc1ccc(S(=O)(=O)NC(=O)c2ccc(N3CCN(CC4=C(c5ccc(Cl)cc5)CC5(CCC5)CC4)CC3)nc2Oc2cnc3[nH]ccc3c2)cc1[N+](=O)[O-]] | 2-((1H-pyrrolo[2,3-b]pyridin-5-yl)oxy)-6-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)nicotinamide |
| 34 | 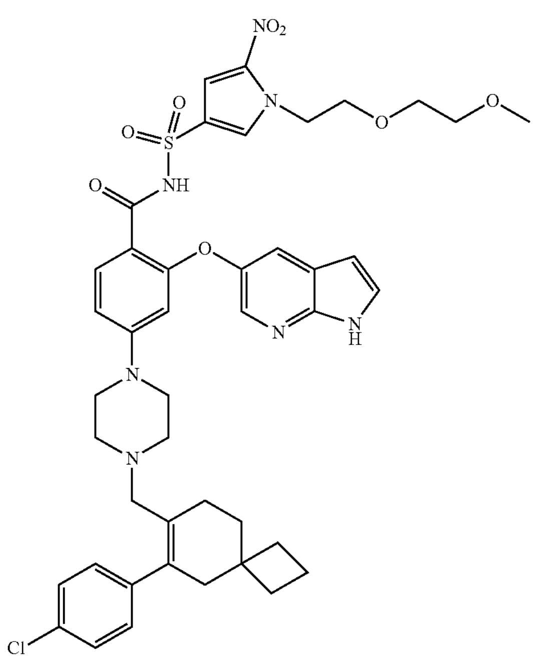 [SMILES: COCCOCCn1cc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)picolinamide |

TABLE 1-A-continued
| Cpd. No. | Structure | Name |
|---|---|---|
| 35 | 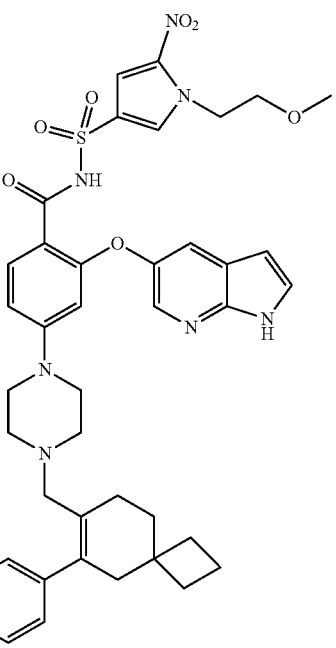 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-(2-methoxyethyl)-5-nitro-1H-pyrrol-3-yl)sulfonyl)benzamide |
| 36 | 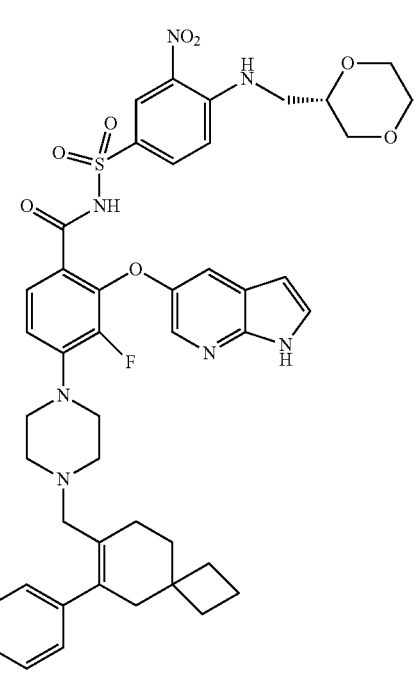 | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluorobenzamide |

TABLE 1-A-continued

| Cpd. No. | Structure | Name |
|---|---|---|
| 37 | 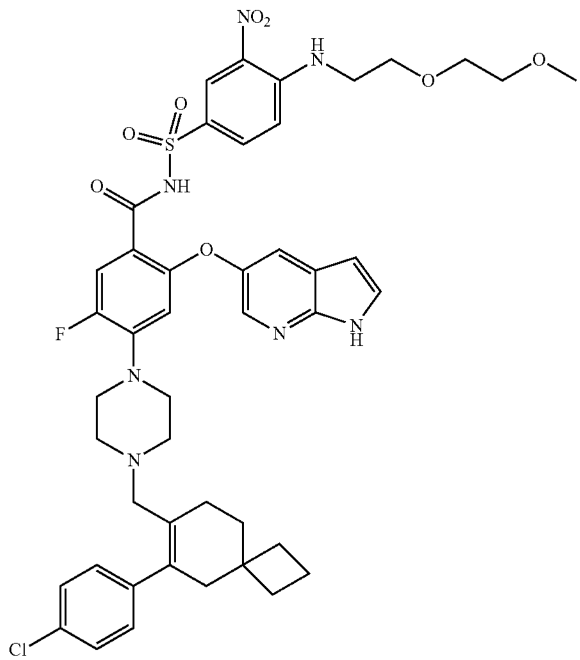 [SMILES: COCCOCCNc1ccc(S(=O)(=O)NC(=O)c2cc(F)c(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluoro-N-((4-((2-(2-methoxyethoxy)ethyl)amino)-3-nitrophenyl)sulfonyl)benzamide |
| 38 | 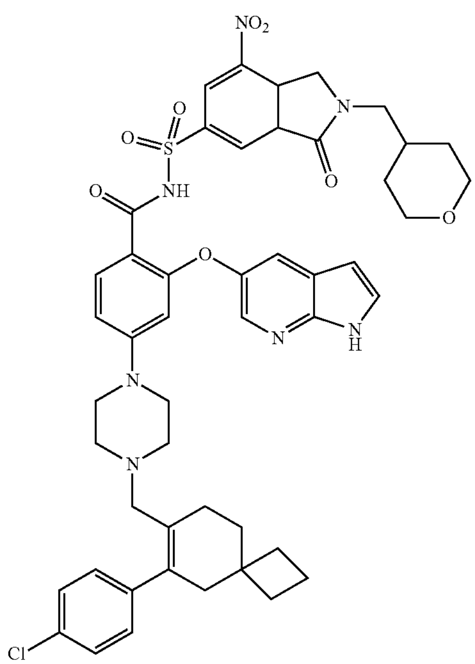 [SMILES: O=C(NS(=O)(=O)C1=CC2C(=O)N(CC3CCOCC3)CC2C([N+](=O)[O-])=C1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-3-oxo-2-((tetrahydro-2H-pyran-4-yl)methyl)-2,3,3a,7a-tetrahydro-1H-isoindol-5-yl)sulfonyl)benzamide |

| Cpd. No. | Structure | Name |
|---|---|---|
| 39 | 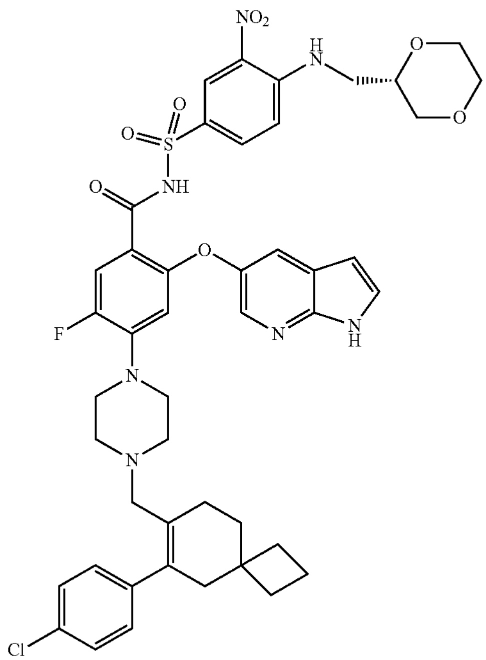 [SMILES: O=C(NS(=O)(=O)c1ccc(NC[C@H]2COCCO2)c([N+](=O)[O-])c1)c1cc(F)c(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluorobenzamide |
| 40 | 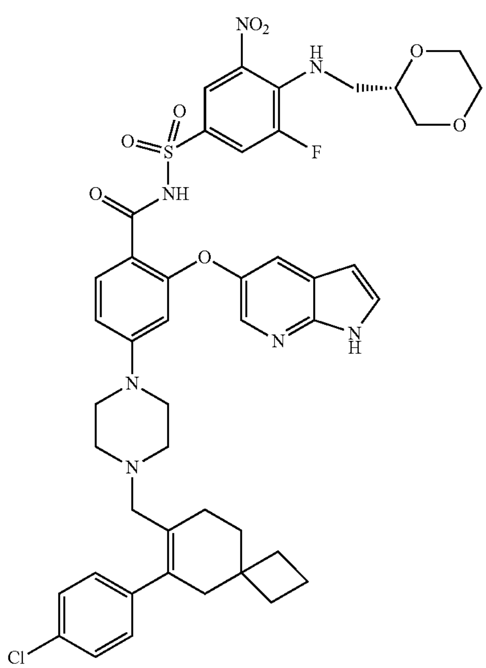 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-A-continued
| Cpd. No. | Structure | Name |
|---|---|---|
| 41 | 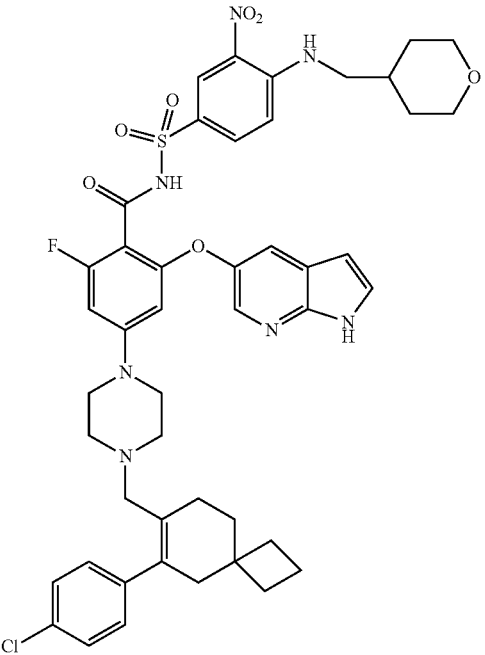 [SMILES: O=C(NS(=O)(=O)c1ccc(NCC2CCOCC2)c([N+](=O)[O-])c1)c1c(F)cc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-6-fluoro-N-((3-nitro-4-(((tetrahydro-2H-pyran-4-yl)methyl)amino)phenyl)sulfonyl)benzamide |
| 42 | 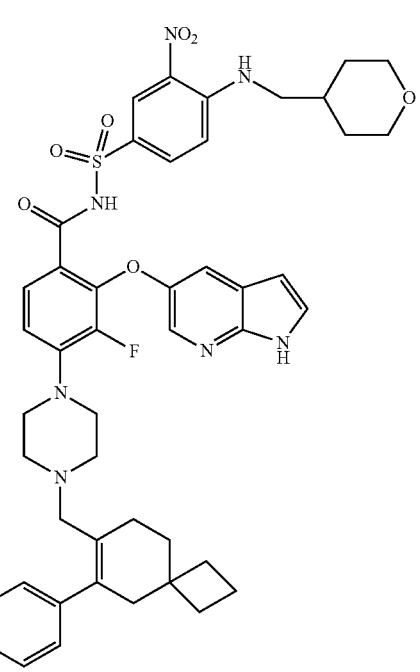 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluoro-N-((3-nitro-4-(((tetrahydro-2H-pyran-4-yl)methyl)amino)phenyl)sulfonyl)benzamide |

TABLE 1-A-continued
| Cpd. No. | Structure | Name |
|---|---|---|
| 43 | 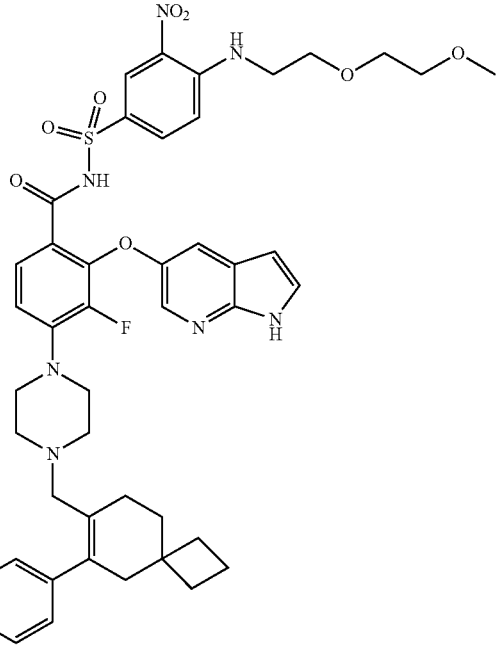 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluoro-N-((4-((2-(2-methoxyethoxy)ethyl)amino)-3-nitrophenyl)sulfonyl)benzamide |
| 44 | 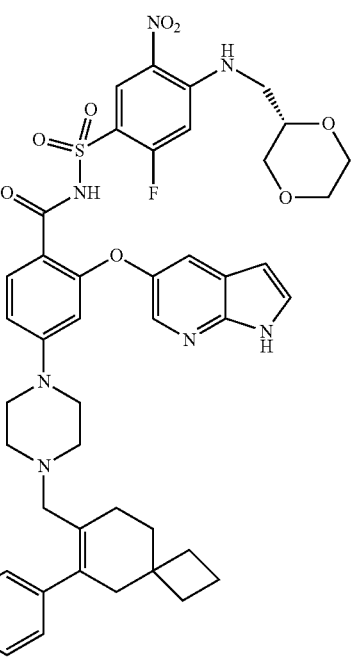 | (S)-N-((4-(((1,4-dioxan-2-yl)methyl)amino)-2-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-A-continued

| Cpd. No. | Structure | Name |
|---|---|---|
| 45 | 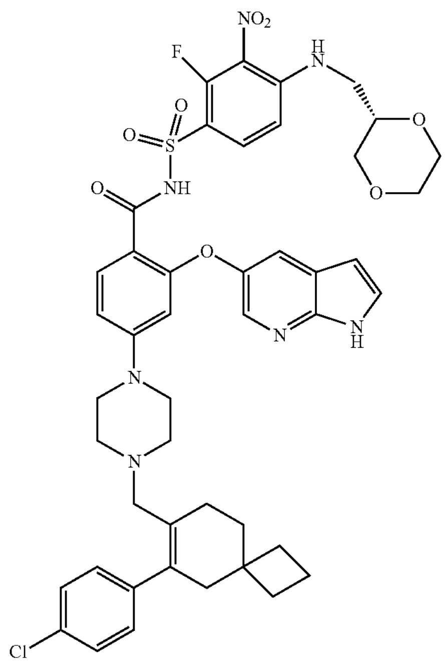 [SMILES: O=C(NS(=O)(=O)c1ccc(NC[C@H]2COCCO2)c([N+](=O)[O-])c1F)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-2-fluoro-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 46 | 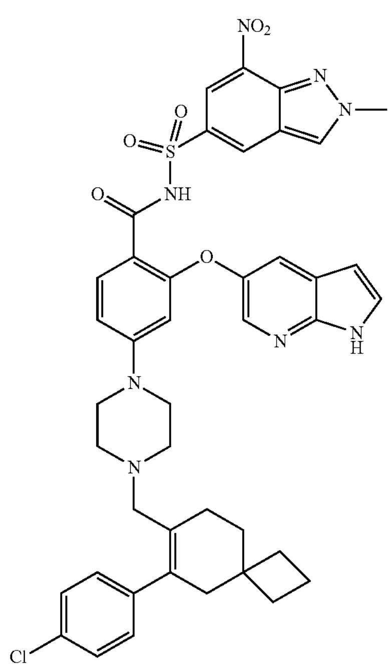 [SMILES: Cn1cc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2n1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-methyl-7-nitro-2H-indazol-5-yl)sulfonyl)benzamide |

TABLE 1-A-continued

| Cpd. No. | Structure | Name |
|---|---|---|
| 47 | 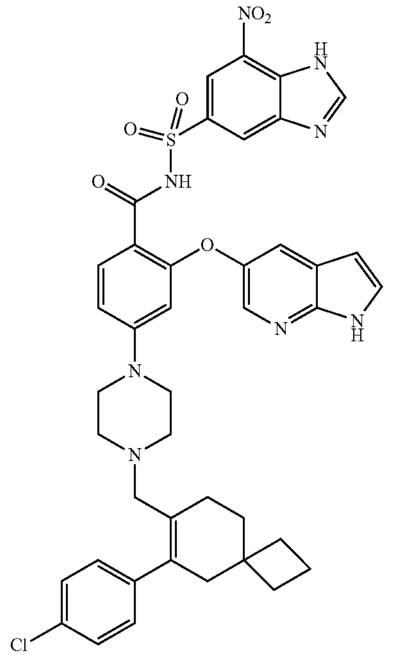 [SMILES: O=C(NS(=O)(=O)c1cc([N+](=O)[O-])c2[nH]cnc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4((6-(4-chlorophenyl)spiro[3.5]non-6-en-7-yl)methyl)piperazin-1-yl)-N-((7-nitro-1H-benzo[d]imidazol-5-yl)sulfonyl)benzamide |
| 48 | 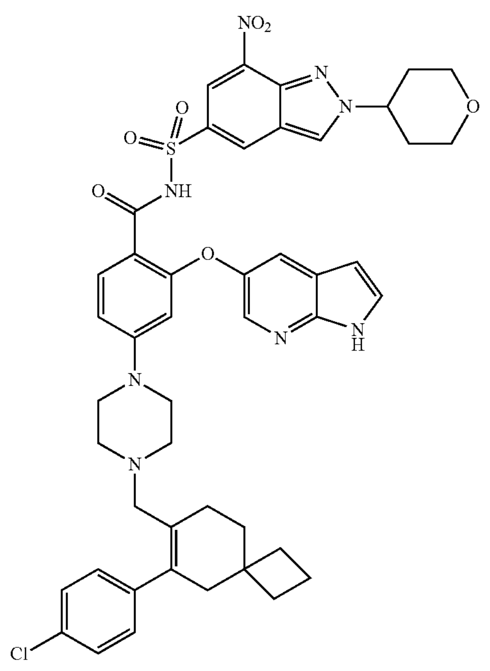 [SMILES: O=C(NS(=O)(=O)c1cc([N+](=O)[O-])c2nn(C3CCOCC3)cc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-(tetrahydro-2H-pyran-4-yl)-2H-indazol-5-yl)sulfonyl)benzamide |

TABLE 1-A-continued

| Cpd. No. | Structure | Name |
|---|---|---|
| 49 | 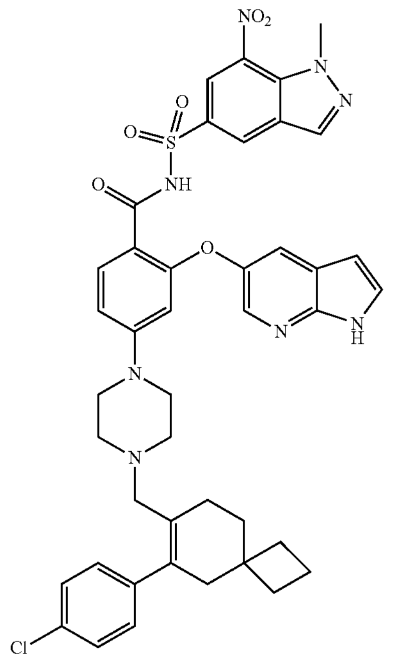 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-7-nitro-1H-indazol-5-yl)sulfonyl)benzamide |
| 50 | 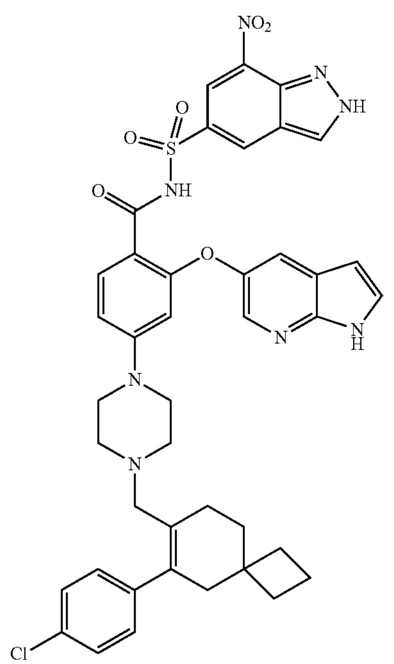 [SMILES: O=C(NS(=O)(=O)c1cc([N+](=O)[O-])c2n[nH]cc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2H-indazol-5-yl)sulfonyl)benzamide |

TABLE 1-A-continued

| Cpd. No. | Structure | Name |
|---|---|---|
| 51 | 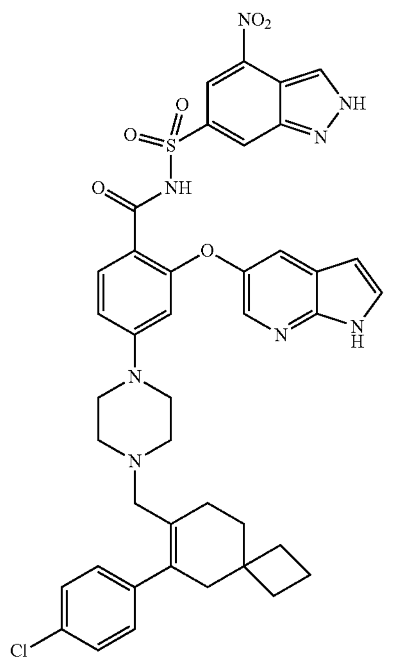 [SMILES: O=C(NS(=O)(=O)c1cc([N+](=O)[O-])c2c[nH]nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2H-indazol-6-yl)sulfonyl)benzamide |
| 52 | 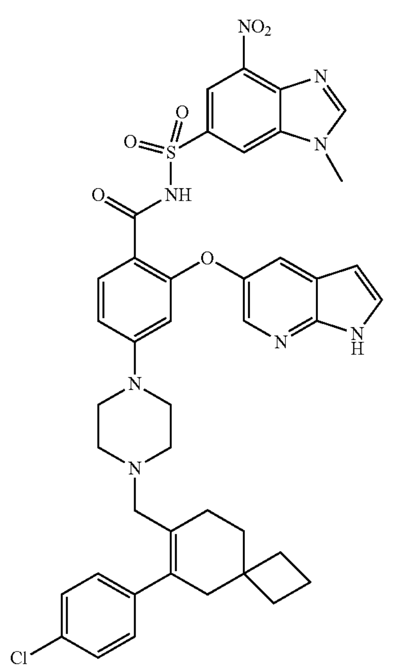 [SMILES: Cn1cnc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc21] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-4-nitro-1H-benzo[d]imidazol-6-yl)sulfonyl)benzamide |

| Cpd. No. | Structure | Name |
|---|---|---|
| 53 | 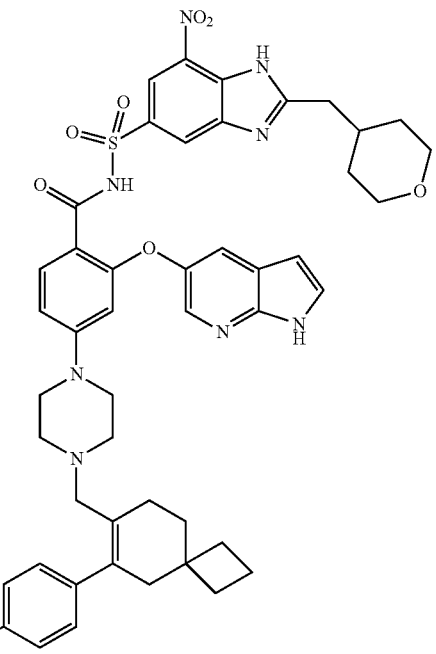 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-((tetrahydro-2H-pyran-4-yl)methyl)-1H-benzo[d]imidazol-5-yl)sulfonyl)benzamide |
| 54 | 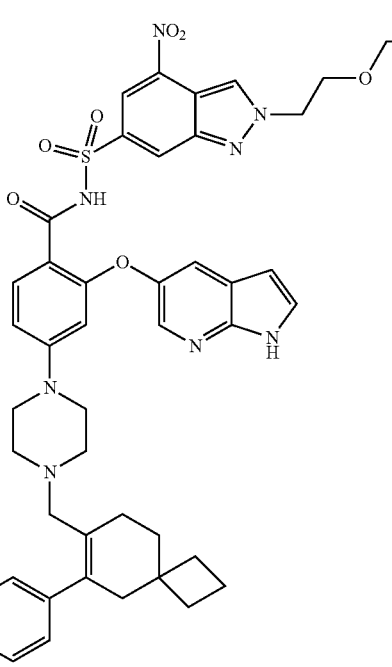 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-(2-methoxyethoxy)ethyl)-4-nitro-2H-indazol-6-yl)sulfonyl)benzamide |

| Cpd. No. | Structure | Name |
|---|---|---|
| 55 | 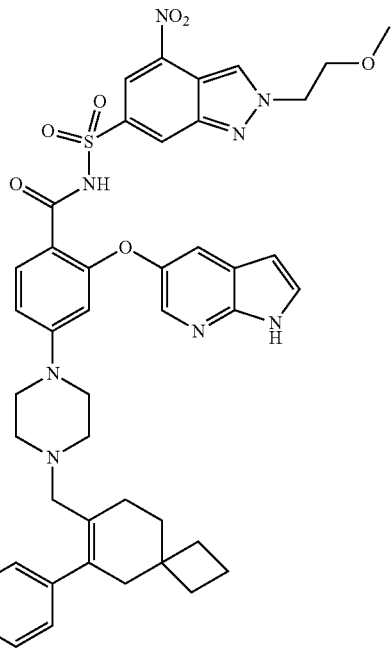 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-methoxyethyl)-4-nitro-2H-indazol-6-yl)sulfonyl)benzamide |
| 56 | 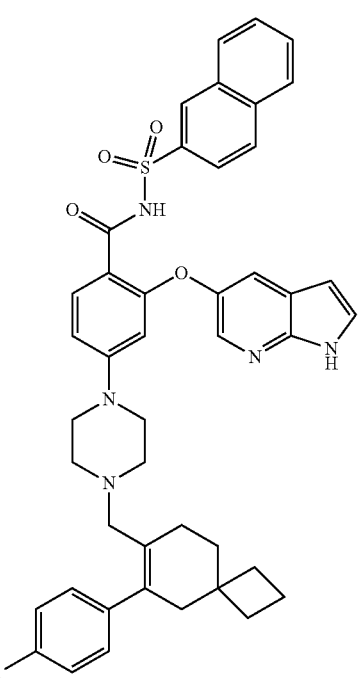 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-(naphthalen-2-ylsulfonyl)benzamide |

In some embodiments, the Bcl-2 inhibitor is a compound selected from one or more of the compounds of Table 1-B, or a pharmaceutically acceptable salt or solvate thereof.

TABLE 1-B

| Cpd. No. | Structure | Name |
|---|---|---|
| 57 | 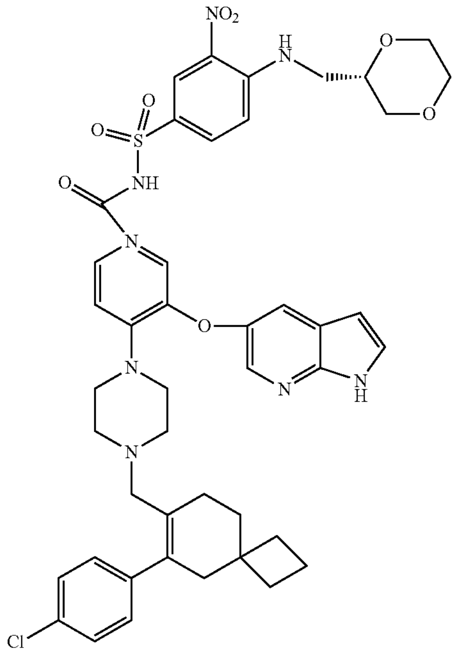 | (S)-N-((4-(((1,4-dioxan-2-yl)methyl)amino)-3-nitrophenyl)sulfonyl)-5-(((1H-pyrrolo[2,3-b]pyridin-5-yl)oxy)-4-(4-((6-(4-chlorophenyl)spiro[3.5]non-6-en-7-yl)methyl)piperazin-1-yl)picolinamide |

In some embodiments, the Bcl-2/Bcl-xL dual inhibitor is a compound of formula (I), (II), (Ill) or (IV), or a pharmaceutically acceptable salt or solvate thereof:

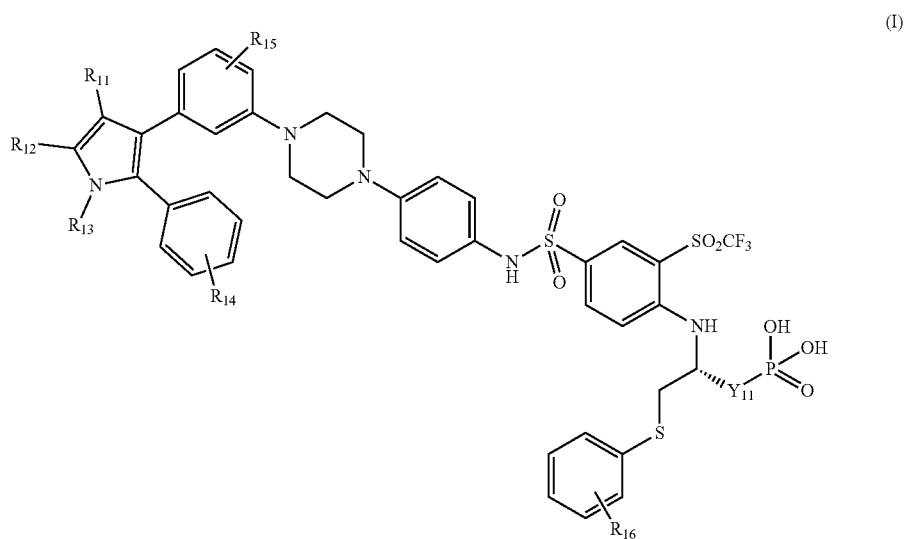

(I)

(II)
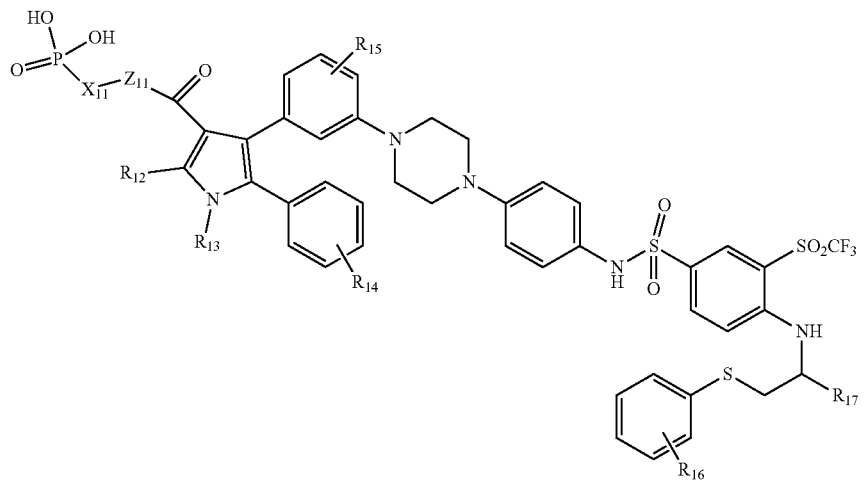
(III)
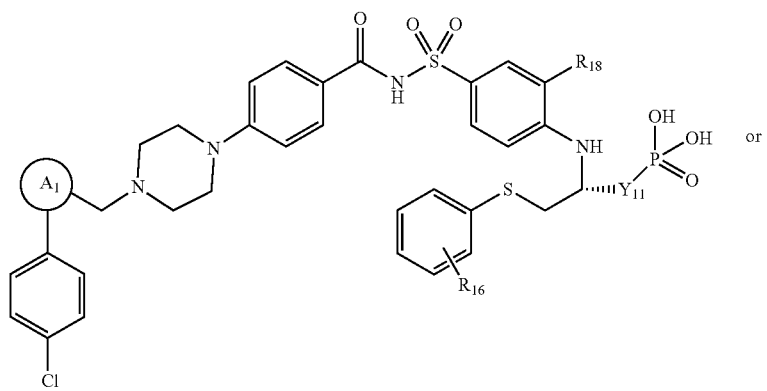
or
(IV)
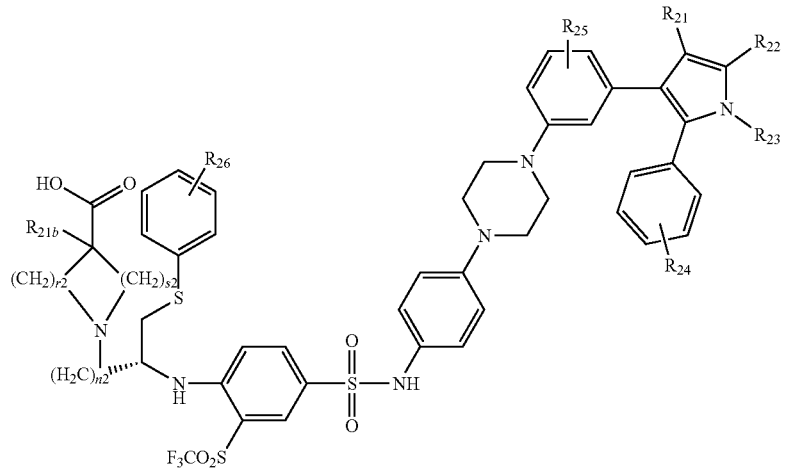

wherein:

A₁ ring is or

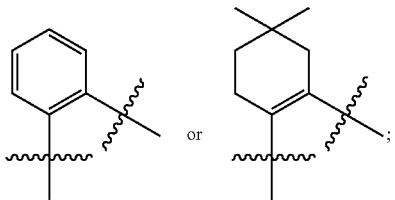

X₁₁, substituted or unsubstituted, is selected from the group consisting of alkylene, alkenylene, cycloalkylene, cycloalkenylene and heterocycloalkylene;

Y₁₁ is selected from the group consisting of (CH₂)ₙ-N(R₁₁ᵃ)₂ and

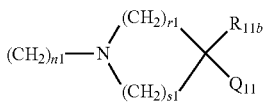

Q11 is selected from the group consisting of O, O(CH2)1-3, NR11c, NR11c(C1-3 alkylene), OC(=O)(C1-3 alkylene), C(=O)O, C(=O)O(C1-3 alkylene), NHC(=O)(C1-3 alkylene), C(=O)NH, and C(=O)NH(C1-3 alkylene);

Z11 is O or NR11c;

R11 and R12, independently, are selected from the group consisting of H, CN, NO2, halo, alkyl, cycloalkyl, alkenyl, cycloalkenyl, alkynyl, aryl, heteroaryl, heterocycloalkyl, OR1', SR1', NR1'R1", COR1', CO2R1', OCOR1', CONR1'R1", CONR1'SO2R1", NR1'COR1", NR1'CONR1"R1'", NR1'C=SNR1"R1'", NR1'SO2R1", SO2R1', and SO2NR1'R1";

R13 is selected from the group consisting of H, alkyl, cycloalkyl, alkenyl, cycloalkenyl, alkynyl, aryl, heteroaryl, heterocycloalkyl, OR1', NR1'R1", OCOR1', CO2R1', COR1', CONR1'R1", CONR1'SO2R1", C1-3 alkyleneCH(OH)CH2OH, SO2R1', and SO2NR1'R1";

R1', R1", and R1'", independently are H, alkyl, cycloalkyl, alkenyl, cycloalkenyl, alkynyl, aryl, heteroaryl, C1-3alkyleneheterocycloalkyl, or heterocycloalkyl;

R1' and R1", or R1" and R1'", can be taken together with the atom to which they are bound to form a 3 to 7-membered ring;

R14 is hydrogen, halo, C1-3 alkyl, CF3, or CN;

R15 is hydrogen, halo, C1-3 alkyl, substituted C1-3 alkyl, hydroxyalkyl, alkoxy, or substituted alkoxy;

R16 is selected from the group consisting of H, CN, NO2, halo, alkyl, cycloalkyl, alkenyl, cycloalkenyl, alkynyl, aryl, heteroaryl, heterocycloalkyl, OR1', SR1', NR1'R1", CO2R1', OCOR1', CONR1'R1", CONR1'SO2R1", NR1'COR1", NR1'CONR1"R1'", NR1'C=SNR1"R1'", NR1'SO2R1", SO2R1', and SO2NR1'R1";

R17, substituted or unsubstituted, is selected form the group consisting of hydrogen, alkyl, alkenyl, (CH2)0-3-cycloalkyl, (CH2)0-3-cycloalkenyl, (CH2)0-3-heterocycloalkyl, (CH2)0-3-aryl, and (CH2)0-3-heteroaryl;

R18 is selected form the group consisting of hydrogen, halo, NO2, CN, CF3SO2, and CF3;

R11a is selected from the group consisting of hydrogen, alkyl, heteroalkyl, alkenyl, hydroxyalkyl, alkoxy, substituted alkoxy, cycloalkyl, cycloalkenyl, and heterocycloalkyl;

R11b is hydrogen or alkyl;

R11c is selected from the group consisting of hydrogen, alkyl, substituted alkyl, hydroxyalkyl, alkoxy, and substituted alkoxy; and n1, r1, and s1, independently are 1, 2, 3, 4, 5, or 6;

R21 is SO2R2';

R22 is alkyl, preferably C1-4 alkyl, more preferably methyl, propyl, or isopropyl;

R23 is alkyl, preferably C1-4 alkyl, more preferably methyl, propyl, or isopropyl;

R24 is halogen, preferably fluoride, chloride;

R25 is halogen, preferably fluoride, chloride;

R26 is selected from H, halogen and alkyl, preferably fluoride, chloride, C1-4 alkyl, more preferably methyl, propyl, isopropyl;

R21b is H or alkyl, preferably C1-4 alkyl, more preferably methyl, propyl, or isopropyl;

n2, r2 and s2 are independently 1, 2, 3, 4, 5 or 6, more preferably, r2 and s2 are both 2 and n2 is 3, 4 or 5, more preferably, all of n2, r2 and s2 are 2, and R2' is alkyl, preferably C1-4 alkyl, more preferably methyl, propyl, or isopropyl.

In the above formula (I), (II) or (III), in some embodiments, R11 and R12 or R12 and R13 may together form a ring. In other embodiments, R1' and R1" or R1" and R1'" may form a 3-7 membered ring together with the atoms to which they are attached.

In some preferred embodiments, X11 is an alkylene group, and in other preferred embodiments, a C1-3 alkylene.

In some embodiments, Y11 is:

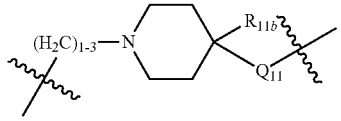

In a preferred embodiment, n1 is 2. In other preferred embodiments, R11b is hydrogen or C1-3 alkyl.

In some preferred embodiments, Q11 is O, O(CH2)1-3, C(=O)O(CH2)1-3, OC(=O)(CH2)1-3 or C(=O)O(C3H7)1-3. In other embodiments, Q11 is O, OCH2, C(=O)OCH2, C(=O)O(CH2)2, C(=O)O(CH2)3, OC(=O)CH2 or C(=O)O(CH(CH3)CH2).

In some embodiments, Z11 is O, NH or N(C1-3 alkyl). In preferred embodiments, Z11 is O, NH or NCH3.

In some embodiments, R11 is SO2R1', SO2NR1'R1", NR1'SOR1", H or alkyl. In some preferred embodiments, R11 is SO2(C1-3 alkyl), SO2N(C1-3 alkyl)2, NHSO2(C1-3 alkyl), H or C1-3 alkyl. A preferred embodiment of R11 is SO2CH3.

In some embodiments, R12 and R13 are independently H, C1-3 alkyl or cycloalkyl. R12 can also be halogen. In some preferred embodiments, R12 and R13 are independently methyl, ethyl, n-propyl, isopropyl, cyclopentyl or cyclohexyl. R12 can also be Cl or F.

In some embodiments, R14 is H or halo, preferably H, Cl or F. In other embodiments, R15 is H, halo or C1-3 alkyl, preferably H, methyl, ethyl, n-propyl, isopropyl, F or Cl. In other embodiments, R16 is H, halo, alkyl or cycloalkyl. In some preferred embodiments, R16 is H, F, Cl, C1-3 alkyl, cyclopentyl or cyclohexyl.

In some embodiments, R17 is (CH2)0-3-cycloalkyl or (CH2)0-3-heterocycloalkyl. In a preferred embodiment, R17 is (CH2)0-3-cycloalkyl, optionally substituted by —OH. In one embodiment, R17 is

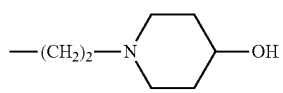
In some embodiments, R18 is CF3SO2 or CF3. In various embodiments, R11a, R11b, and R11c are, independently, H or C1-3 alkyl.
In some embodiments, the Bcl-2/Bcl-xL dual inhibitor is selected from the compounds of Table 2 below, or a pharmaceutically acceptable salt thereof, or a solvate thereof.
TABLE 2
| Cpd. No. | Structure |
|---|---|
| 58 | 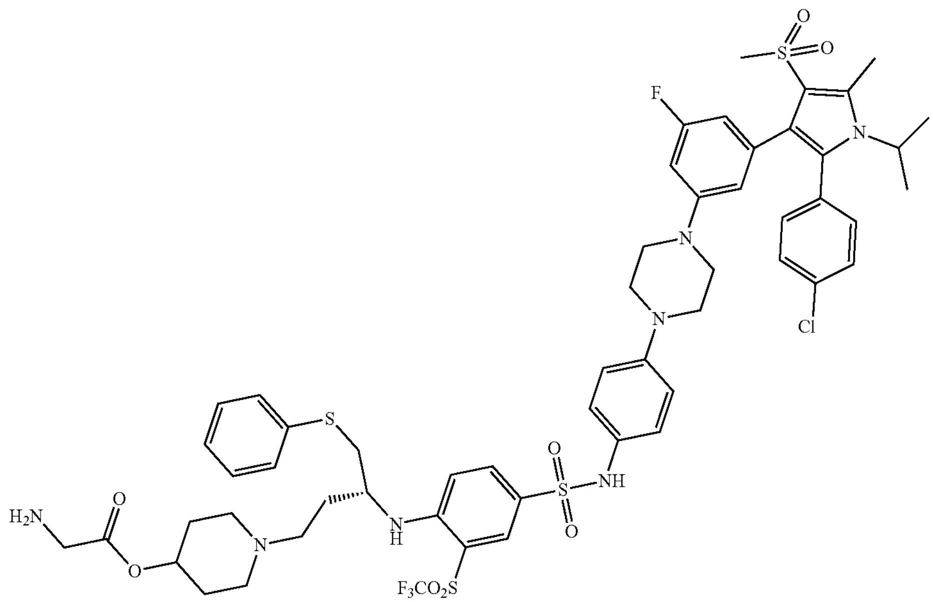 |
| 59 | 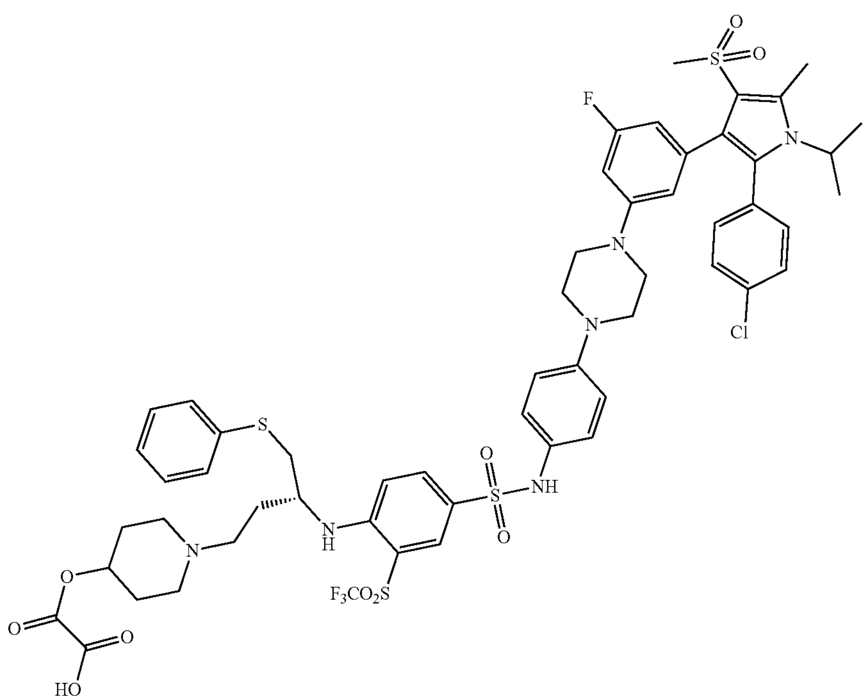 |

TABLE 2-continued
| Cpd. No. | Structure |
|---|---|
| 60 | 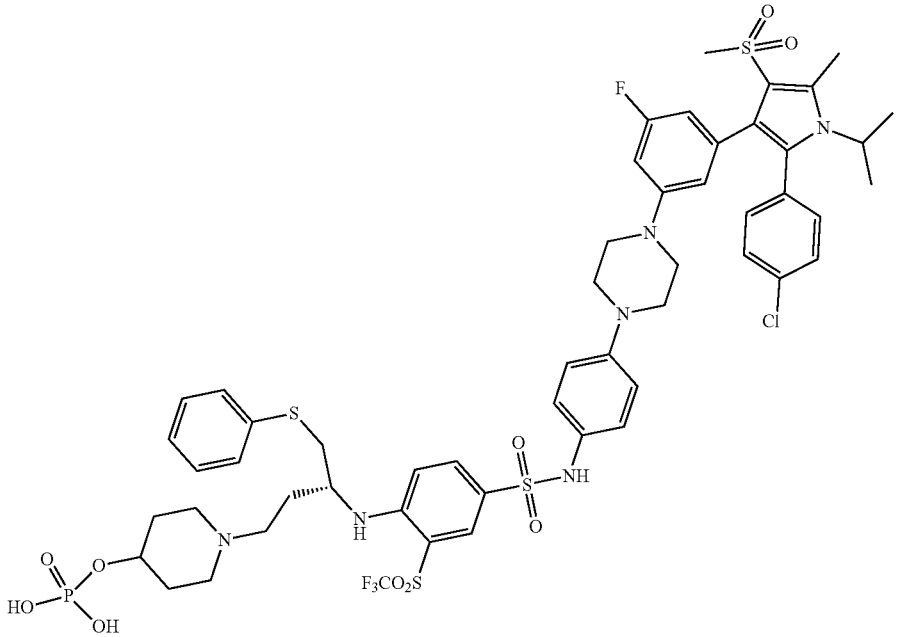 |
| 61 | 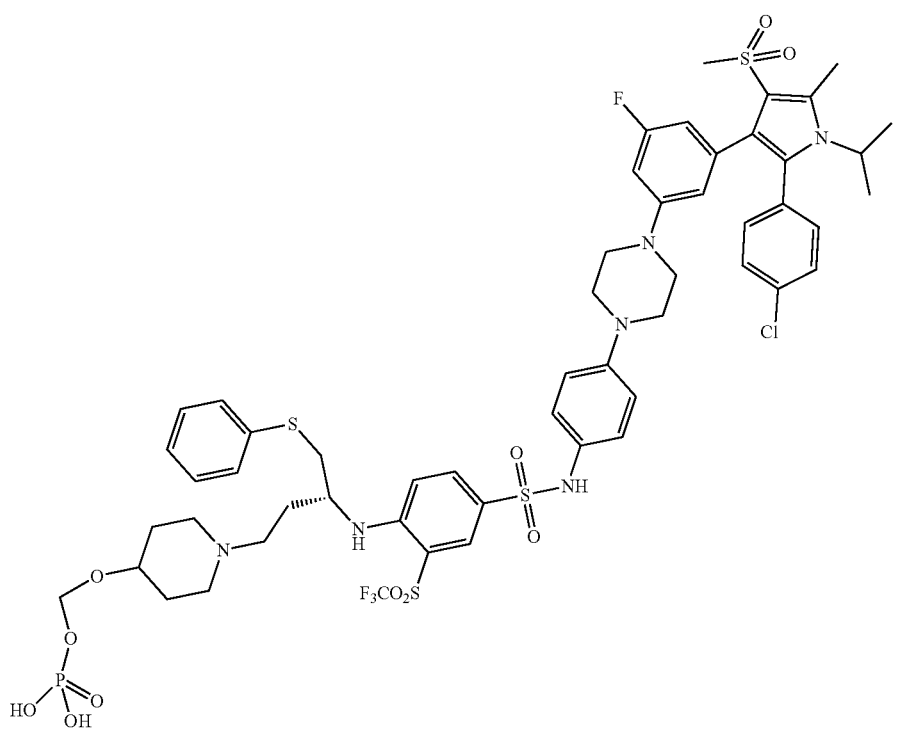 |

TABLE 2-continued

| Cpd. No. | Structure |
| --- | --- |
| 62 | 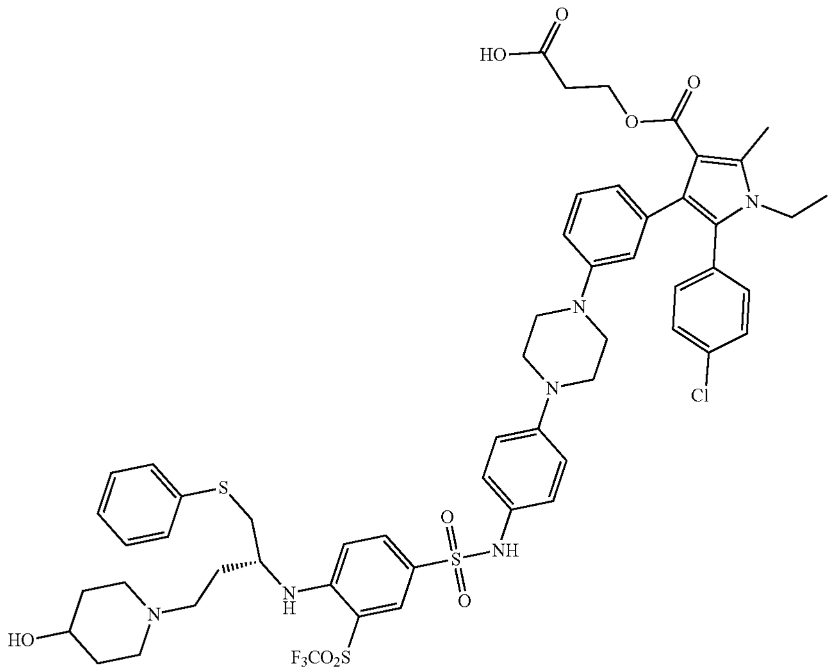 |
| 63 | 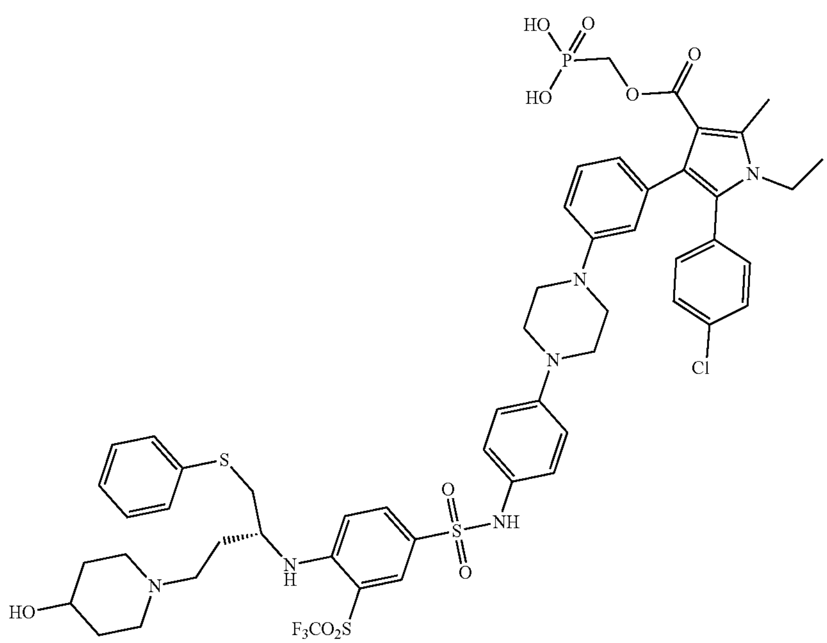 |

TABLE 2-continued
| Cpd. No. | Structure |
|---|---|
| 64 | 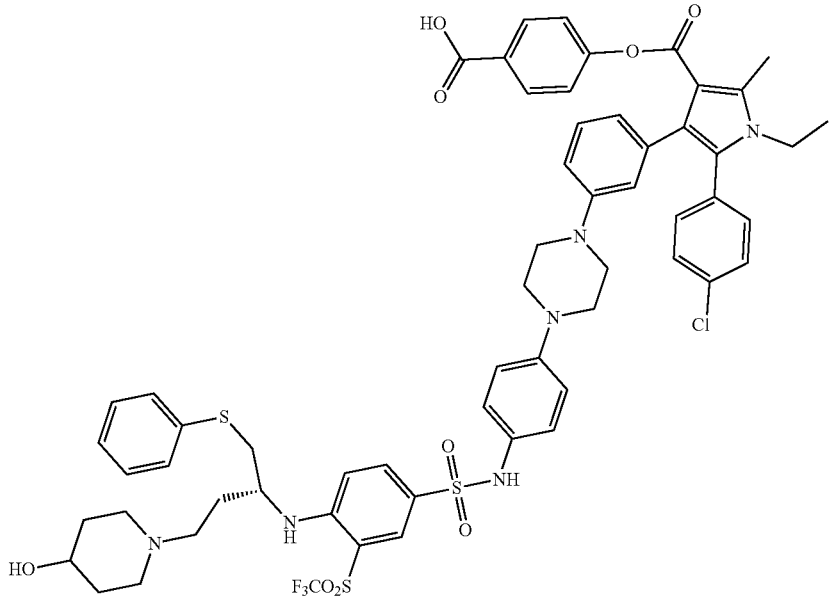 |
| 65 | 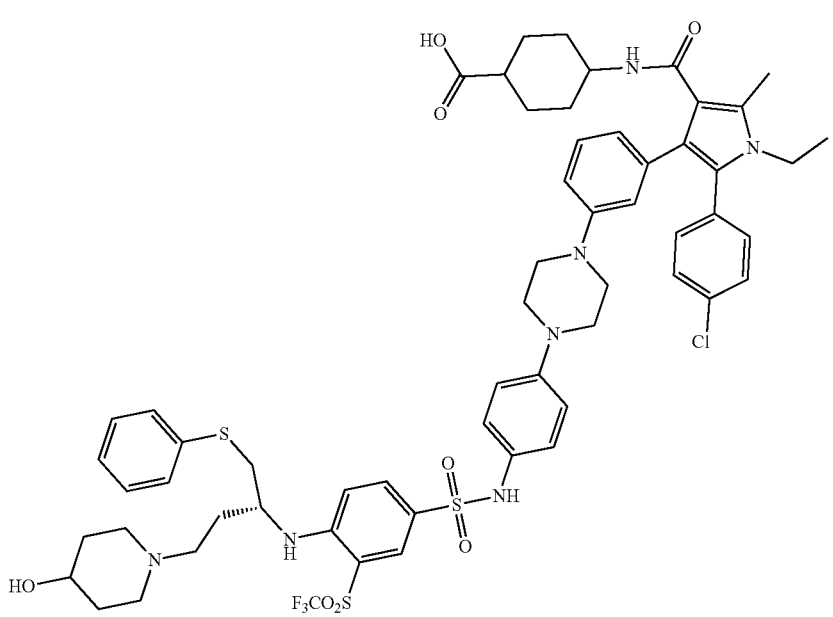 |

TABLE 2-continued
| Cpd. No. | Structure |
| --- | --- |
| 66 | 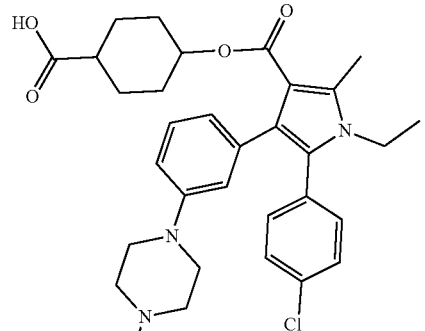 |
| 67 | 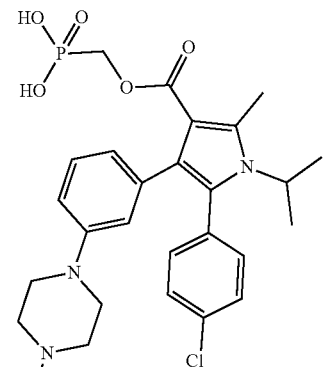 |

TABLE 2-continued
| Cpd. No. | Structure |
|---|---|
| 68 | 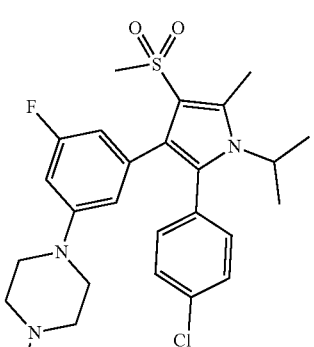 |
| 69 | 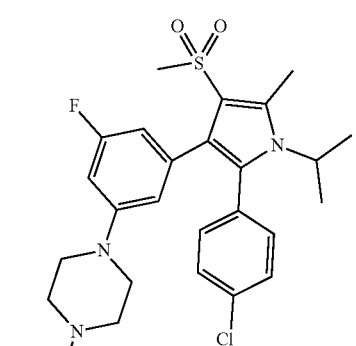 |

TABLE 2-continued
| Cpd. No. | Structure |
|---|---|
| 70 | 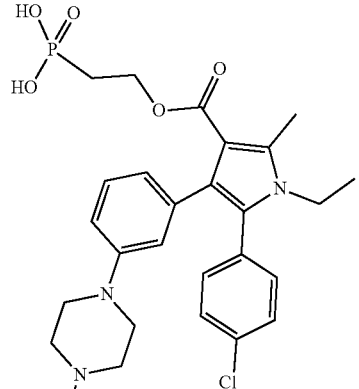 |
| 71 | 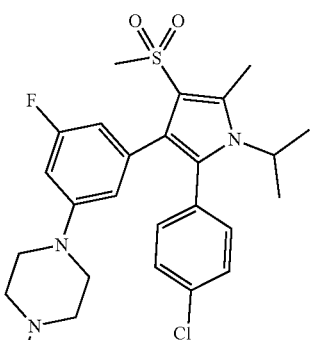 |

TABLE 2-continued
| Cpd. No. | Structure |
| --- | --- |
| 72 | 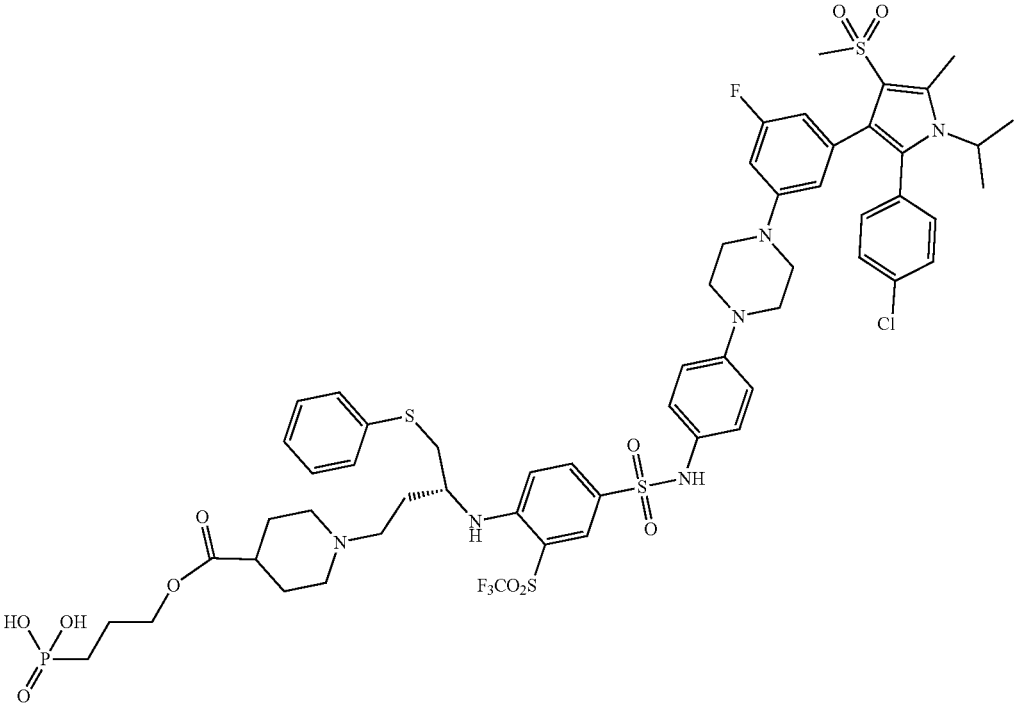 |
| 73 | 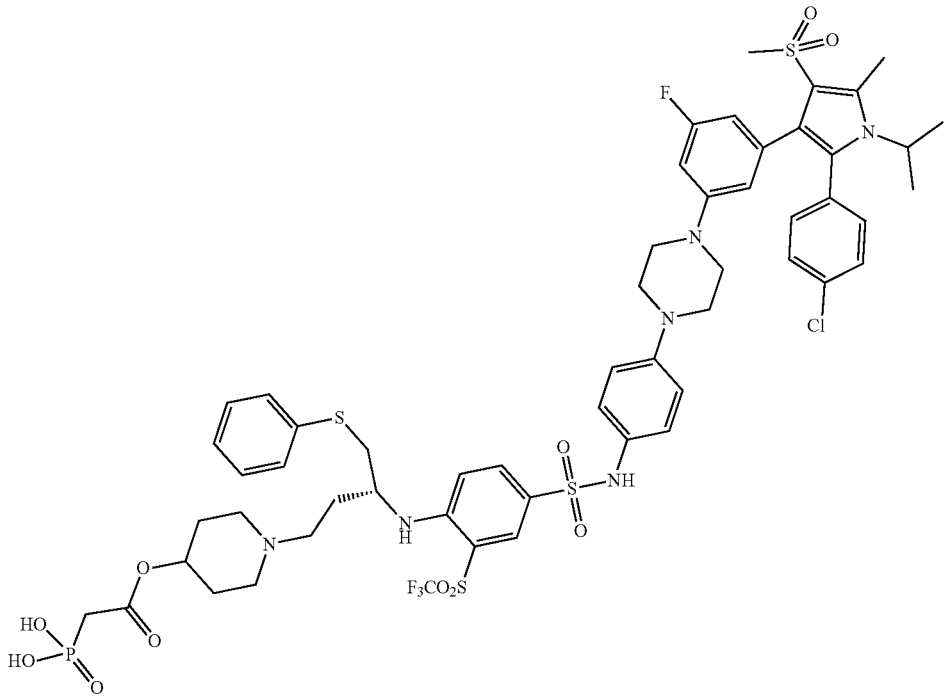 |

TABLE 2-continued
| Cpd. No. | Structure |
|---|---|
| 74 | 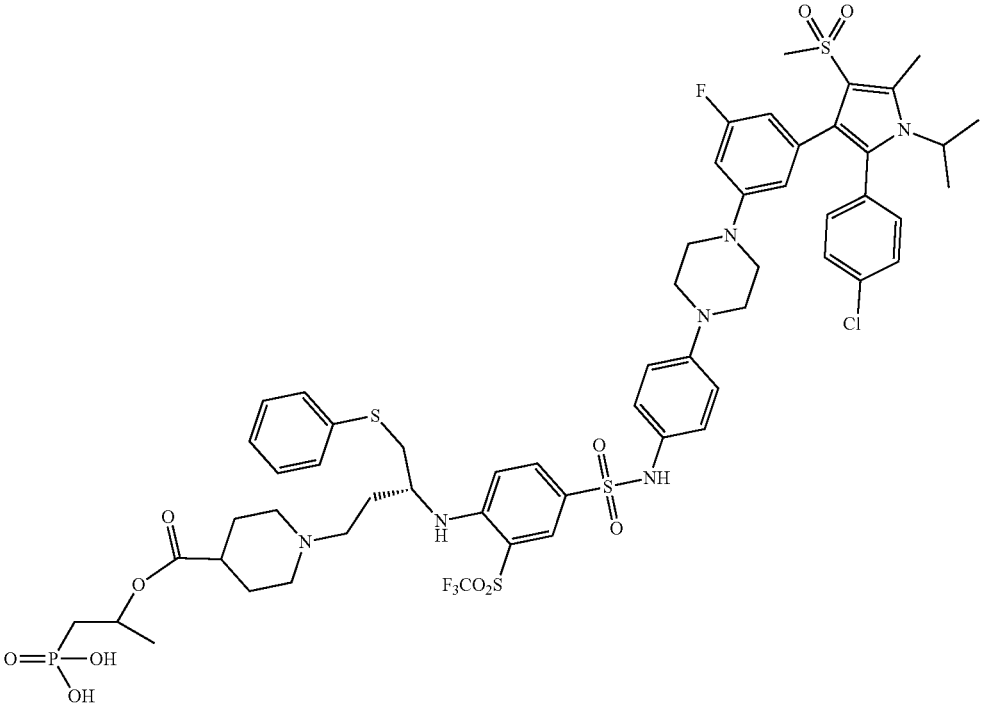 |
| 75 | 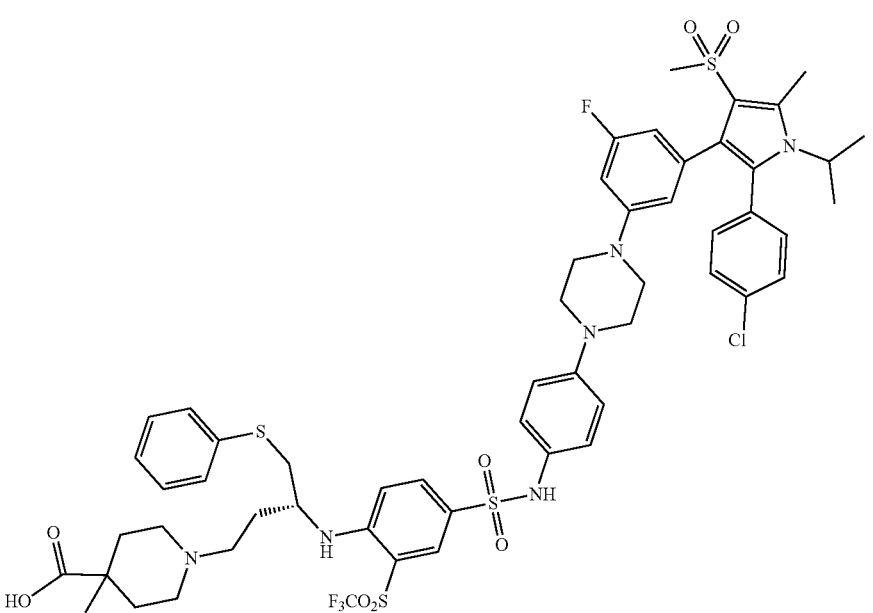 |

TABLE 2-continued
| Cpd. No. | Structure |
|---|---|
| 76 | 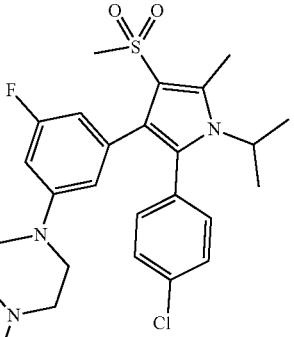 |
| 77 | 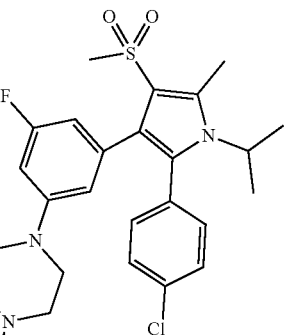 |

TABLE 2-continued
| Cpd. No. | Structure |
|---|---|
| 78 | 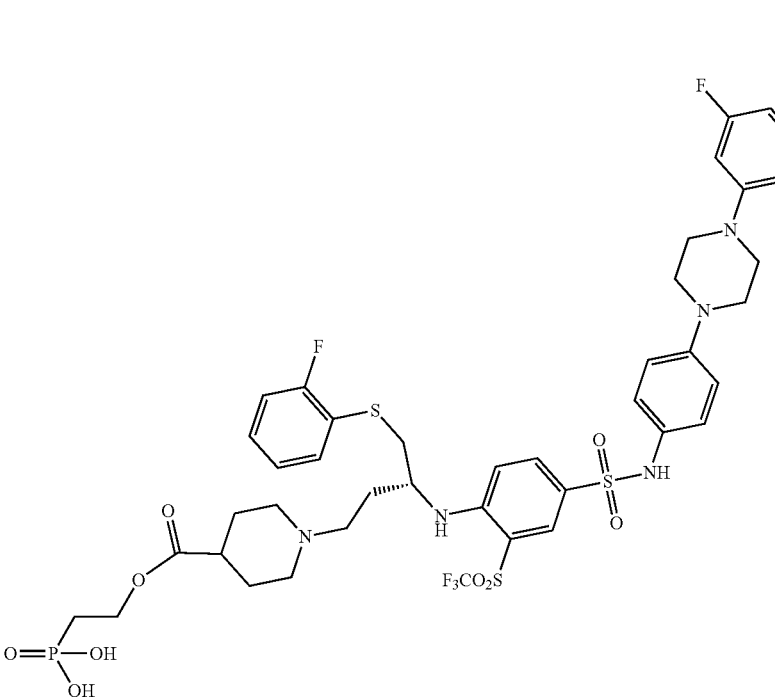 |
| 79 | 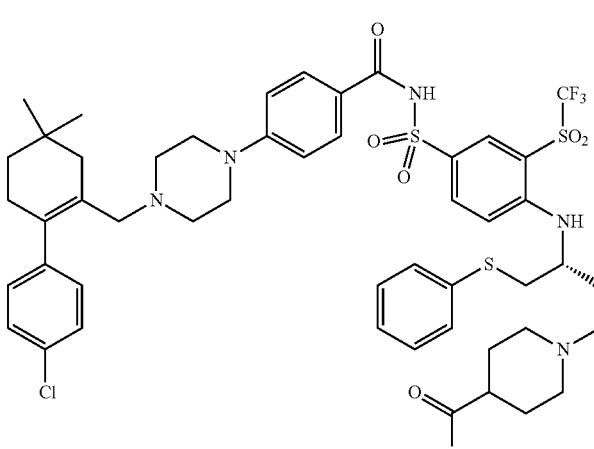 |

TABLE 2-continued

| Cpd. No. | Structure |
| --- | --- |
| 80 | 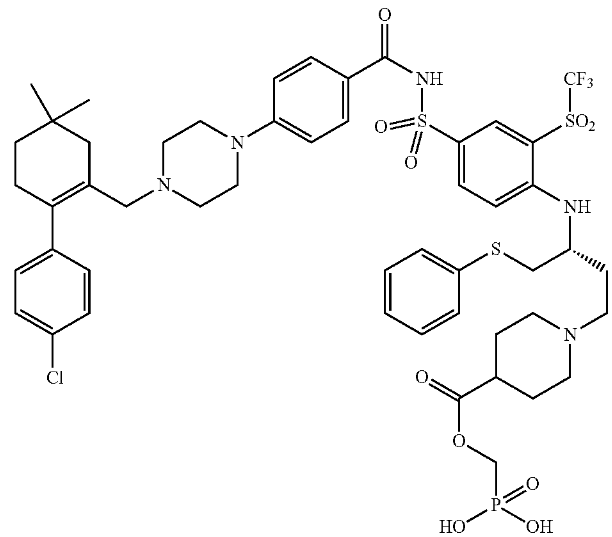 [SMILES: CC1(C)CCC(c2ccc(Cl)cc2)=C(CN2CCN(c3ccc(C(=O)NS(=O)(=O)c4ccc(N[C@H](CCN5CCC(C(=O)OCP(=O)(O)O)CC5)CSc5ccccc5)c(S(=O)(=O)C(F)(F)F)c4)cc3)CC2)C1] |
| 81 | 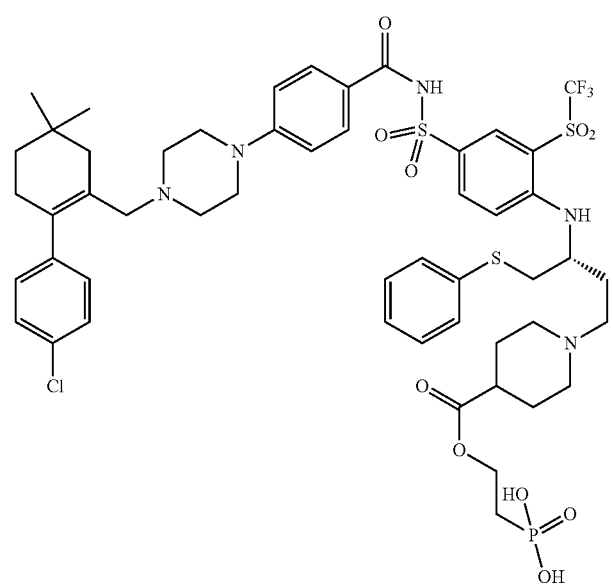 [SMILES: CC1(C)CCC(c2ccc(Cl)cc2)=C(CN2CCN(c3ccc(C(=O)NS(=O)(=O)c4ccc(N[C@H](CCN5CCC(C(=O)OCCP(=O)(O)O)CC5)CSc5ccccc5)c(S(=O)(=O)C(F)(F)F)c4)cc3)CC2)C1] |

TABLE 2-continued

| Cpd. No. | Structure |
|---|---|
| 82 | 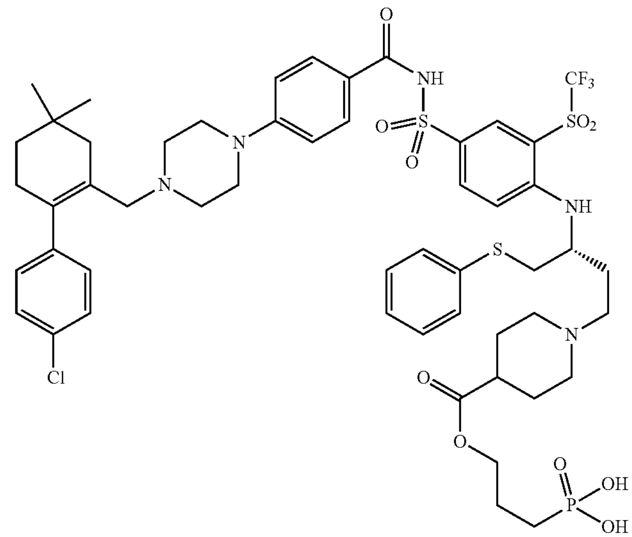 [SMILES: CC1(C)CCC(c2ccc(Cl)cc2)=C(CN2CCN(c3ccc(C(=O)NS(=O)(=O)c4ccc(N[C@H](CCN5CCC(C(=O)OCCCP(=O)(O)O)CC5)CSc5ccccc5)c(S(=O)(=O)C(F)(F)F)c4)cc3)CC2)C1] |
| 83 | 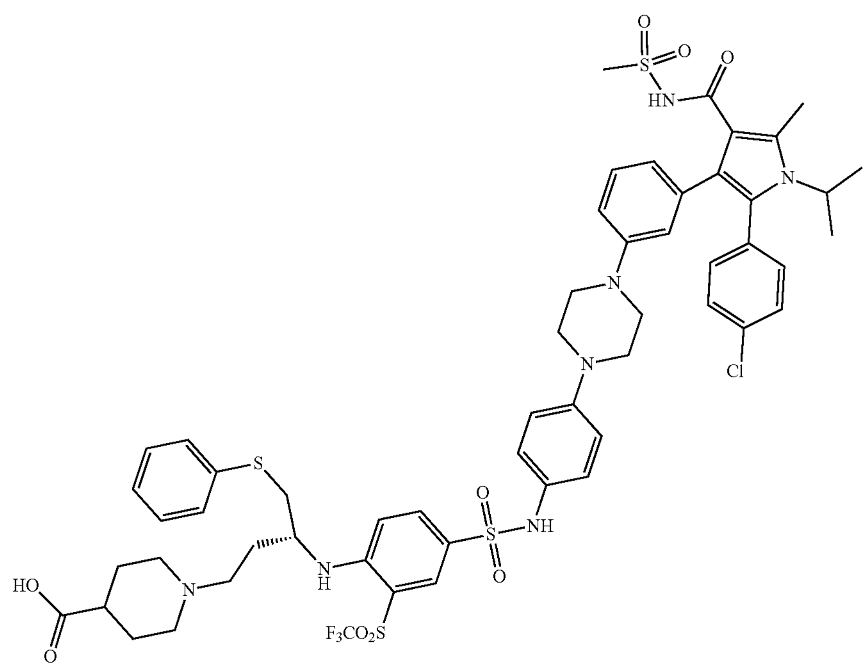 |

| Cpd. No. | Structure |
|---|---|
| 84 | 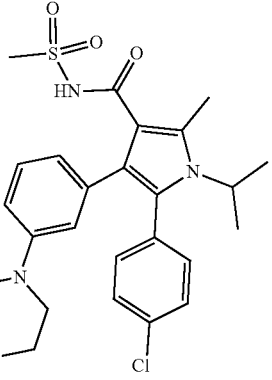 |
| 85 | 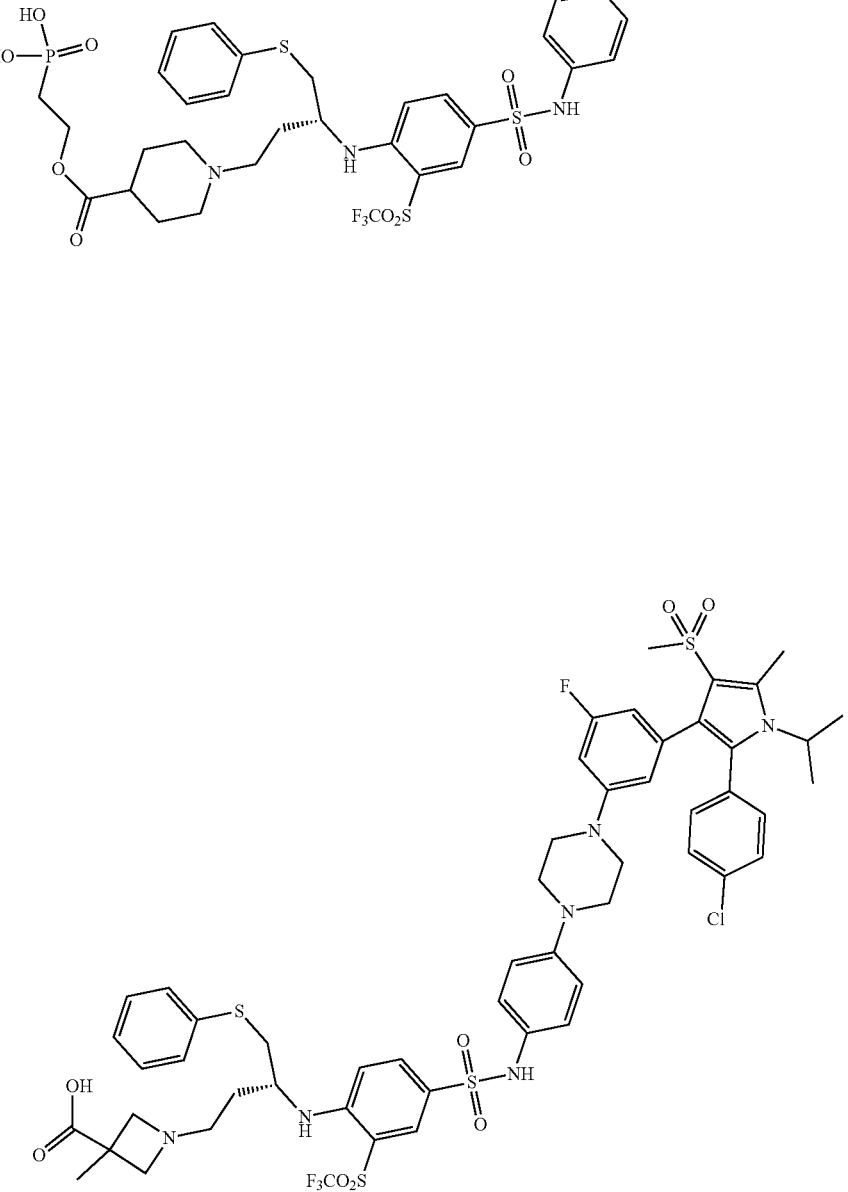 |

TABLE 2-continued
| Cpd. No. | Structure |
|---|---|
| 86 | 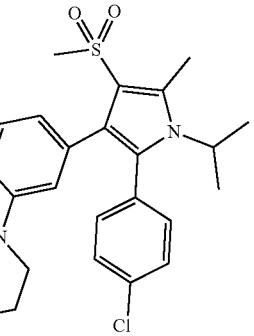 |
| 87 | 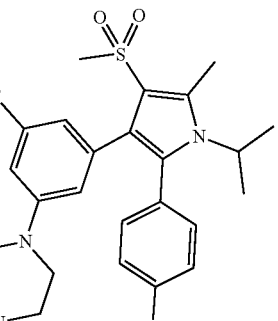 |

TABLE 2-continued
| Cpd. No. | Structure |
|---|---|
| 88 | 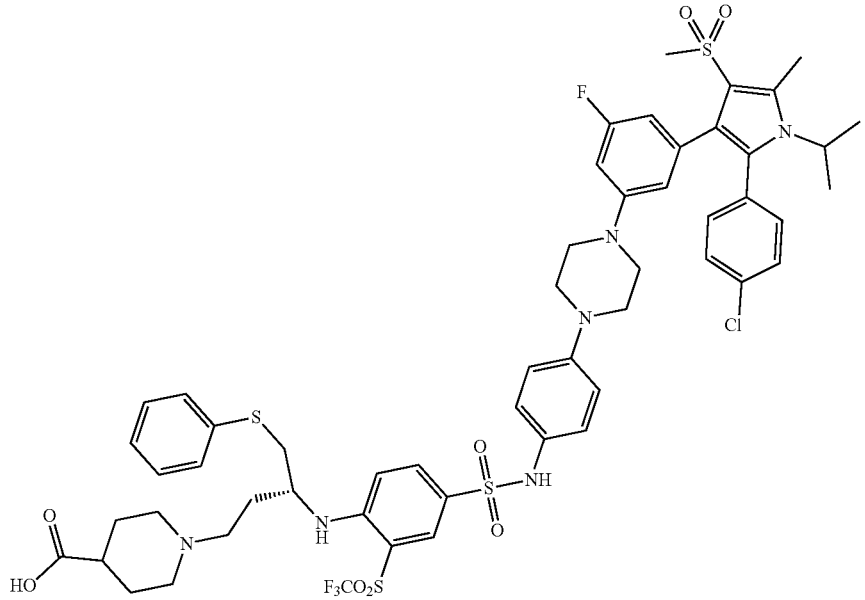 |
| 89 | 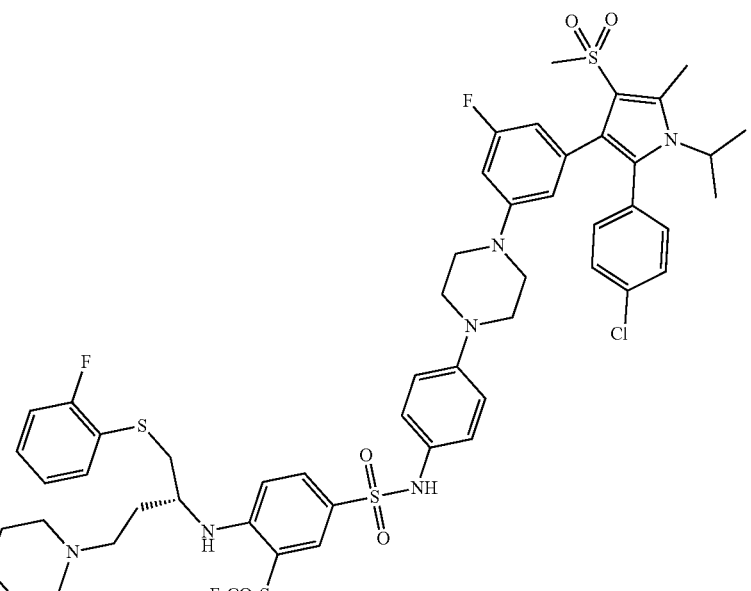 |

121
122
TABLE 2-continued
| Cpd. No. | Structure |
|---|---|
| 90 | 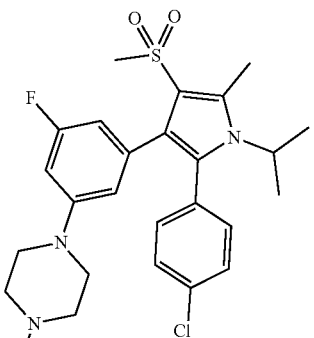 |
| 91 | 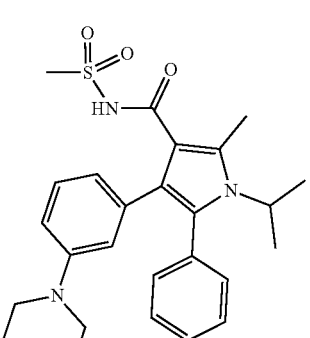 |

| Cpd. No. | Structure |
|---|---|
| 92 | 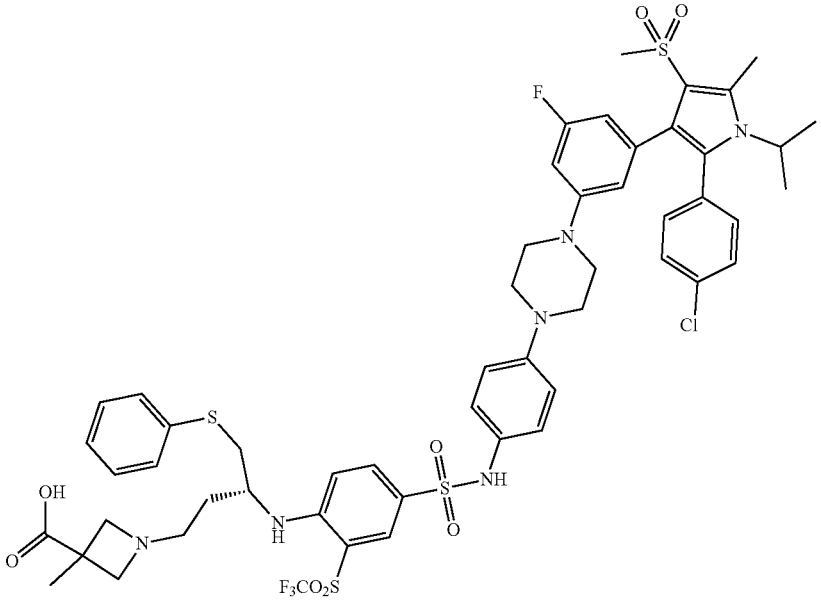 |

In some embodiments, the Bcl-2/Bcl-xL dual inhibitor is (R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl) piperidine-4-carbonyloxy)ethylphosphonic acid (i.e. Compound 72 in the above table, sometimes abbreviated as "Compound 72") or a pharmaceutically acceptable salt thereof, as shown in the following structural formula:

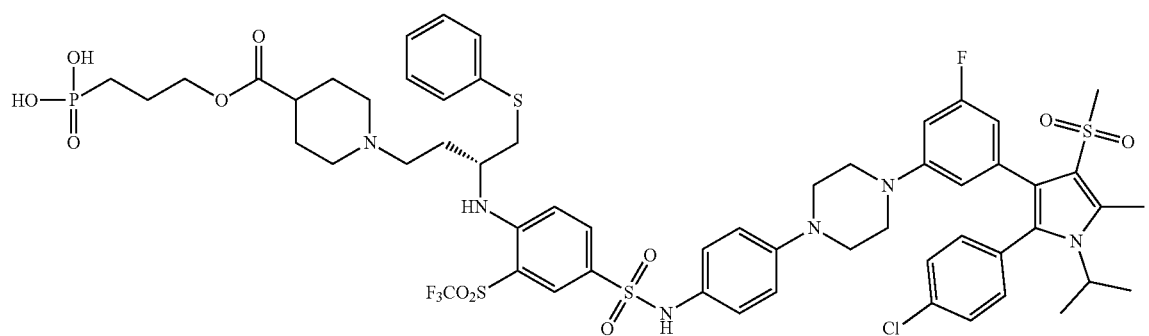

Compound 72 selectively binds to Bcl-2, Bcl-xL, and Bcl-w proteins with high affinity, and the $IC_{50}$ is 1.6 nM, 4.4 nM, and 9.3 nM, respectively. Compound 72 binds weakly to Mcl-1. Compound 72, by chemical structural modification, effectively reduces platelet toxicity defects in first-generation BCL-2 inhibitors in the blood circulation, yet is capable of obtaining specific enzyme activation in tissues to effectively kill tumor cells. Its platelet toxicity is reduced by 10-30 times, but the activity is about 10 times that of the first generation BCL-2 inhibitors. Compound 88 is an active metabolite of Compound 72. Compound 72 is a second generation new target BCL-2 protein inhibitor.

The Bcl-2/Bcl-xL dual inhibitor of the present invention may also preferably be (R)-1-(3-(4-(N-(4-(4-(3-(2-(4-chlorophenyl))-1-isopropyl-5-methyl-4-(methylsulfonyl)-1H-pyrrol-3-yl)-5-fluorophenyl)piperazin-1-yl)phenyl)-sulfamoyl-2-(trifluoromethylsulfonyl)phenylamino)-4-(phenylthio)butyl)piperidine-4-carboxylic acid (i.e., Compound 88 in the above table, sometimes abbreviated as "Compound 88"), or a pharmaceutically acceptable salt thereof, represented by the following structural formula:

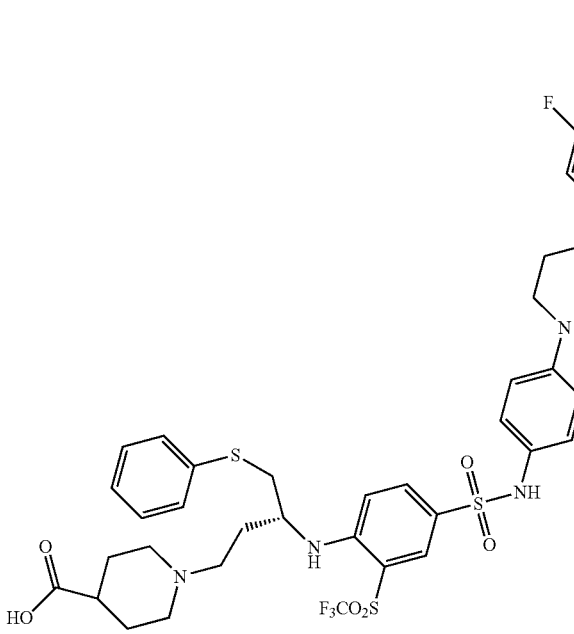

The above Bcl-2/Bcl-xL dual inhibitor in the pharmaceutical composition of the present invention can be synthesized according to the method described in WO2014/113413A1.

Compounds of the above formula (I), (II) or (III) have been disclosed in WO2014/113413A1, which is incorporated herein by reference to its entirety. The above general formula (IV) is disclosed in PCT/CN2019/070508, which is incorporated herein by reference to its entirety.

In some embodiments, the BTK inhibitor is selected from the group consisting of: Ibrutinib, ICP-022, Acalabrutinib (ACP-196), BGB3111, ONO/GS-4059, Spebrutinib (CC-292 or AVL-292), CNX-774, Olmutinib (HM61713, B11482694), M7583, HM71224, PCI-32765 Racemate, GDC-0853, ONO-4059, Zanubrutinib, RN486, PCI-32765, CGI-1746, QL47, LFM-A13, (±)-Zanubrutinib, SNS-062, BMS-935177, Btk inhibitor 2, Evobrutinib, Ibrutinib-biotin, BMX-IN-1, GDC-0834 and CB1763. Preferably, the BTK inhibitor is selected from the group consisting of: Ibrutinib, Acalabrutinib (ACP-196) and BGB3111. More preferably, the BTK inhibitor is Ibrutinib having the following structure:

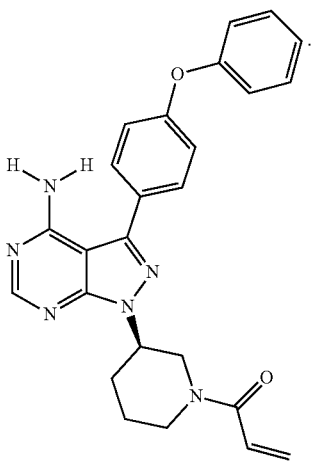 [SMILES: C=CC(=O)N1CCC[C@@H](n2nc(-c3ccc(Oc4ccccc4)cc3)c3c(N)ncnc32)C1]

In some embodiments, the combination product is in the form of a pharmaceutical composition.

In some embodiments, the Bcl-2 inhibitor and the BTK inhibitor are each in a separate preparation, or the Bcl-2/Bcl-xL dual inhibitor and the BTK inhibitor are each in a separate preparation.

In some embodiments, the Bcl-2 inhibitor and the BTK inhibitor are administered simultaneously or sequentially, or the Bcl-2/Bcl-xL dual inhibitor and the BTK inhibitor are administered simultaneously or sequentially.

In some embodiments, the Bcl-2 inhibitor or the Bcl-2/Bcl-xL dual inhibitor and the BTK inhibitor may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, About 5 weeks, about 6 weeks, about 8 weeks, or about 12 weeks.

In some embodiments, the combination product of the invention comprising the Bcl-2 inhibitor or the Bcl-2/Bcl-xL dual inhibitor and the BTK inhibitor in the form of a pharmaceutical composition (preferably, each in a separate dosage unit form), as desired, can be daily administered for, including but not limited to: 1 time, 2 times, 3 times, 4 times, 5 times or 6 times.

In some embodiments, the combination product of the invention comprising the Bcl-2 inhibitor or the Bcl-2/Bcl-xL dual inhibitor and the BTK inhibitor in the form of a pharmaceutical composition (preferably, in the form of a dosage unit), as desired, can be daily administered for, including but not limited to: 1 time, 2 times, 3 times, 4 times, 5 times or 6 times.

In some embodiments, the combination product can be administered in the following manner: oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor or a pharmaceutically acceptable salt or solvate thereof is administered in an amount of from about 0.0025 to 1500 mg/day. Preferably, the daily dose of the Bcl-2 inhibitor is 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 460 mg, 470 mg, 480 mg, 487 mg, 490 mg, 500 mg, 550 mg, 600 mg, 650 mg, 700 mg, 750 mg, 800 mg, 850 mg, 900 mg, 950 mg, 1000 mg, and a range between the respective doses, for example, 1 mg to 1000 mg, 30 mg to 900 mg, 30 mg to 800 mg, 30 mg to 900 mg, 30 mg to 800 mg, 30 mg to 700 mg, 30 mg to 600 mg, 30 mg to 500 mg, 30 mg to 490 mg, 30 mg to 487 mg, etc., and the BTK inhibitor or a pharmaceutically acceptable salt or solvate thereof is administered in an amount of about 0.0025 to 1000 mg/day. Preferably, the daily dose of the BTK inhibitor is 10 mg, 20 mg, 30 mg, 40 mg, 50 mg, 60 mg, 70 mg, 73 mg, 80 mg, 90 mg, 97.6 mg, 100 mg, 122 mg, 150 mg, 200 mg, 250 mg, 300 mg, 350 mg, 400 mg, 450 mg, 460 mg, 470 mg, 480 mg, 487 mg, 490 mg, 500 mg, 550 mg, 600 mg, 650 mg, 700 mg, 750 mg, 800 mg, 850 mg, 900 mg, 950 mg, 1000 mg, and a range between the respective doses, for example, 10 mg to 1000 mg, 20 mg to 950 mg, 30 mg to 900 mg, 50 mg to 650 mg, 60 mg to 600 mg, 70 mg to 450 mg, 73 mg to 400 mg, 73 mg to 550 mg, 73 mg to 522 mg, 97.6 mg to 600 mg, 97.6 mg to 600 mg, 97.6 mg to 700 mg, 97.6 mg to 800 mg, 97.6 mg to 950 mg, 122 mg to 500 mg, 122 mg to 600 mg, 122 mg to 700 mg, 122 mg to 800 mg, 97.6 mg to 900 mg, 73 mg to 1000 mg, and the like.

In certain embodiments, the Bcl-2/Bcl-xL dual inhibitor may be administered in an amount of from about 0.005 to about 500 mg/day, preferably from about 0.05 to about 250 mg/day, more preferably from about 0.5 to about 100 mg/day. In certain embodiments, the Bcl-2/Bcl-xL dual inhibitor is administered in an amount of from about 10 mg/week to about 1000 mg/week, from about 10 mg/week to about 900 mg/week, from about 10 mg/week to about 800 mg/Week, about 10 mg/week to about 700 mg/week, about 10 mg/week to about 640 mg/week, about 10 mg/week to about 600 mg/week, about 10 mg/week to about 500 mg/week, about 10 mg/Weekly to about 400 mg/week, about 10 mg/week to about 300 mg/week, about 10 mg/week to about 200 mg/week, or about 20 mg/week to about 100 mg/week, for example about 10, 15, 20, 25, 30, 35, 40, 50, 55, 60, 65, 70, 75, 80, 85, 90, 95, 100, 150, 200, 250, 300, 350, 400, 450, 500, 550, 600, 650, 700, 750, 800, 850, 900, 950, 1000 mg/week, and the BTK inhibitor or a pharmaceutically acceptable salt or solvate thereof is administered in an amount of from about 0.0025 to 1000 mg per day. In certain embodiments, the Bcl-2/Bcl-xL dual inhibitor is about 0.005, 0.05, 0.5, 5, 10, 20, 30, 40, 50, 100, 150, 200, 250, 300, 350, 400, 450 or 500 mg. In certain embodiments, the Bcl-2/Bcl-xL dual inhibitor is administered at a frequency of once a week, twice a week, three times a week, four times a week, five times a week, six times a week, seven times a week.

Preferably, the daily dose of the BTK inhibitor is 10 mg, 20 mg, 30 mg, 40 mg, 50 mg, 60 mg, 70 mg, 73 mg, 80 mg, 90 mg, 97.6 mg, 100 mg, 122 mg, 150 mg, 200 mg, 250 mg, 300 mg, 350 mg, 400 mg, 450 mg, 460 mg, 470 mg, 480 mg, 487 mg, 490 mg, 500 mg, 550 mg, 600 mg, 650 mg, 700 mg, 750 mg, 800 mg, 850 mg, 900 mg, 950 mg, 1000 mg, and a range between the respective doses, for example, 10 mg-1000 mg, 20 mg-950 mg, 30 mg-900 mg, 50 mg-650 mg, 60 mg-600 mg, 70 mg-450 mg, 73 mg-400 mg, 73 mg-550 mg, 73 mg-522 mg, 97.6 mg-600 mg, 97.6 mg-600 mg, 97.6 mg-700 mg 97.6 mg-800 mg, 97.6 mg-950 mg, 122 mg-500 mg, 122 mg-600 mg, 122 mg-700 mg, 122 mg-800 mg, 97.6 mg-900 mg, 73 mg-1000 mg, and the like.

In some embodiments, the combination product further comprises a pharmaceutically acceptable carrier, diluent or excipient.

In some embodiments, the combination product is in the form of tablet, capsule, granule, syrup, powder, lozenge, sachet, cachet, elixir, suspension, emulsion, solution, syrup, aerosol, ointment, cream and injection.

A second aspect of the invention relates to the use of a Bcl-2 inhibitor or a Bcl-2/Bcl-xL dual inhibitor and a BTK inhibitor in the manufacture of a medicament for the prevention and/or treatment of a disease selected from the group consisting of cancer, autoimmune disease and inflammatory disease. In some embodiments, the disease is refractory or is resistant to BTK inhibitors. In certain embodiments, the disease is refractory or is resistant to ibrutinib.

In some embodiments, the Bcl-2 inhibitor is a compound (e.g, Compound I-A, Compound I-b, Compound I-c, Compound I-d, Compound I-e, Compound I-f, Compound I-g, Compound I-h, Compound I-i), or a pharmaceutically acceptable salt or solvate thereof, as specifically described in the first aspect of the invention.

In some embodiments, the Bcl-2/Bcl-xL dual inhibitor is a compound (e.g., Compound I, II, III, or IV) as specifically described in the first aspect of the invention, or a pharmaceutically acceptable salt or solvate thereof. In some embodiments, the Bcl-2/Bcl-xL dual inhibitor is Compound 72 or Compound 88.

In some embodiments, the BTK inhibitor is selected from the group consisting of: Ibrutinib, ICP-022, Acalabrutinib (ACP-196), BGB3111, ONO/GS-4059, Spebrutinib (CC-292 or AVL-292), CNX-774, Olmutinib (HM61713, B11482694), M7583, HM71224, PCI-32765 Racemate, GDC-0853, ONO-4059, Zanubrutinib, RN486, PCI-32765, CGI-1746, QL47, LFM-A13, (±)-Zanubrutinib, SNS-062, BMS-935177, Btk inhibitor 2, Evobrutinib, Ibrutinib-biotin, BMX-IN-1, GDC-0834 and CB1763. Preferably, the BTK inhibitor is selected from the group consisting of: Ibrutinib, Acalabrutinib (ACP-196) and BGB3111. More preferably, the BTK inhibitor is Ibrutinib.

In some embodiments, the medicament is in the form of a pharmaceutical composition.

In some embodiments, the Bcl-2 inhibitor and the BTK inhibitor are each in a separate preparation, or the Bcl-2/Bcl-xL dual inhibitor and the BTK inhibitor are each in a separate preparation.

In some embodiments, the Bcl-2 inhibitor and the BTK inhibitor are administered simultaneously or sequentially, or the Bcl-2/Bcl-xL dual inhibitor and the BTK inhibitor are administered simultaneously or sequentially.

In some embodiments, the Bcl-2 inhibitor or the Bcl-2/Bcl-xL dual inhibitor and the BTK inhibitor may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, About 5 weeks, about 6 weeks, about 8 weeks, or about 12 weeks.

In some embodiments, the medicament of the invention comprising the Bcl-2 inhibitor or the Bcl-2/Bcl-xL dual inhibitor and the BTK inhibitor in the form of a pharmaceutical composition (preferably, each in a separate dosage unit form), as desired, can be daily administered for, including but not limited to: 1 time, 2 times, 3 times, 4 times, 5 times or 6 times.

In some embodiments, the medicament of the invention comprising the Bcl-2 inhibitor or the Bcl-2/Bcl-xL dual inhibitor and the BTK inhibitor in the form of a pharmaceutical composition (preferably, in the form of a dosage unit), as desired, can be daily administered for, including but not limited to: 1 time, 2 times, 3 times, 4 times, 5 times or 6 times.

In some embodiments, the medicament can be administered in the following manner: oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor or the Bcl-2/Bcl-xL dual inhibitor or a pharmaceutically acceptable salt or solvate thereof, and the BTK inhibitor or a pharmaceutically acceptable salt or solvate thereof, are administered in a daily dose as described in the first aspect of the invention in the above detailed description of the invention.

In some embodiments, the disease is cancer. In some embodiments, the cancer is refractory or is resistant to a BTK inhibitor. In certain embodiments, the cancer is refractory or is resistant to ibrutinib.

Further, the cancer described in the present invention includes, but is not limited to, a cancer selected from the group consisting of: adrenal cancer, lymphoid epithelioma, acinic cell carcinoma, lymphoma, acoustic neuroma, acute lymphocytic leukemia, acral lentiginous melanoma, acute myelogeous leukemia, acrospiroma, chronic lymphocytic leukemia, acute eosinophilic leukemia, liver cancer, acute erythroid leukemia, small cell lung cancer, acute lymphoblastic leukemia, non-small cell lung cancer, acute megakaryoblastic leukemia, MALT lymphoma, acute monocytic leukemia, malignant fibrous histiocytoma, acute promyelocytic leukemia, malignant peripheral schwannomas, adenocarcinoma, malignant triton tumor, adenoid cystic carcinoma, mantle cell lymphoma, adenoma, marginal zone B cell lymphoma, adenomatoid odontogenic tumor, mast cell leukemia, adenosquamous carcinoma, mediastinal germ cell tumor, adipose tissue neoplasm, medullary carcinoma of the breast, adrenal cortical carcinoma, medullary thyroid carcinoma, adult T-cell leukemia/lymphoma, medulloblastoma, aggressive NK cell leukemia, melanoma, AIDS-related lymphoma, meningiomas, alveolar rhabdomyosarcoma, merkel cell carcinoma, alveolar soft tissue sarcoma, mesothelioma, ameloblastic fibroma, metastatic urothelial carcinoma, anaplastic large cell lymphoma, mixed mullerian tumor, anaplastic thyroid cancer, mucinous tumor, angioimmunoblastic T-cell lymphoma, multiple myeloma, angiomyolipoma, muscle tissue neoplasm, angiosarcoma, mycosis fungoides, astrocytoma, myxoid liposarcoma, atypical malformation rhabdoid tumor, myxoma, B cell chronic lymphocytic leukemia, myxosarcoma, B-cell prolymphocytic leukemia, nasopharyngeal carcinoma, B-cell lymphoma, neurinoma, basal cell carcinoma, neuroblastoma, biliary tract cancer, neurofibromatosis, bladder cancer, neuroma, blastoma, nodular melanoma, bone cancer, ocular cancer, Brenner tumor, oligodendroglioma, brown tumor, oligodendroglioma, Burkitt's lymphoma, oncocytoma, breast cancer, optic nerve sheath meningioma, brain cancer, optic nerve tumor, carcinoma, oral carcinoma, carcinoma in situ, osteosarcoma, carcinosarcoma, ovarian cancer, cartilage tumor, pancoast tumor, cementoma, papillary thyroid carcinoma, myeloid sarcoma, paraganglioma, chondroma, pinealoblastoma, chordoma, pinealocytoma, choriocarcinoma, pituitary tumor, choroid plexus papilloma, pituitary adenoma, clear-cell sarcoma of the kidney, pituitary tumor, craniopharyngioma, plasmacytoma, cutaneous T-cell lymphoma, polyembryoma, cervical cancer, precursor T lymphoblastic lymphoma, colorectal cancer, primary central nervous system lymphoma, Degos' disease, primary effusion lymphoma, desmoplastic small round cell tumor, primary peritoneal cancer, diffuse large B-cell lymphoma, prostate cancer, dysembryoplastic neuroepithelial tumor, pancreatic cancer, dysgerminoma, pharyngeal carcinoma, embryonal carcinoma, peritoneal pseudomyxoma, endocrine gland tumor, renal cell carcinoma, endodermal sinus tumor, renal medullary carcinoma, enteropathy-associated T-cell lymphoma, retinoblastoma, esophageal cancer, rhabdomyomas, fetus-in-fetus, rhabdomyosarcoma, fibroma, Richter's transformation, fibrosarcoma, rectal cancer, follicular lymphoma, sarcoma, follicular thyroid cancer, schwannomatosis, ganglioneuroma, seminoma, gastrointestinal cancer, sertoli cell tumor, germ cell tumor, sex cord-gonadal stromal tumor, gestational choriocarcinoma, signet ring cell carcinoma, giant cell fibroblastoma, skin cancer, giant cell tumor of bone, small blue round cell tumor, glial tumor, small cell carcinoma, glioblastoma multiforme, soft tissue sarcoma, glioma, somatostatinoma, gliomatosis cerebri, soot wart, glucagonoma, spinal tumor, gonadoblastoma, splenic marginal zone lymphoma, granulosa cell tumor, squamous cell carcinoma, gynandroblastoma, synovial sarcoma, gallbladder carcinoma, Sezary disease, gastric cancer, small intestine cancer, hairy cell leukemia, squamous cell carcinoma, hemangioblastoma, stomach cancer, head and neck cancer, T-cell lymphoma, hemangiopericytoma, testicular cancer, hematological malignancy, hepatoblastoma, thyroid cancer, hepatosplenic T-cell lymphoma, transitional cell carcinoma, Hodgkin's lymphoma, throat cancer, non-Hodgkin's lymphoma, urachal carcinoma, invasive lobular carcinoma, urogenital cancer, intestinal cancer, urothelial carcinoma, kidney cancer, uveal melanoma, laryngeal cancer, uterine cancer, lentigo maligna, verrucous carcinoma, lethal midline carcinoma, visual pathway glioma, leukemia, vulvar cancer, testicular stromal tumor, vaginal cancer, liposarcoma, Waldenstrom's macroglobulinemia (WM), lung cancer, adenolymphoma, lymphangioma, nephroblastoma and lymphangiosarcoma.

Preferably, the cancer is selected from the group consisting of: acute monocytic leukemia, acute myeloid leukemia, chronic myelogenous leukemia, chronic lymphocytic leukemia and mixed lineage leukemia, NUT midline cancer, multiple myeloma, small cell lung cancer, neuroblastoma, Burkitt's lymphoma, cervical cancer, esophageal cancer, ovarian cancer, colorectal cancer, prostate cancer and breast cancer.

Preferably, the cancer is a hematological malignancy.

More preferably, the hematological malignancy is selected from the group consisting of acute myeloid leukemia (AML), acute lymphoblastic leukemia (ALL), diffuse large B-cell lymphoma (DLBCL), follicular lymphoma (FL), chronic Lymphocytic leukemia (CLL)/small lymphocytic lymphoma (SLL), marginal zone lymphoma (MZL), chronic myelogenous leukemia (CML), mantle cell lymphoma (MCL), Waldenstrom's macroglobulinemia (WM), multiple myeloma (MM). More preferably, the hematological malignancy is selected from diffuse large B-cell lymphoma (DLBCL) and follicular lymphoma (FL).

Preferably, the cancer is B cell proliferative disease. More preferably, the B cell proliferative disease is selected from the group consisting of: diffuse large B cell lymphoma, follicular lymphoma, chronic lymphocytic lymphoma, chronic lymphocytic leukemia, B-cell pro-lymphocytic leukemia, lymphoplasmacytic lymphoma/Waldenstrom macroglobulinemia, splenic marginal zone lymphoma, plasma cell myeloma, plasmacytoma, extranodal marginal B-cell lymphoma, lymph node marginal B-cell lymphoma, mantle cell lymphoma, mediastinal (thymus) large B-cell lymphoma, intravascular large B-cell lymphoma, primary exudative lymphoma, Burkitt's lymphoma/leukemia and lymphomatoid granulomatosis.

In some embodiments, the disease is an autoimmune disease. In some embodiments, the autoimmune disease is refractory or is resistant to a BTK inhibitor. In certain embodiments, the autoimmune disease is refractory or is resistant to ibrutinib.

Further, the autoimmune disease described in the present invention includes, but is not limited to, an autoimmune disease selected from the group consisting of inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, SjOgren's syndrome, multiple sclerosis, Guillain-Barre syndrome, acute disseminated encephalomyelitis, Addison's disease, opsoclonus-myoclonus syndrome, ankylosing spondylitis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, familial dysautonomia, endometriosis, interstitial cystitis, neuromyotonia and vulvodynia.

In some embodiments, the disease is an inflammatory disease. In some embodiments, the inflammatory disease is refractory or is resistant to a BTK inhibitor. In certain embodiments, the inflammatory disease is refractory or is resistant to ibrutinib.

Further, the inflammatory disease described in the present invention includes, but is not limited to, an inflammatory disease selected from the group consisting of asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis, myocarditis, myositis, nephritis, oophoritis, orchitis, osteitis, otitis, pancreatitis, parotitis, pericarditis, peritonitis, pharyngitis, pleurisy, phlebitis, pneumonitis, pneumonia, proctitis, prostatitis, pyelonephritis, rhinitis, salpingitis, nasosinusitis, stomatitis, synovitis, tendonitis, tonsillitis, uveitis, vaginitis, vasculitis or vulvitis.

A third aspect of the invention relates to a combination product for preventing and/or treating a disease, in which the combination product comprises a Bcl-2 inhibitor or a Bcl-2/Bcl-xL dual inhibitor and a BTK inhibitor, and the disease is selected from the group consisting of cancer, autoimmune disease and inflammatory disease. Further, the cancer, autoimmune disease, and inflammatory disease include, but are not limited to, the cancers, autoimmune diseases and inflammatory diseases described in the second aspect of the invention as described in the above detailed description of the invention. Further, the disease is refractory or is resistant to BTK inhibitors (e.g., ibrutinib).

In some embodiments, the Bcl-2 inhibitor is a compound (e.g, Compound I-A, Compound I-b, Compound I-c, Compound I-d, Compound I-e, Compound I-f, Compound I-g, Compound I-h, Compound I-i), or a pharmaceutically acceptable salt or solvate thereof, as specifically described in the first aspect of the invention.

In some embodiments, the Bcl-2/Bcl-xL dual inhibitor is a compound (e.g., Compound I, II, III, or IV) as specifically described in the first aspect of the invention, or a pharmaceutically acceptable salt or solvate thereof. In some embodiments, the Bcl-2/Bcl-xL inhibitor is Compound 72 or Compound 88.

In some embodiments, the BTK inhibitor is selected from the group consisting of: Ibrutinib, ICP-022, Acalabrutinib (ACP-196), BGB3111, ONO/GS-4059, Spebrutinib (CC-292 or AVL-292), CNX-774, Olmutinib (HM61713, B11482694), M7583, HM71224, PCI-32765 racemate, GDC-0853, ONO-4059, Zanubrutinib, RN486, PCI-32765, CGI-1746, QL47, LFM-A13, (±)-Zanubrutinib, SNS-062, BMS-935177, Btk inhibitor 2, Evobrutinib, Ibrutinib-biotin, BMX-IN-1, GDC-0834 and CB1763. Preferably, the BTK inhibitor is selected from the group consisting of: Ibrutinib, Acalabrutinib (ACP-196) and BGB3111. More preferably, the BTK inhibitor is Ibrutinib.

In some embodiments, the combination product is in the form of a pharmaceutical composition.

In some embodiments, the Bcl-2 inhibitor and the BTK inhibitor are each in a separate preparation, or the Bcl-2/Bcl-xL dual inhibitor and the BTK inhibitor are each in a separate preparation.

In some embodiments, the Bcl-2 inhibitor and the BTK inhibitor are administered simultaneously or sequentially, or the Bcl-2/Bcl-xL dual inhibitor and the BTK inhibitor are administered simultaneously or sequentially.

In some embodiments, the Bcl-2 inhibitor or the Bcl-2/Bcl-xL dual inhibitor and the BTK inhibitor may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, About 5 weeks, about 6 weeks, about 8 weeks, or about 12 weeks.

In some embodiments, the combination product of the invention comprising the Bcl-2 inhibitor or the Bcl-2/Bcl-xL dual inhibitor and the BTK inhibitor in the form of a pharmaceutical composition (preferably, each in a separate dosage unit form), as desired, can be daily administered for, including but not limited to: 1 time, 2 times, 3 times, 4 times, 5 times or 6 times.

In some embodiments, the combination product of the invention comprising the Bcl-2 inhibitor or the Bcl-2/Bcl-xL dual inhibitor and the BTK inhibitor in the form of a pharmaceutical composition (preferably, in the form of a dosage unit), as desired, can be daily administered for, including but not limited to: 1 time, 2 times, 3 times, 4 times, 5 times or 6 times.

In some embodiments, the combination product can be administered in the following manner: oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor or the Bcl-2/Bcl-xL dual inhibitor or a pharmaceutically acceptable salt or solvate thereof, and the BTK inhibitor or a pharmaceutically acceptable salt or solvate thereof, are administered in a daily dose as described in the above first aspect of the invention in the detailed description of the invention.

A fourth aspect of the invention relates to a method of preventing and/or treating a disease, comprising administering to a subject in need thereof a prophylactically and/or therapeutically effective amount of a Bcl-2 inhibitor or a Bcl-2/Bcl-xL dual inhibitor and a BTK inhibitor, in which the disease is selected from the group consisting of cancer, autoimmune disease and inflammatory disease. Further, the cancer, autoimmune disease and inflammatory disease include, but are not limited to, the cancers, autoimmune diseases and inflammatory diseases described in the second aspect of the invention in the above detailed description of the invention. Further, the disease is refractory or is resistant to BTK inhibitors (such as ibrutinib).

In some embodiments, the Bcl-2 inhibitor is a compound (e.g., Compound I-A, Compound I-b, Compound I-c, Compound I-d, Compound I-e, Compound I-f, Compound I-g, Compound I-h, Compound I-i), or a pharmaceutically acceptable salt or solvate thereof, as specifically described in the first aspect of the invention.

In some embodiments, the Bcl-2/Bcl-xL dual inhibitor is a compound (e.g., Compound I, II, III, or IV) as specifically described in the first aspect of the invention, or a pharmaceutically acceptable salt or solvate thereof. In some embodiments, the Bcl-2/Bcl-xL inhibitor is Compound 72 or Compound 88.

In some embodiments, the BTK inhibitor is selected from the group consisting of: Ibrutinib, ICP-022, Acalabrutinib (ACP-196), BGB3111, ONO/GS-4059, Spebrutinib (CC-292 or AVL-292), CNX-774, Olmutinib (HM61713, B11482694), M7583, HM71224, PCI-32765 Racemate, GDC-0853, ONO-4059, Zanubrutinib, RN486, PCI-32765, CGI-1746, QL47, LFM-A13, (±)-Zanubrutinib, SNS-062, BMS-935177, Btk inhibitor 2, Evobrutinib, Ibrutinib-biotin, BMX-IN-1, GDC-0834 and CB1763. Preferably, the BTK inhibitor is selected from the group consisting of: Ibrutinib, Acalabrutinib (ACP-196) and BGB3111. More preferably, the BTK inhibitor is Ibrutinib.

In some embodiments, the medicament is in the form of a pharmaceutical composition, or the Bcl-2/Bcl-xL dual inhibitor and the BTK inhibitor are in the form of a pharmaceutical composition.

In some embodiments, the Bcl-2 inhibitor and the BTK inhibitor are each in a separate preparation, or the Bcl-2/Bcl-xL dual inhibitor and the BTK inhibitor are each in a separate preparation.

In some embodiments, the Bcl-2 inhibitor and the BTK inhibitor are administered simultaneously or sequentially, or the Bcl-2/Bcl-xL dual inhibitor and the BTK inhibitor are administered simultaneously or sequentially.

In some embodiments, the Bcl-2 inhibitor or the Bcl-2/Bcl-xL dual inhibitor and the BTK inhibitor may be administered sequentially at a time interval of about 1 minute, about 5 minutes, about 10 minutes, about 15 minutes, about 30 minutes, about 45 minutes, about 1 hour, about 2 hours, about 4 hours, about 6 hours, about 12 hours, about 24 hours, about 48 hours, about 72 hours, about 96 hours, about 1 week, about 2 weeks, about 3 weeks, about 4 weeks, About 5 weeks, about 6 weeks, about 8 weeks, or about 12 weeks.

In some embodiments, the Bcl-2 inhibitor or the Bcl-2/Bcl-xL dual inhibitor and the BTK inhibitor in the form of a pharmaceutical composition (preferably, each in a separate dosage unit form), as desired, can be daily administered for, including but not limited to: 1 time, 2 times, 3 times, 4 times, 5 times or 6 times.

In some embodiments, the Bcl-2 inhibitor or the Bcl-2/Bcl-xL dual inhibitor and the BTK inhibitor in the form of a pharmaceutical composition (preferably, in the form of a dosage unit), as desired, can be daily administered for, including but not limited to: 1 time, 2 times, 3 times, 4 times, 5 times or 6 times.

In some embodiments, the Bcl-2 inhibitor or the Bcl-2/Bcl-xL dual inhibitor and the BTK inhibitor can be administered in the following manner: oral, buccal, inhalation spray, sublingual, rectal, transdermal, vaginal mucosa, transmucosal, local, nasal or enteral administration; parenteral administration, such as intramuscular injection, subcutaneous injection, intramedullary injection, as well as intrathecal or brain direct administration, in situ administration, subcutaneous, intraperitoneal, intravenous injection, intra-articular synovium, intrasternal, intrahepatic, intralesional, intracranial, intra-abdominal, nasal, or intraocular injection or other drug delivery manners.

In some embodiments, the Bcl-2 inhibitor is administered daily at a dose of 0.017 mg/kg, 0.083 mg/kg, 0.17 mg/kg, 0.33 mg/kg, 0.5 mg/kg, 0.67 mg/kg, 0.83 mg/kg, 1 mg/kg, 1.16 mg/kg, 1.33 mg/kg, 1.5 mg/kg, 1.67 mg/kg, 2.5 mg/kg, 3.33 mg/kg, 4.17 mg/kg, 5 mg/kg, 5.83 mg/kg, 6.67 mg/kg, 7.5 mg/kg, 7.67 mg/kg, 7.83 mg/kg, 8 mg/kg, 8.12 mg/kg, 8.16 mg/kg, 8.33 mg/kg, 9.17 mg/kg, 10 mg/kg, 10.83 mg/kg, 11.66 mg/kg, 12.5 mg/kg, 13.33 mg/kg, 14.17 mg/kg, 15 mg/kg, 15.83 mg/kg, 16.67 mg, and a range between the respective application doses, for example, 0.017 mg to 16.67 mg/kg, 0.083 mg to 16.67 mg/kg, 0.17 mg to 16.67 mg/kg, 0.33 mg to 16.67 mg/kg, 0.5 mg to 15 mg/kg, 0.5 mg to 13.33 mg/kg, 0.5 mg to 11.67 mg/kg, 0.5 mg to 10 mg/kg, 0.5 mg to 8.33 mg/kg, 0.5 mg to 8.16 mg/kg, 0.5 mg to 8.12 mg/kg, etc., and the BTK inhibitor administered daily at a dose of 0.17 mg/kg, 0.33 mg/kg, 0.5 mg/kg, 0.67 mg/kg, 0.83 mg/kg, 1 mg/kg, 1.17 mg/kg, 1.22 mg/kg, 1.33 mg/kg, 1.5 mg/kg, 1.62 mg/kg, 1.67 mg/kg, 2.03 mg/kg, 2.5 mg/kg, 3.33 mg/kg, 4.17 mg/kg, 5 mg/kg, 5.83 mg/kg, 6.67 mg/kg, 7.5 mg/kg, 7.67 mg/kg, 7.83 mg/kg, 8 mg/kg, 8.17 mg/kg, 8.33 mg/kg, and a range between the respective doses, for example, 0.17 mg to 8.33 mg/kg, 0.33 mg to 7.5 mg/kg, 0.5 mg to 6.67 mg/kg, 0.83 mg to 5.83 mg/kg, 1 mg to 5 mg/kg, 1.16 mg to 4.17 mg/kg, 1.22 mg to 3.33 mg/kg, 1.22 mg to 2.5 mg/kg, 1.22 mg to 2.03 mg/kg, 1.62 mg to 8.33 mg/kg, 1.62 mg to 8 mg/kg, 1.62 mg to 7.5 mg/kg, 1.62 mg to 5 mg/kg, 1.62 mg to 2.5 mg/kg, 1.22 mg to 1.62 mg/kg, etc. In certain embodiments, the Bcl-2/Bcl-xL dual inhibitor is administered daily at a dose of from about 10 mg/week to about 1000 mg/week, from about 10 mg/week to about 900 mg/week, from about 10 mg/week to about 800 mg/week, about 10 mg/week to about 700 mg/week, about 10 mg/week to about 640 mg/week, about 10 mg/week to about 600 mg/week, about 10 mg/week to about 500 mg/week, about 10 mg/week to about 400 mg/week, about 10 mg/week to about 300 mg/week, about 10 mg/week to about 200 mg/week, or about 20 mg/week to about 100 mg/week, for example about 10, 15, 20, 25, 30, 35, 40, 50, 55, 60, 65, 70, 75, 80, 85, 90, 95, 100, 150, 200, 250, 300, 350, 400, 450, 500, 550, 600, 650, 700, 750, 800, 850, 900, 950, 1000 mg/week.

Lastly, WO 2018/027097 is incorporated by reference herein, in its entirety and for all purposes.

SPECIFIC MODELS FOR CARRYING OUT THE INVENTION

The present invention will be further illustrated by the following examples and control examples. However, it should be understood that these examples and control examples are merely used to explain the invention in more details, but not intend to limit the present invention.

Example 1. General Experimental Methods Used in the Invention (1) WST Experiment The anti-proliferative effect was tested by CCK-8 (Cell Counting Kit-8) (purchased from Shanghai Liji Medical Technology Co., Ltd.) based on water-soluble tetrazolium salt (WST) (please refer to: Ishiyama M, Tominaga H, Shiga M et al., A combined assay of cell viability and in vitro cytotoxicity with a highly water-soluble tetrazolium salt, neutral red and crystal violet. Biol. Pharm. Bull 19 (11) 1518-1520 (1996), Vol. 19, No. 11; and Tominaga H, Ishiyama M, Ohseto F et al., A water-soluble tetrazolium salt useful for colorimetric cell viability assay. Anal. Commun., 1999, 36, 47-50). Cells were inoculated to 96-well plates, treated with different concentrations of the test substance for 72 hours. By acting 9 different concentrations of BTK inhibitor (for example, Ibrutinib, wherein 9 concentrations were selected in a 3× gradient between 10-2 and 102) with 3 different concentrations of Compound 6 (see FIG. 1 for details) for 72 hours, the combination effect of Compound 6 and the drug were tested. Each test dose was tested with 3 replicate wells.

Usually, 9 series of doses of the test substance were selected, and added to 96-well plates, 100 μl/well. For the combination experiment, the final volume of the two test substances is 100 μl/well. Each test dose was tested with 3 replicate wells. On the same plate, 3-6 wells were selected and added with 100 μl of dilution solution as a control group, and another 3-6 wells were used as a blank control. In addition to the blank control wells, 100 μl of the cell suspension was added to each well (containing an appropriate number of cells to ensure that at the time of detection, the cells of the cell control group just covered the bottom of the well) of the same 96-well plate. The culture plate was cultured at 37° C. for 72 hours in a CO2 incubator. At the end of the culture, for the adherent cells, the old solution in the well to be tested was removed, and 100 μl/well of CCK-8 test solution (corresponding medium containing 10% CCK-8, 5% FBS) was added. For the suspension cells, 20 μl/well of CCK-8 stock solution was added directly. The plate was continuously incubated at 37° C. for 2-4 h in CO2 incubator.

The OD values were measured at A450 nm by a microplate reader (SpectraMax Plus 384, Molecular Devices, LLC., US). Using the average OD value of 3 replicate wells, the percentage of cell viability was calculated by the following formula:

(*O.D.* of test well–*O.D.* of blank control well)/(*O.D.* of cell control well–*O.D.* of blank control well)×100.

The IC50 was calculated using the nonlinear regression data analysis method of Graphpad Prism 6.0 software.

For the combination test, the cell survival rate was calculated by normalizing the average OD value of 3 duplicate wells of the single drug control. By comparing the IC50 of the combination curve with the single drug curve, the synergistic effect of two compounds was determined by combining the observation of whether the curve of the combination group was shifted left.

(2) Evaluation Method of In Vivo Pharmacodynamics Experimental

A subcutaneous xenograft tumor model of human tumor immunodeficient mice was established by cell inoculation: tumor cells in logarithmic growth phase were collected, counted and resuspended in 1×PBS, and the cell suspension concentration was adjusted to 2.5-5×10$^7$/mL. Using a 1 mL syringe (4th needle), the tumor cells were inoculated subcutaneously in the right side of immunodeficient mice, 5-10×10$^6$/0.2 mL/mouse. All animal experiments were strictly in accordance with the laboratory animal use and management practices of GenePharma Co., Ltd. and Ascentage Pharma Group Co., Ltd. The calculation of relevant parameters referred to the Chinese CFDA "Guidelines for Non-Clinical Research Techniques of Cytotoxic Antitumor Drugs". The sources of experimental animals are shown in the following table:

TABLE 2

Experimental animal sources

| Tumor model | Experiment number | Number of inoculated animals | Breed | Animal source (license number) |
|---|---|---|---|---|
| OCI-LY1 | APS-EF-82-2017-OCI-LY1 | 30 | NOD SCID | Beijing Vital River Laboratory Animal Technology Co., Ltd. SCXK (Beijing) 2016-0006 |
| DOHH2 | SZ-EF-11-2017-DOHH2 | 100 | CB17/ SCID | Beijing Vital River Laboratory Animal Technology Co., Ltd. SCXK (Beijing) 2016-0006 |
| DOHH2 | SZ-EF-01-2018-DOHH2 | 95 | CB17/ SCID | Beijing Vital River Laboratory Animal Technology Co., Ltd. SCXK (Beijing) 2016-0006 |
| OCI-LY1 | APS-EF-82-2017-OCI-LY1 | 80 | NOD SCID | Beijing Vital River Laboratory Animal Technology Co., Ltd. SCXK (Beijing) 2016-0006 |

Animal body weight and tumor size were measured twice a week during the experiment. Tumor growth was observed periodically, and the animals were randomly divided into groups according to tumor size and mouse body weight when the tumors grew to an average volume of 100-200 mm$^3$. The conditions and death of the animals were observed every day. Routine monitoring included the effects of tumor growth and treatment on normal animal behaviors, including activity, feeding and drinking situations, weight gain or loss, eyes, coat and other abnormalities in the experimental animals. The deaths and clinical symptoms observed during the experiment were recorded in the raw data. The entire operations of administration, measurement of mouse body weight and tumor volume were performed in a clean bench. Plasma and tumor tissues were collected, weighed and photographed after the end of the last administration according to the experimental protocol. Plasma and tumor samples were frozen and stored at −80° C.

Tumor volume (TV) was calculated as: $TV = a \times b^2/2$, in which a and b represented the length and width of the tumor as measured, respectively. The relative tumor volume (RTV) was calculated as: $RTV = V_t/V_1$, in which $V_1$ was the tumor volume at the time of grouping and administration, and $V_t$ was the tumor volume measured on a day after administration. The evaluation index of anti-tumor activity was the relative tumor proliferation rate T/C (%), which was calculated as: relative tumor proliferation rate T/C (%)=($T_{RTV}$/$C_{RTV}$)×100%, in which $T_{RTV}$ was the RTV of the treatment group, $C_{RTV}$ was the RTV of the vehicle control group; tumor remission rate (%) was calculated as: (the number of SD (stable disease), PR (tumor partial regression) and CR (tumor complete regression) in the tumor-bearing mice after treatment)/the total number of mice in the group×100%.

Change of body weight %=(measured body weight−body weight at the time of grouping)/body weight at the time of grouping×100%.

Evaluation criteria of therapeutic efficiency: according to the Chinese CFDA "Technical guidelines for non-clinical research on cytotoxic antitumor drugs" (November 2006), it was determined as effective when the T/C (%) value was ≤40% and statistic analysis showed p<0.05; and a dose of the drug was considered to be severely toxic when the body weight of the mice dropped by more than 20% or the rate of drug-related deaths exceeded 20%.

The synergistic analysis was performed by the following formula: synergy factor=((A/C)×(B/C))/(AB/C); A=RTV value of the group administered with A only; B=RTV value of the group administered with B only; C=RTV value of the vehicle control group; AB=RTV value of the group administered with A and B in combination (Clarke R. Issues in experimental design and endpoint analysis in the study of experimental cytotoxic agents in vivo in breast cancer and other models [J]. Breast Cancer Research & Treatment, 1997, 46(2-3): 255-278). If the synergy factor was >1, there was a synergistic effect; if the synergistic factor=1, there was an additive effect; if the synergistic factor <1, there was an antagonistic effect.

Example 2. Preparation of Exemplary Compounds as Bcl-2 Inhibitors (Compounds 3, 6 and 13)

(1) Synthesis of 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide

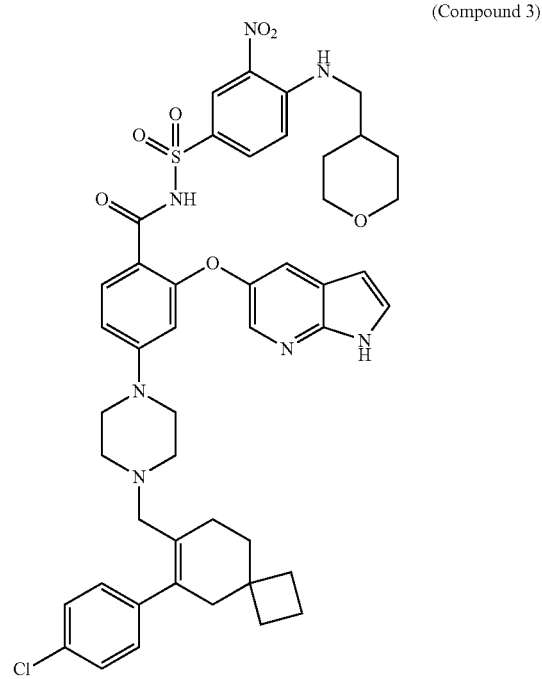 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1]

(Compound 3)

A mixture of 2-((1H-pyrrolo[2,3-b]pyridin-5-yl)oxy)-4-(4-((6-(4-chlorophenyl) spiro[3.5]non-6-en-7-yl)methyl) piperazin-1-yl)benzoic acid (1.75 g, 3 mmol), 3-nitro-4-(((tetrahydro-2H-pyran-4-yl)methyl)amino) benzenesulfonamide (1.43 g, 4.5) reacted in EDCl (1.15 g, 6 mmol) and 4-(N,N-dimethylamino)pyridine (550 mg, 4.5 mmol) and dichloromethane (40 ml) at room temperature overnight, and then water was added. The aqueous layer was extracted with dichloromethane. The combined organic layers were washed with brine, concentrated and purified with silica column to obtain 2-((1H-pyrrolo[2,3-b]pyridin-5-yl)oxo)-4-(4-((6-(4-chlorophenyl)spiro[3.5]non-6-en-7-yl)methyl)piperazin-1-yl)-N-((3-nitro-4-((tetrahydro-2H-pyran-4-yl)methyl)amino)phenyl)sulfonyl)benzamide (1.7 g, 64.4%) was obtained as a yellow solid.

$^1$H NMR (400 MHz, methanol-d4) δ 8.70 (d, J=2.3 Hz, 1H), 8.01 (d, J=2.7 Hz, 1H), 7.87 (d, J=9.2, 2.3 Hz, 1H), 7.66 (d, J=8.9 Hz, 1H), 7.55 (d, J=2.7 Hz, 1H), 7.47 (d, J=3.4 Hz, 1H), 7.38 (d, J=8.4 Hz, 2H), 7.10 (d, J=8.4 Hz, 2H), 6.97 (d, J=9.2 Hz, 1H), 6.77 (dd, J=8.9, 2.4 Hz, 1H), 6.44 (d, J=3.4 Hz, 1H), 6.34 (d, J=2.4 Hz, 1H), 4.02-3.94 (m, 3H), 3.66 (s, 3H), 3.49-3.38 (m, 2H), 3.41-3.25 (m, 7H), 2.42 (s, 3H), 2.26 (s, 3H), 2.00-1.67 (m, 4H), 1.45-1.38 (m, 2H).

(2) Synthesis of (R)—N-((4-(((1,4-dioxan-2-yl)methyl)amino)-3-nitrophenyl) sulfonyl)-2-((1H-pyrrolo[2,3-b]pyridin-5-yl)oxy)-4-(4-((6-(4-chlorophenyl)spiro[3.5] non-6-en-7-yl)) methyl)piperazin-1-yl)benzamide

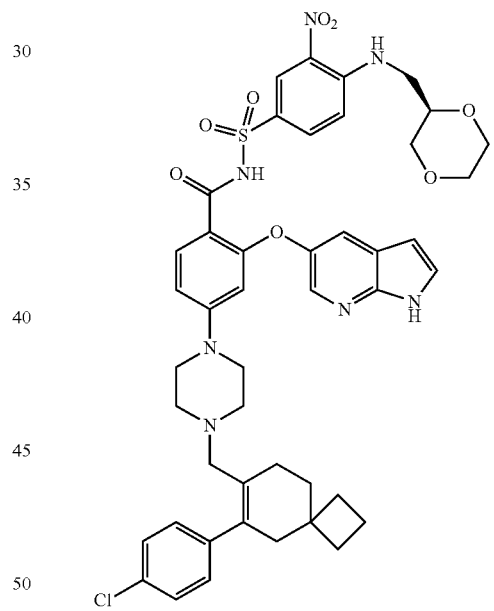

(Compound 13)

The title compound was prepared in a similar manner to that described for the synthesis of Compound 3.

1H NMR (400 MHz, methanol-d4) δ 8.66 (d, J=2.4 Hz, 1H), 7.99 (d, J=2.4 Hz, 1H), 7.84 (dd, J=9.2, 2.4 Hz, 1H), 7.64 (d, J=8.9 Hz, 1H), 7.51 (d, J=2.4 Hz, 2H), 7.45 (d, J=3.3 Hz, 1H), 7.37 (d, J=8.4 Hz, 2H), 7.10 (d, J=8.4 Hz, 2H), 6.94 (d, J=9.2 Hz, 1H), 6.76 (dd, J=8.9, 2.3 Hz, 1H), 6.40 (d, J=3.3 Hz, 1H), 6.36 (d, J=2.3 Hz, 1H), 3.87 (dd, J=11.8, 4.2 Hz, 3H), 3.83-3.70 (m, 3H), 3.67 (s, 2H), 3.62 (dd, J=11.7, 2.9 Hz, 1H), 3.51-3.41 (m, 2H), 3.40-3.35 (m, 1H), 3.29 (dq, J=3.2, 1.6 Hz, 1H), 2.41 (s, 2H), 2.26 (s, 2H), 2.00-1.77 (m, 6H).

Similarly, Compound 6 was prepared similarly according to the method described for the synthesis of Compound 13, with specific reference to WO 2018/027097.

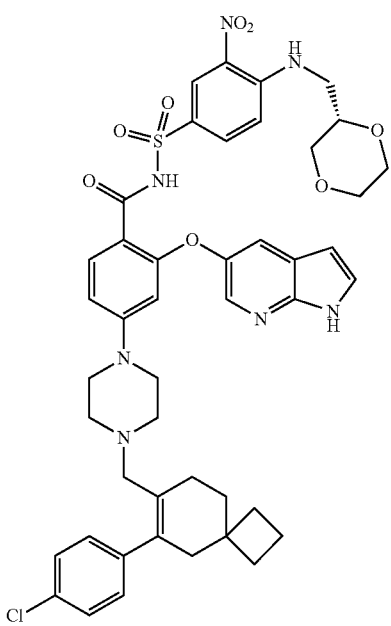

Compound 6

Example 3. Effects of Ibrutinib Alone and Combination of Ibrutinib and Compound 6 on Different Malignant Tumor Cells (1) The experimental method was as described in Example 1 (1). The cell viability (%) of Ibrutinib alone and the combination of Ibrutinib and Compound 6 in the following malignant tumor cells were determined in WST experiments: OCI-LY8 (diffuse large B-cell lymphoma (DLBCL)), SU-DHL-4 (diffuse large B-cell lymphoma (DLBCL)), OCI-LY1 (diffuse large B-cell lymphoma (DLBCL)), DOHH2 (follicular lymphoma (FL)), RPMI-8226 (multiple myeloma (MM)), KMS-11 (multiple myeloma (MM)), Z-138 (mantle cell lymphoma (MCL)).

(2) Experimental Results

Figure 1:
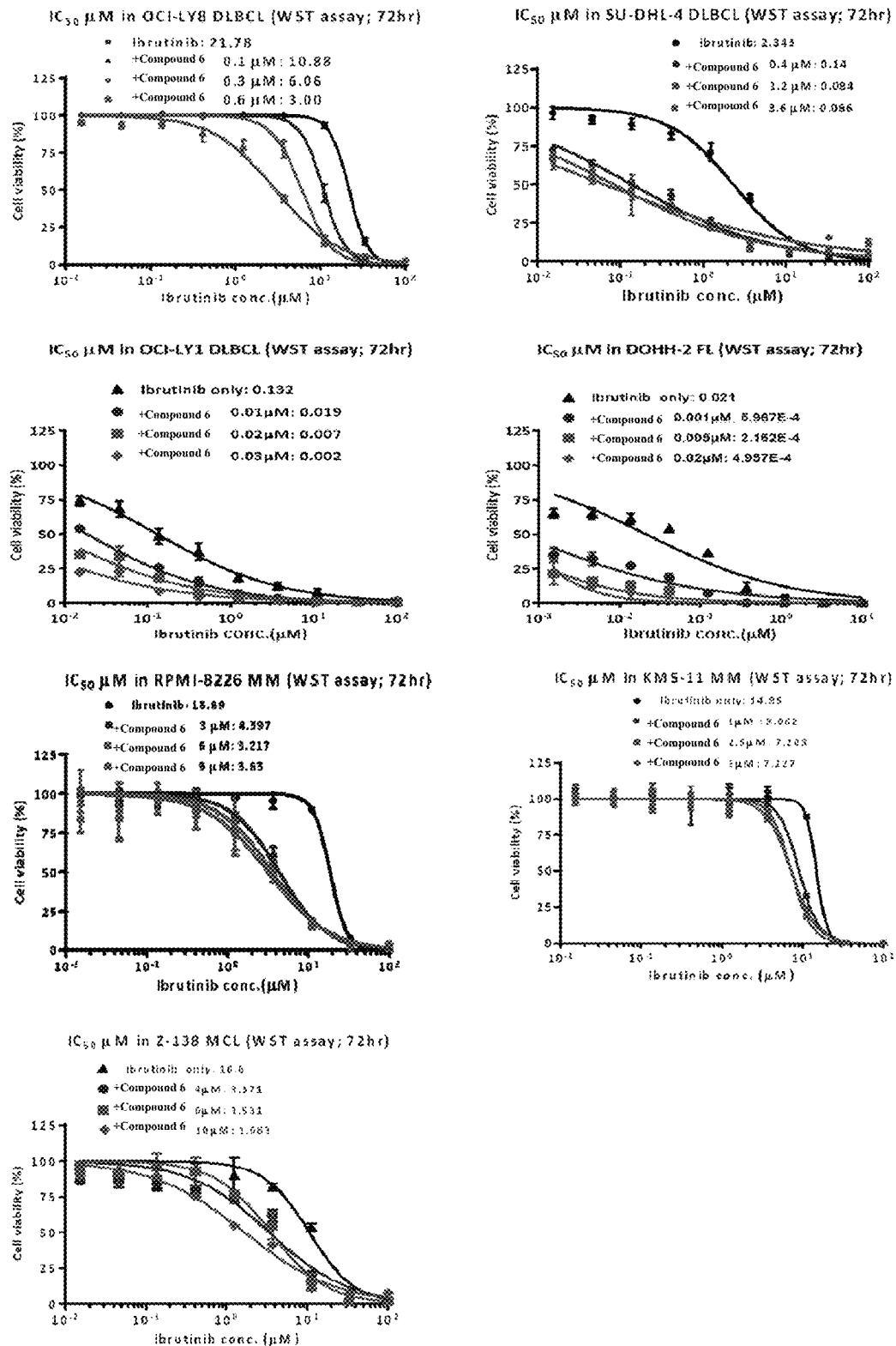

As shown in FIG. 1, in a variety of hematological malignant cells, the combination of Compound 6 and BTK inhibitor Ibrutinib showed increased inhibition effects on the proliferation of the tumor cells.

Specifically, in OCI-LY8 (DLBCL), the $IC_{50}$ of Ibrutinib alone for inhibition of proliferation was 21.78, while the $IC_{50}$ values of Ibrutinib and Compound 6 (0.1 μM, 0.3 μM, 0.6 μM) for inhibition of proliferation were 10.88, 6.06, and 3.00, respectively; in SU-DHL-4 (DLBCL), the $IC_{50}$ of Ibrutinib alone for inhibition of proliferation was 2.343, while the $IC_{50}$ values of Ibrutinib and Compound 6 (0.4 μM, 1.2 μM, 3.6 μM) for inhibition of proliferation were 0.14, 0.084, and 0.066, respectively; in OCI-LY1 (DLBCL), the $IC_{50}$ of Ibrutinib alone for inhibition of proliferation was 0.132, while the $IC_{50}$ values of Ibrutinib and Compound 6 (0.01 μM, 0.02 μM, 0.03 μM) for inhibition of proliferation were 0.019, 0.007, and 0.002, respectively; in DOHH2 (FL), the $IC_{50}$ of Ibrutinib alone for inhibition of proliferation was 0.021, while the $IC_{50}$ values of Ibrutinib and Compound 6 (0.001 μM, 0.005 μM, 0.02 μM) for inhibition of proliferation were $5.967 \times 10^{-4}$, $2.162 \times 10^{-4}$, and $4.957 \times 10^{-4}$, respectively; in RPMI-8226 (MM), the $IC_{50}$ of the proliferation of Ibrutinib alone for inhibition of proliferation was 18.69, while the $IC_{50}$ values of Ibrutinib and Compound 6 (3 μM, 6 μM, 9 μM) for inhibition of proliferation were 4.397, 3.217 and 3.63, respectively; in KMS-11 (MM), the $IC_{50}$ of Ibrutinib alone for inhibition of proliferation was 14.85, while the $IC_{50}$ values of Ibrutinib and Compound 6 (1 μM, 2.5 μM, 5 μM) for inhibition of proliferation were 9.062, 7.203 and 7.227, respectively; in Z-138 (MCL), the $IC_{50}$ of Ibrutinib for inhibition of proliferation was 10.6, while the $IC_{50}$ values of Ibrutinib and Compound 6 (4 μM, 6 μM, 10 μM) for inhibition of proliferation were 3.371, 3.531 and 1.663, respectively.

(3) Summary

Thus, in vitro experiments, when Compound 6 was used in combination with a targeting therapeutic drug (i.e, a BTK inhibitor), the in vitro anti-proliferative activity of Compound 6 in hematological malignancies was further enhanced. The comparison of $IC_{50}$ was performed with the curves of combination administration and the curves of single administration, and it was observed that the curves of combination administration showed left shift, and the $IC_{50}$ values of the combination administration groups were smaller than the $IC_{50}$ values of respective single administration. Therefore, the combination of Ibrutinib and Compound 6 had a synergistic effect.

Example 4. Effects of Ibrutinib Alone and Combination of Ibrutinib and Compound 6 in Human OCI-LY1 Cell Line DLBCL Mouse Xenograft Tumor Model (1) The experimental method was as described in the section (2) of Example 1. In the experiment, the therapeutic effects of the combination of Ibrutinib and Compound 6 were evaluated with a DLBCL xenograft tumor model derived from a human OCI-LY1 cell line (see: Donnou S, Galand C, Touitou V et al., Murine Models of B-Cell Lymphomas: Promising Tools for Designing Cancer Therapies. Advances in Hematology, Volume 2012, Article ID 701704, 13 pages; and, Benet Pera, Tiffany Tang, Rossella Marullo et al., Combinatorial epigenetic therapy in diffuse large B cell lymphoma pre-clinical models and patients. Clin Epigenetics 2016; 8: 79). In short, when the average tumor volume reached approximately 90 mm³, grouping and administration started. Ibrutinib was administered at a dose of 15 mg/kg, i.v., qd, from the day of grouping, for 3 weeks. Compound 6 was administered at a dose of 100 mg/kg, p.o., qd, from the $8^{th}$ day after grouping, for 3 weeks. In addition, the group of combination of Ibrutinib and Compound 6 (Ibrutinib 15 mg/kg, i.v., qd+Compound 6 100 mg/kg, p.o., qd) was also provided.

(2) Experimental Results

Due to the slow growth of tumor in this model, the initial effect was not obvious. On the $13^{th}$ day after grouping, the administration was stopped and the observation period started.

Figure 2:
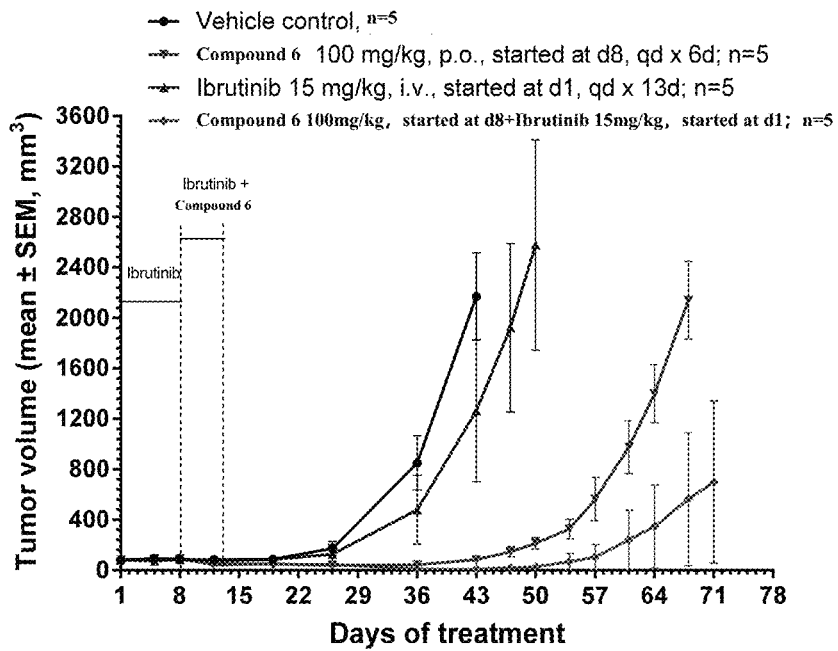
FIG. 2 shows the anti-tumor effect (A) and body weight change (B) of Compound 6 alone or in combination with Ibrutinib in a human OCI-LY1 (diffuse large B-cell lymphoma (DLBCL)) mouse xenograft tumor model.
Figure 2:
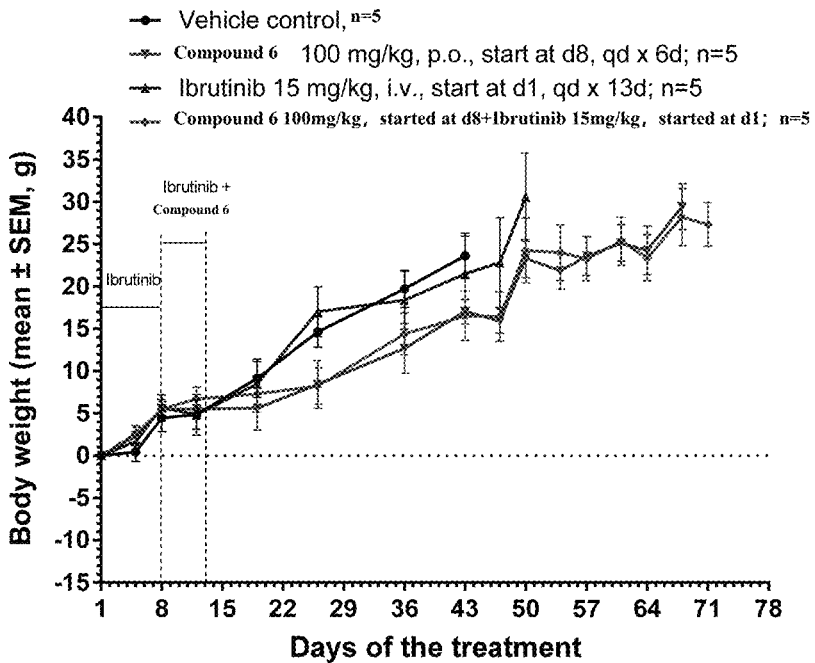

On day 43 after grouping, the Compound 6 group showed good tumor growth inhibition with a T/C % value of 4% (P<0.001; including 1/5 CR and 1/5 PR, and remission rate was 20%) (FIG. 2A and Table 3). Ibrutinib showed limited effect in this model, with a T/C % value of 58% (P>0.05). The combination of drugs significantly enhanced the efficacy, showing a T/C % value of 0% (P<0.001, compared with the vehicle control; including 4/5 CR and 1/5 PR, and the remission rate was 100%); although the RTV value was not statistically different from that of the Compound 6 alone group (P>0.05), it showed statistically difference compared with the Ibrutinib alone group (P<0.05). At the same time, 4/5 CR appeared in the combination group, suggesting that the combination was superior to the drug alone. With the prolongation of time, the difference between the combination group and the Compound 6 alone group became more and more obvious. On the $50^{th}$ day, the effect of the combination group was better than that of the two drug alone groups (P<0.05, compared with the Compound 6 alone group; P<0.01, compared with the Ibrutinib alone group). On the 68$^{th}$ day, the RTV value of the combination group was still smaller than that of the Compound 6 alone group (P<0.05), and there were still 2/5 CR and 2/5 PR. No significant weight loss was observed in each of the drug-administered groups (FIG. 2B).

of treatment. The T/C values of the Compound 6 (100 mg/kg) alone group and the combination group with Ibrutinib were 19% (P<0.01, compared with the vehicle control group) and 8% (P<0.001, compared with the vehicle control group; P<0.001, compared with the Compound 6 alone

TABLE 3

Anti-tumor effects of Compound 6 alone or in combination with Ibrutinib in human OCI-LY1 (DLBCL) mouse xenograft tumor model

| Treatment | RTV on the 43rd day after administration (mean ± standard error) | T/C (%) on day 43 after administration | TGI (%) on day 43 after administration | Synergistic factor on day 43 after administration | RTV on day 50 after administration (mean ± standard error) | Tumor status (remission rate %$^a$) on day 43 after administration | Tumor status (remission rate %$^a$) on day 50 after administration | Tumor status (remission rate %$^a$) on day 68 after administration |
|---|---|---|---|---|---|---|---|---|
| Vehicle control | 27.25 ± 3.88 | | | | | 0/5 CR, 0/5 PR (0%) | | |
| Cpd. 6, 100 mg/kg | 1.03 ± 0.33*** | 4 | 96 | | 2.64 ± 0.55 | 1/5 CR, 1/5 PR (100%) | 0/5 CR, 1/5 PR (10%) | 0/5 CR, 0/5 PR (0%) |
| Ibrutinib 15 mg/kg | 15.9 ± 7.63 | 58 | 42 | | 32.1 ± 1137 | 0/5 CR, 0/5 PR (0%) | 0/5 CR, 0/5 PR (0%) | |
| Cpd. 6 100 mg/kg + Ibrutinib 15 mg/kg | 0.07 ± 0.07***# | 0 | 100 | 8.59 | 0.28 ± 0.28###+ | 4/5 CR, 1/5 PR (100%) | 4/5 CR, 0/5 PR (80%) | 2/5 CR, 2/5 PR (80%) |

*P < 0.05,
**P < 0.01,
***P < 0.001, compared with vehicle control;
P < 0.05,
P < 0.01, compared with Ibrutinib alone group;
+P < 0.05, compared with Compound 6 along group;
$^a$remission rate, including CR, PR and SD; synergistic factor >1, synergistic effect; synergistic factor = 1, additive effect; synergistic factor <1, antagonistic effect. tumor growth inhibition (TGI) = 100 − T/C%.

(3) Summary

The combination of Compound 6 and Ibrutinib had no significant side effects, significantly increased the anti-tumor effect of single drug in the DLBCL model of OCI-LY1 cells, and showed a significant synergistic effect (synergistic factor was 8.59, much larger than 1). Therefore, the combination of Compound 6 and Ibrutinib may clinically benefit patients with diffuse large B-cell lymphoma (DLBCL).

Example 5: Effects of Ibrutinib Alone and Combination of Ibrutinib and Compound 6 in Human DOHH2 Cell Line FL Mouse Xenograft Tumor Model (1) The experimental method was as described in the section (2) of Example 1. In the in vitro cell assay, DOHH2 was a human follicular lymphoma (FL, belonging to NHL) cell line that was relatively sensitive to Compound 6 treatment. Therefore, in the experiment, a FL mouse xenograft tumor model derived from DOHH2 cells was established (see: Donnou S, Galand C, Touitou V et al., Murine Models of B-Cell Lymphomas: Promising Tools for Designing Cancer Therapies. Advances in Hematology, Volume 2012, Article ID 701704, 13 pages; and, Ackler S, Mitten M J, Chen J et al., Navitoclax (ABT-263) and bendamustine ±rituximab induce enhanced killing of non-Hodgkin's lymphoma tumours in vivo. British Journal of Pharmacology (2012) 167 881-891), which was used to evaluate the anti-tumor effect of Compound 6 in combination with BTK inhibitor Ibrutinib.

(2) Experimental Results

Figure 3:
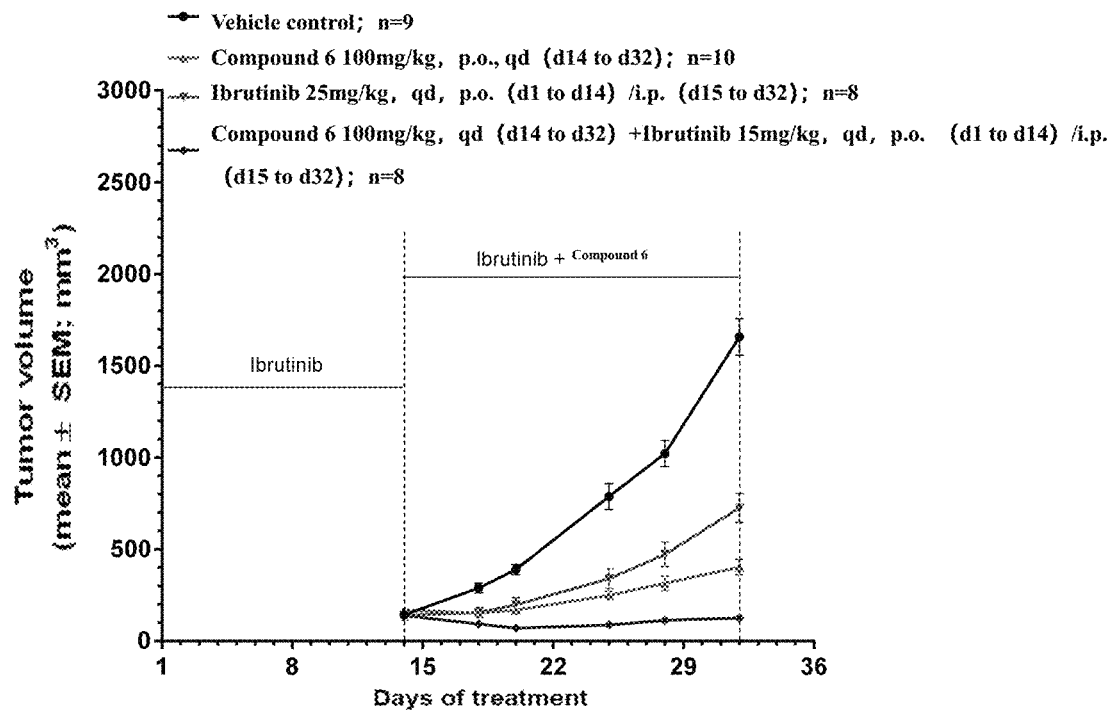
FIG. 3 shows the anti-tumor effect (A) and body weight change (B) of Compound 6 alone or in combination with Ibrutinib in a human DOHH2 (follicular lymphoma, FL) mouse xenograft tumor model.
Figure 3:
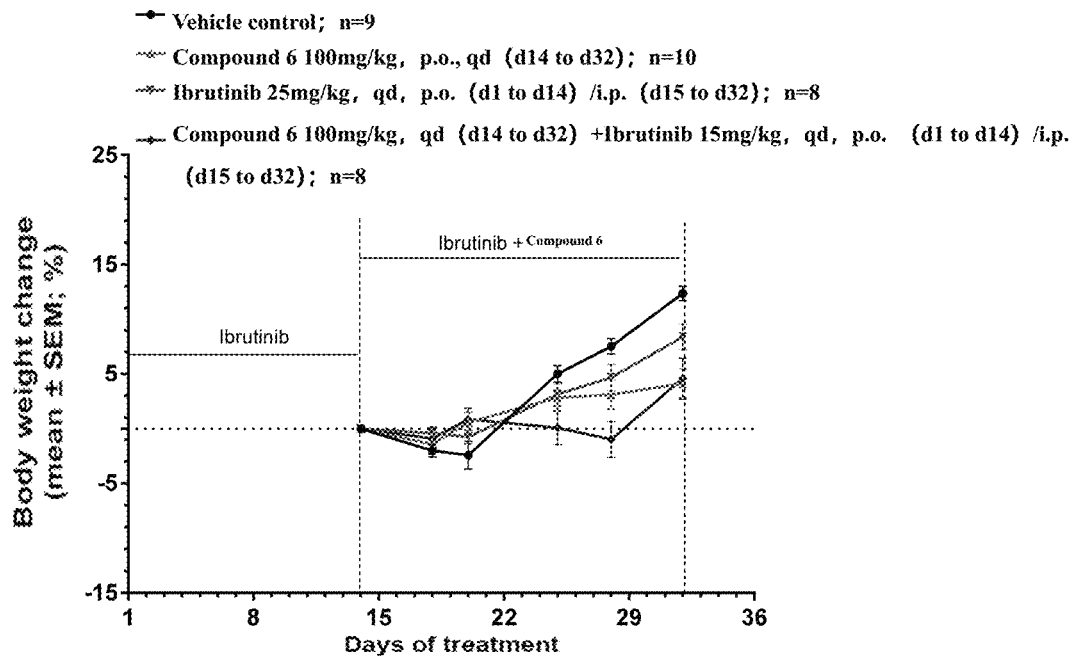

As shown in FIG. 3A and Table 4, the T/C value of the Ibrutinib (25 mg/kg) treatment group was 48% after 32 days group; P<0.01, compared with the Ibrutinib alone group), respectively.

TABLE 4

Anti-tumor effects of Compound 6 alone or in combination with Ibrutinib in human DOHH2 (FL) mouse xenograft tumor model

| Treatment | RTV on day 32 after administration (mean ± standard error) | T/C (%) on day 32 after administration | TGI (%) on day 32 after administration | Synergistic factor on day 32 after administration |
|---|---|---|---|---|
| Vehicle control | 12.7 ± 1.5 | — | | |
| Cpd. 6, 100 mg/kg | 2.4 ± 0.2** | 19 | 81 | |
| Ibrutinib 25 mg/kg | 6.1 ± 0.8* | 48 | 52 | |
| Cpd. 6, 100 mg/kg + Ibrutinib 25 mg/kg | 1.0 ± 0.2***+++## | 8 | 92 | 1.21 |

*P < 0.05,
**P < 0.01,
***P < 0.001, compared with vehicle control group;
+++P < 0.001, compared with Compound 6 alone group;
P < 0.01, compared with Ibrutinib alone group;
$$$P < 0.001, compared with ABT-199 alone group.
Synergistic factor >1, synergistic effect; synergistic factor synergistic factor <1, antagonistic effect. Tumor inhibition rate (TGI) = 100 − T/C%.

(3) Summary

The combination of Compound 6 and Ibrutinib had no significant side effects (FIG. 3B), significantly increased the anti-tumor effect of single drug in human DOHH2 (FL) mouse xenograft tumor model, and had significant synergistic effect (synergistic factor was 1.21, greater than 1). Therefore, the combination of Compound 6 and Ibrutinib may clinically benefit patients with follicular lymphoma (FL).

Example 6: Effects of Ibrutinib Alone and Combination of Ibrutinib and Compound 6 in Human DOHH2 Cell Line FL Mouse Xenograft Tumor Model (1) The experimental method was as described in the section (2) of Example 1. In the experiment, a FL mouse xenograft tumor model derived from DOHH2 cells (same as in Example 5) was established, and the anti-tumor effect of the combination of Compound 6 and BTK inhibitor Ibrutinib was evaluated.

(2) Experimental Results

Figure 4:
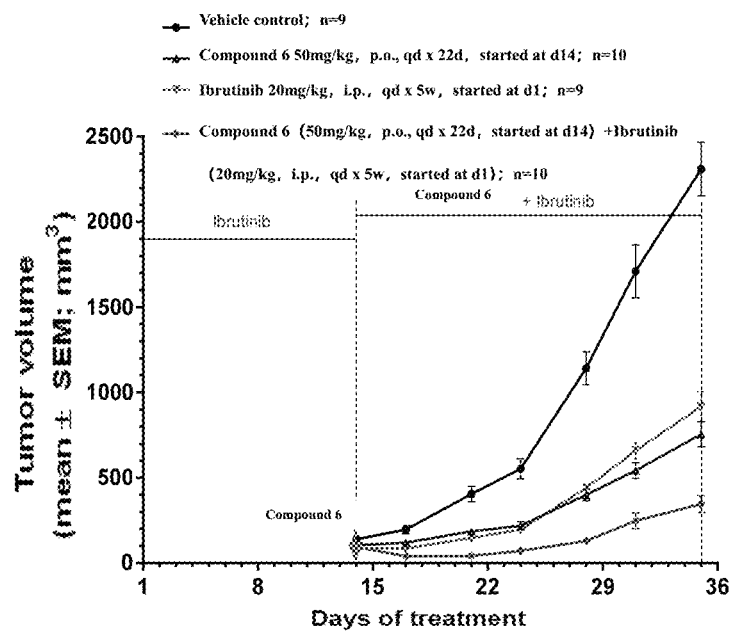
FIG. 4 shows the anti-tumor effect (A) and body weight change (B) of Compound 6 alone or in combination with Ibrutinib in a human DOHH2 (follicular lymphoma, FL) mouse xenograft tumor model.
Figure 4:
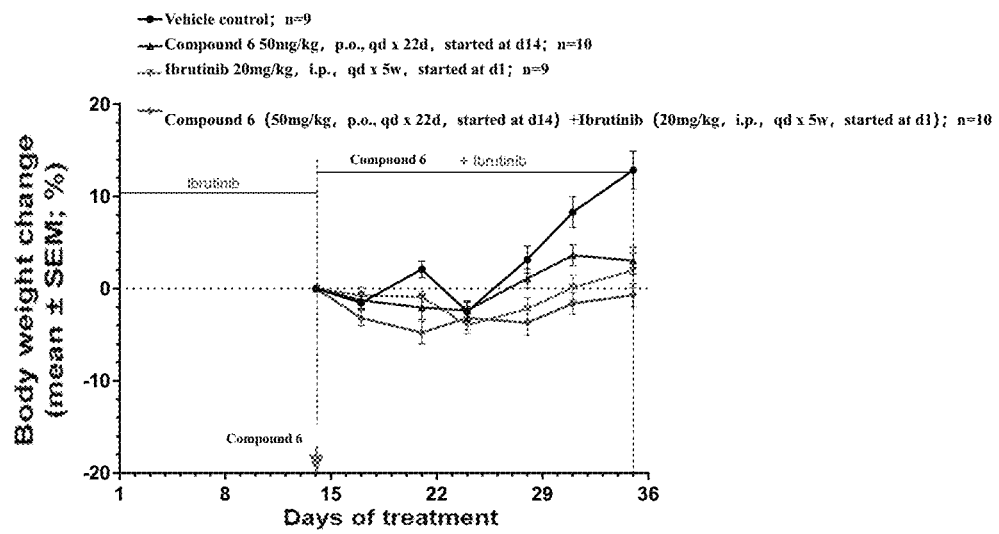

As shown in FIG. 4A and Table 5, after 35 days of treatment, the T/C value of the Ibrutinib (20 mg/kg) treatment group was 67.7% (no significant difference compared with the vehicle control group). The T/C values the Compound 6 (50 mg/kg) alone and the combination with Ibrutinib were 44.40% (P<0.001, compared with the vehicle control group) and 21.8% (P<0.001, compared with the vehicle control group; P<0.01, compared with the Compound 6 alone group; P<0.05, compared with the Ibrutinib alone group).

TABLE 5

Anti-tumor effects of Compound 6 alone
or in combination with Ibrutinib in
human DOHH2 (FL) mouse xenograft tumor model

| Treatment | RTV on day 35 after administration (mean ± standard error) | T/C (%) on day 35 after administration | Synergistic factor on day 35 after administration |
|---|---|---|---|
| Vehicle control | 16.8 ± 0.7 | — | — |
| Cpd. 6, 50 mg/kg | 7.5 ± 0.7*** | 44.40 | — |
| Ibrutinib 20 mg/kg | 11.4 ± 1.5 | 67.70 | — |
| Cpd. 6, 50 mg/kg + Ibrutinib, 20 mg/kg | 3.7 ± 0.4***##$ | 21.80 | 1.3 |

***P < 0.001, compared with vehicle group,
p < 0.01, compared with Compound 6 group;
$p < 0.05, compared with Ibrutinib group; synergistic factor >1, synergistic effect; synergistic factor = 1, additive effect; synergistic factor <1, antagonistic effect (3) Summary The combination of Compound 6 and Ibrutinib had no significant side effects (4B), significantly increased the anti-tumor effect of single drug in human DOHH2 (FL) mouse xenograft tumor model, and had a significant synergistic effect (synergistic factor of 1.3, more than 1). Therefore, the combination of Compound 6 and Ibrutinib may clinically benefit patients with follicular lymphoma (FL).

Example 7. Effects of Ibrutinib Alone and Combination of Ibrutinib and Compound 6 on Human OCI-LY1 Cell Line DLBCL Mouse Xenograft Tumor Model (1) The experimental method was as described in section (2) of Example 1. In the experiment, the therapeutic effect of the combination of Compound 6 and Ibrutinib in a DLBCL xenograft tumor model derived from the human OCI-LY1 cell line (same as Example 4) was evaluated.

(2) Experimental Results

Figure 5:
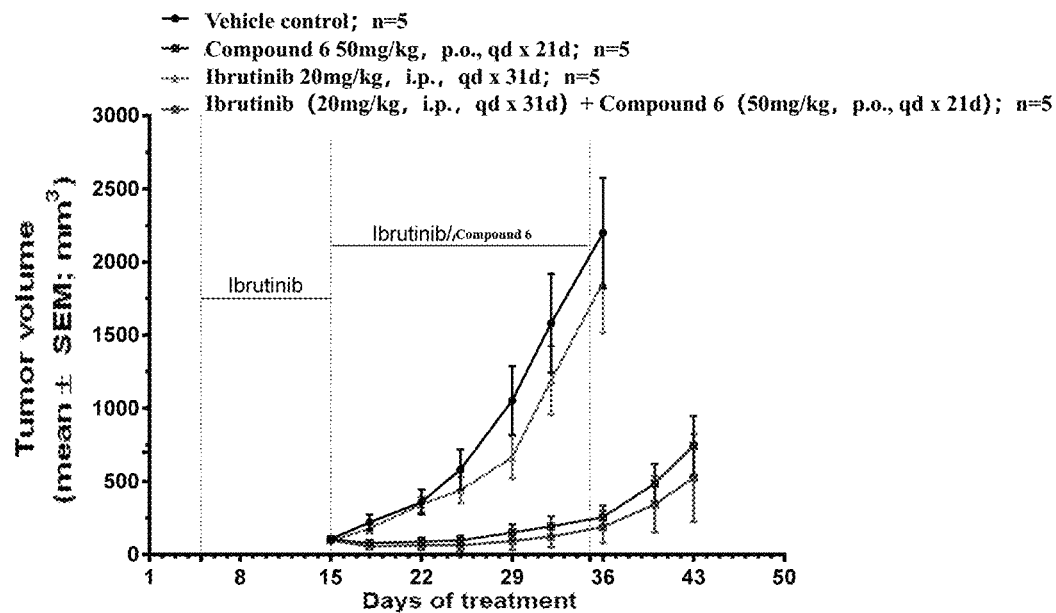
FIG. 5 shows the anti-tumor effects (A) and body weight change (B) of Compound 6 alone or in combination with Ibrutinib in a human OCI-LY1 (diffuse large B-cell lymphoma (DLBCL)) mouse xenograft tumor model.
Figure 5:
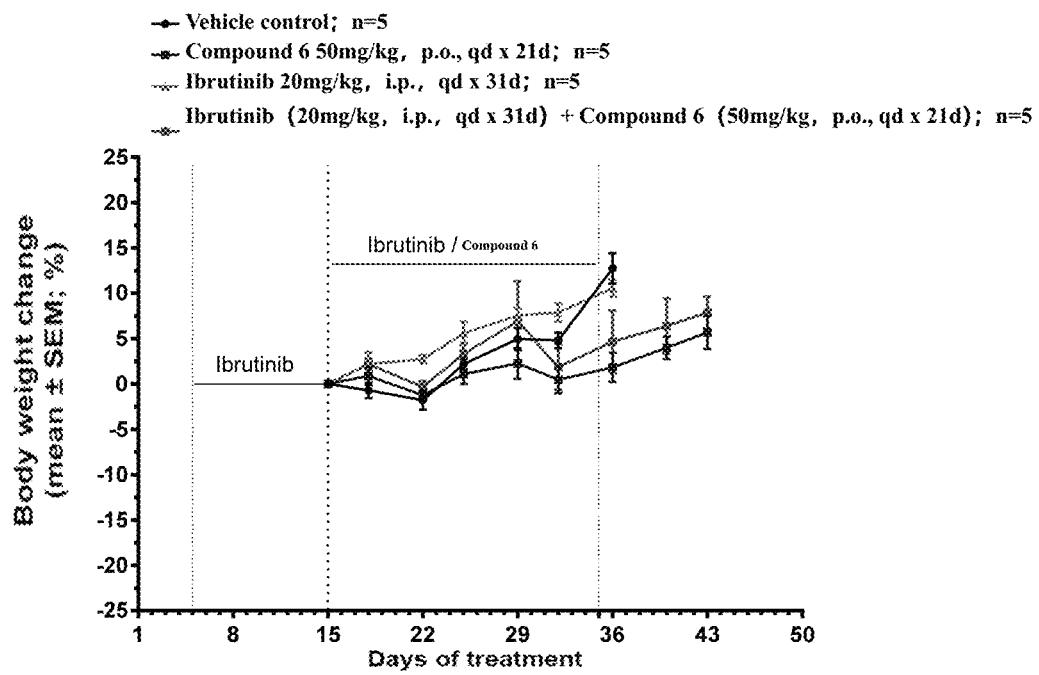

As shown in FIG. 5A and Table 6, on the 36th day after grouping, the combination group had a significant difference in RTV values relative to the Ibrutinib alone group.

TABLE 6

Anti-tumor effects of Compound 6 alone or
in combination with Ibrutinib in
human OCI-LY1 (DLBCL) mouse xenograft tumor model

| Treatment | RTV on day 36 after administration (mean ± standard error) | T/C on day 36 after administration | Synergistic factor on day 36 after administration | RTV on day 43 after administration |
|---|---|---|---|---|
| Vehicle control | 25.4 ± 5.2 | | | |
| Cpd. 6, 50 mg/kg | 2.2 ± 0.4 | 0.090 | | 7.1 ± 0.4 |
| Ibrutinib 20 mg/kg | 20.5 ± 2.1 | 0.810 | | |
| Ibrutinib 20 mg/kg + Cpd. 6 50 mg/kg | 1.4 ± 0.7%% | 0.060 | 1.26 | 4.1 ± 1.8 |

%%p < 0.01, compared with Ibrutinib 20 mg/kg (3) Summary

The combination of Compound 6 and Ibrutinib had no significant side effects (FIG. 5B), significantly increased the anti-tumor effect of single drug in the DLBCL model of OCI-LY1 cells, and had a significant synergistic effect (synergy factor was 1.26, greater than 1). Therefore, the combination of Compound 6 and Ibrutinib may clinically benefit patients with diffuse large B-cell lymphoma (DLBCL).

Example 8. The Inhibition Effect of Ibrutinib or Compound 6 Alone and Combination of Ibrutinib and Compound 6 on Cell Growth in DLBCL and Follicular Lymphoma Cells (1) Materials and Methods Reagents Ibrutinib was purchased from Selleck (China, Cat. S2680) or Aikonchem (Nanjing, China, Cat. 2645743). For in vivo studies, ibrutinib (Selleck) was formulated in 10% PEG400 (Sigma, St. Louis, Mo., Cat. 91893-1L-F), 5% Cremophor EL (Sigma, Cat. C5135-500G) and 85% PBS (GENOME, Hangzhou, China, Cat. GNM14190); whereas ibrutinib (Aikonchem) was formulated in 5% DMSO (Sigma, Cat. D8418) plus 95% (20% H-β-CD) (Seebio, Shanghai, China, Cat. ACJ0024A). For in vitro studies, ibrutinib was dissolved in DMSO to 10 mM stock solution and diluted in serum-free medium to indicated concentration. Compound 6 (R16JA450041-A5s) was synthesized by Ascentage Pharma (Suzhou, China). ABT-199 was purchased from Aikonchem (Naijing, China, Cat. 2427965). Compound 6 and ABT-199 were formulated in 10% ethanol (Sinopharma, Shanghai, China, Cat. 10009257), 30% polyethylene glycol 400 and 60% Phosal 50 PG (Lipoid GmbH, Germany, Cat. 368315-31700201006) for in vivo studies. Compound 6 used in vitro was dissolved in DMSO to 10 mM stock solution and diluted to indicated concentration with serum-free medium. Antibodies used in this study were purchased from Cell Signaling Technology (CST, China): AKT (Cat. 4685S), p-AKT (Ser473) (Cat. 4060S), BAX (Cat. 5023), Bcl-2 (Cat. 4223), BIM (Cat. 2819S), BTK (Cat. 8547S), p-BTK (Tyr223)

(Cat. 5082S), caspase-2 (Cat. 9665S), MCL-1 (Cat. 94296S), PARP-1 (Cat. 9532), β-ACTIN (Cat. 3700S).

Cell Lines

The human B cell lymphoma cell line DOHH-2 was provided by Dr. Shaomeng Wang (University of Michigan, Ann Arbor, Mich.). The human diffused large-B-cell lymphoma cell line OCI-LY1 was obtained from Dr. Dajun Yang (Sun Yat-Sen University Cancer Center, Guangdong, China). All cell lines were tested and authenticated by STR (short-tandem repeat) analysis. DOHH-2 cells were cultured in RPMI 1640 medium (GIBCO, China, Cat. C11875500BT) supplemented with 10% fetal bovine serum (GIBCO, Australia, Cat. 10099-141) and 1% Penicillin/Streptomycin (GENOME, Hangzhou, China, Cat. GNM15140). OCI-LY1 cells were cultured in IMDM (GIBCO, China, Cat. 12200036) medium containing 20% fetal bovine serum and 1% Penicillin/Streptomycin. Cells were cultured and maintained at 37° C. in a humidified incubator with 5% CO2 and 95% air.

Cell Viability Assays

Cell viability was determined by using CellTiter-Glo® luminescent cell viability assay (Promega, China) according to manufacturer's instruction. Briefly, 5000 cells were seeded in 96-well plates and treated with single agent or drug combinations for 72 h. CellTiter-Glo® reagent was added into the 96-well plates (30 μL/well) after drug treatment and incubated with cells for 15 minutes. Relative light unit (RLU) were determined by microplate reader (BioTek, Synergy H1MF, USA). Cell viability was calculated as cell viability=(mean RLU sample−mean RLU blank)/(RLU cell control−RLU blank)×100. IC50 value was calculated using GraphPad Prism. IC50 was expressed as mean±standard deviation (SD). Combination index (CI) value was calculated by CalcuSyn software (BIOSOFT, UK). In general, synergy scores>1, CI<0.9 indicate a synergistic combination effect. CI<0.1 labeled as 5+ indicates very strong synergistic combination effect, CI between 0.1 and 0.3 labeled as 4+ indicates strong synergistic combination effect, CI between 0.3 and 0.7 labeled as 3+ indicates medium synergistic combination effect.

(2) Experimental Results

High level of BCL2 expression was documented correlating with poor prognosis in B-lymphocyte neoplasm. Indeed, BCL2 is upregulated in ibrutinib-resistant cell lines and these cells are sensitive to Bcl-2 inhibitor ABT-199 and its combination with BTK inhibitor ibrutinib (Kuo et al., 2017). Compound 6 is a novel, orally bioavailable BH3-mimetic that selectively inhibits BCL-2, but not BCL-xL or MCL-1. Anti-proliferative activities of Compound 6 as a single agent is comparable if not better than ABT-199 in various hematological malignancies cell lines including those from DLBCL and FL (data not shown). Here, we evaluated whether combination treatment with Compound 6 and ibrutinib could further enhance the anti-proliferative activities in these hematological malignancies cell lines.

In the experiment, proliferation of FL (FIG. 6A) and DLBCL (FIG. 6B) cells was assessed by CellTiter-Glo® cell viability assay 72 hours after the treatments with Compound 6, ibrutinib, or the combination of both agents at indicated concentrations. Dose-response curves for cell viability (FIG. 6A left and FIG. 6B left) and drug dose matrix (FIG. 6A right and FIG. 6B right) are shown. The CI values of the combination treatment with Compound 6 and ibrutinib at indicated concentration were calculated by CalcuSyn (BIOSOFT). CI<0.9 indicates a synergistic effect of two agents. Drug dose matrix indicates percentage of growth inhibition of treated cells relative to the vehicle control group.

Figure 6:
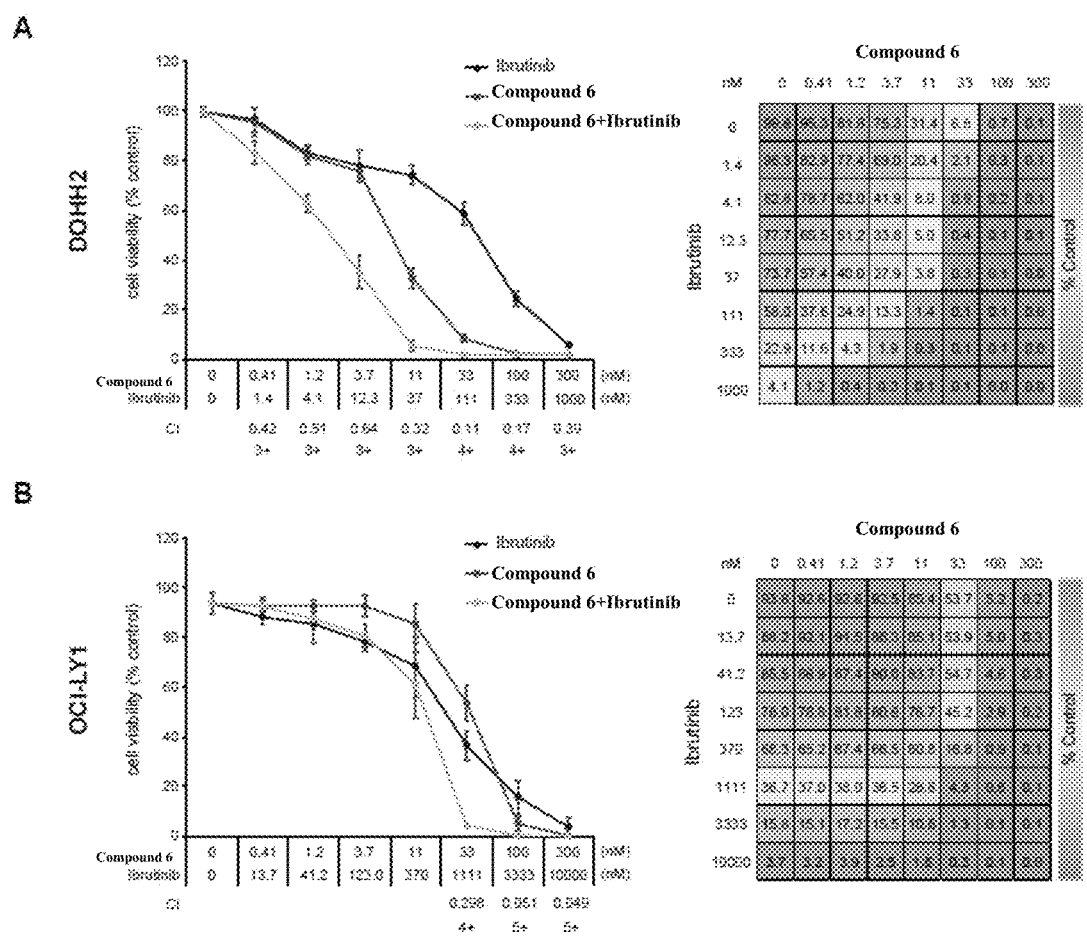
FIG. 6 shows the synergistic inhibition of proliferation of FL (follicular lymphoma, FL) and DLBCL (diffuse large B-cell lymphoma (DLBCL)) cells by combination treatment with Compound 6 and ibrutinib in vitro.

Specifically, cell viability tests from human FL DOHH-2 (FIG. 6A) and DLBCL OCI-LY1 (FIG. 6B) cells revealed that the dose response curve of Compound 6 combined with ibrutinib shifted toward left compared to single agents alone, suggesting synergistic effects. Combination index (CI) of Compound 6 and ibrutinib was calculated for different dosages of combination as indicated (FIG. 6A left and FIG. 6B left). In DOHH2 cell lines, synergy and CI was recorded from low concentration of Compound 6 (0.41 nM) and ibrutinib (1.4 nM) onwards. While in OCI-LY1 cell lines, synergy and CI was exhibited at higher concentration of Compound 6 (33 nM) and ibrutinib (1111 nM) onwards. Percentage of growth suppression for each concentration of combination in DOHH2 and OCI-LY1 was obtained and plot as drug dose matrix are shown in FIG. 6A right and FIG. 6B right. FIG. 6 shows that Ibrutinib synergizes with Compound 6 on inhibition of cell growth in DLBCL and follicular lymphoma cells.

Example 9. The Effect of Ibrutinib or Compound 6 Alone and Combination of Ibrutinib and Compound 6 on the Apoptosis of FL and DLBCL Cell Lines (1) Materials and Methods The reagents and cell lines were as described in the section (1) of Example 8.

Flow Cytometry Analysis of Cell Apoptosis

Apoptosis was evaluated with AnnexinV/propidium iodide (PI) dyes (BD Biosciences, Cat. 556547) according to manufacturer's instructions. Briefly, cells were seeded in 24-well plates at a density 2×105 cells/well, and treated with Compound 6 and/or ibrutinib (Selleck) to induce apoptosis. After 24 h, cells were collected, washed twice with PBS (pH 7.4), and stained with Annexin-V and propidium iodide (PI) for 15 mins. Stained samples were analyzed using flow cytometer Attune NxT (Life technologies).

(2) Experimental Results

Although ibrutinib is currently in routine clinical practice for treating CLL patients, apoptosis induced by ibrutinib has been documented as limited (Cinar et al., 2013; Deng et al., 2017). We hypothesized that by targeting distinct survival pathways using inhibitors of BTK and BCL may enhance rate of apoptosis and contribute to the synergistic anti-proliferation.

In the experiment, the combination treatment with Compound 6 and ibrutinib was evaluated for its ability of apoptosis induction on DOHH2 and OCI-LY1 cells by co-staining of Annexin-V/Propidium iodide (PI) followed by flow cytometry analysis (FIG. 7A). When cells were treated with ibrutinib alone, limited apoptosis activity was observed, consistent with previous reported studies (Deng et al., 2017). Compound 6 treated cells, showed slightly enhanced apoptotic activity. Notably, combined treatment of Compound 6 and ibrutinib resulted in increased cellular apoptosis with statistical significance ($p<0.001$) (FIG. 7B). Flow cytometry analysis of apoptotic cells by Annexin V and propidium iodide (PI) co-staining in DOHH-2 and OCI-LY1 cell lines treated with 10 nM (DOHH-2) or 15 nM (OCI-LY1) Compound 6, 100 nM (DOHH-2) or 150 nM (OCI-LY1) ibrutinib, or the combination for 24 hours. Three independent experiments were conducted and the representative results are shown (7A). The percentages of Annexin V-positive, PI-positive, or double positive DOHH-2 (7B) and OCI-LY1 (7C) cells are plotted as bar charts and shown as mean±SEM (n=3) ($p<0.01$, *$p<0.001$). FIG. 7 shows that the synergistic induction of apoptosis of FL and DLBCL cells by combination treatment with Compound 6 and ibrutinib in vitro.

Example 10. Synthesis of Bcl-2/Bcl-xL Dual Inhibitors

Compound 72: (R)-2-(1-(3-(4-(N-(4-(4-(3-(2-(4-chlorophenyl))-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)piperidine-4-carbonyloxy)ethylphosphonic acid. Compound 72 can be prepared by the following method, as described in the specification of WO2014/113413A1.

1H NMR (300 MHz, CD3OD):δ7.93 (d, J=1.9 Hz, 1H), 7.72 (dd, J=9.2, 1.8 Hz, 1H), 7.30-7.12 (m, 12H), 6.83-6.42 (m, 5H), 4.46-4.33 (m, 3H), 3.96 (s, 1H), 3.54-2.93 (m, 16H), 2.82 (s, 3H), 2.72 (s, 3H), 2.71-2.55 (m, 1H), 2.24-1.65 (m, 8H), 1.41 (d, J=7.1 Hz, 6H). MS (ESI): m/z 1268.58 (M+H)$^+$.

Compound 88: (R)-1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-sulfamoyl)-2-(trifluoromethyl sulfonyl)phenylamino)-4-(phenylthio)butyl)piperidine-4-carboxylic acid. Compound 88 can be prepared by the following method, as described in the specification of WO2014/113413A1.

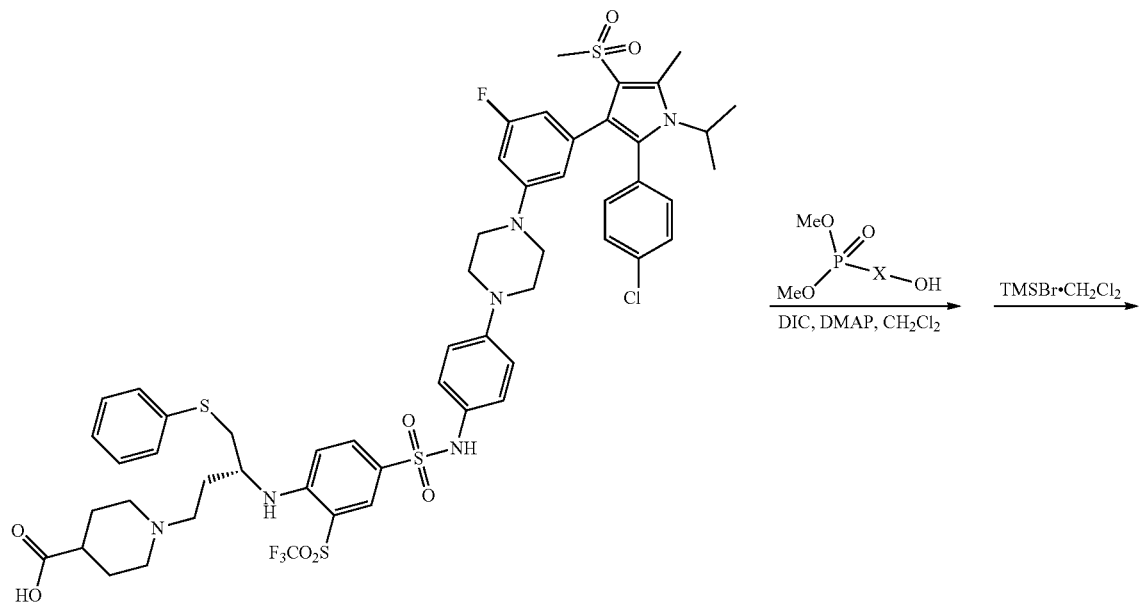

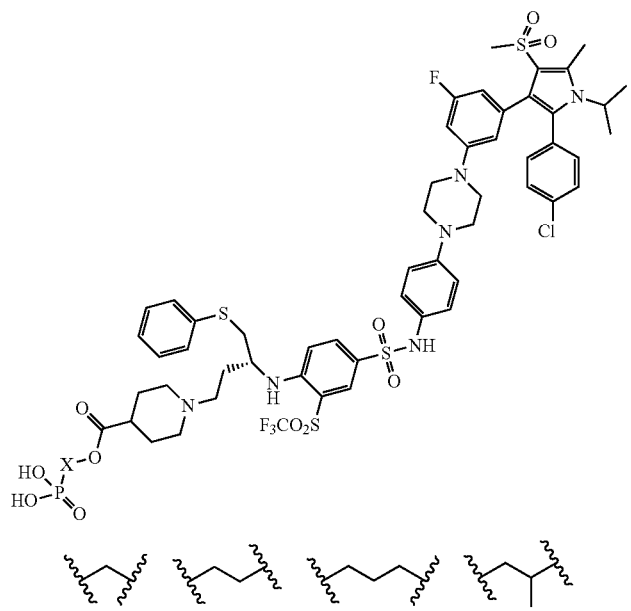

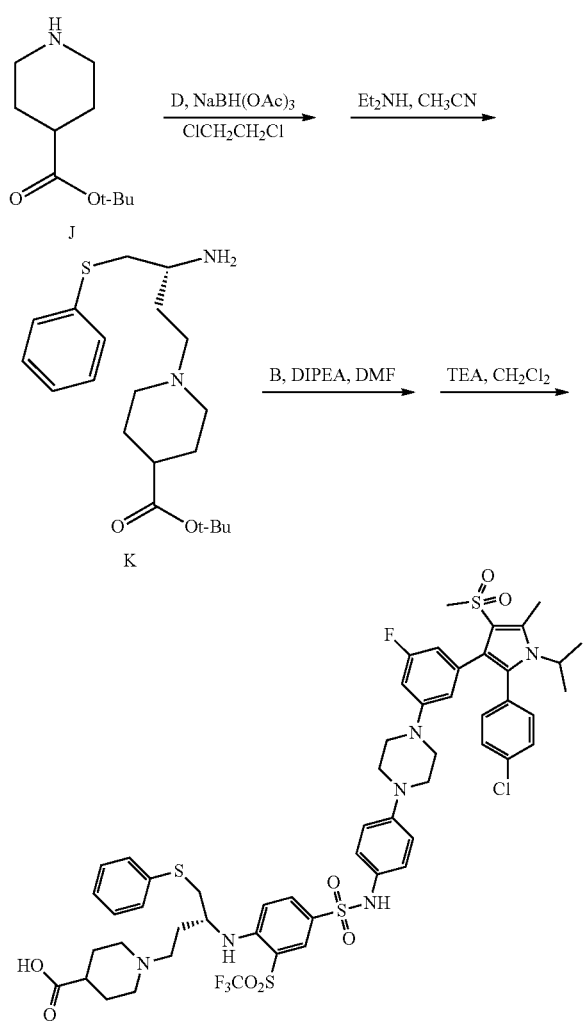

1H NMR (400 MHz, DMSO-d6) δ 9.84 (s, 1H), 7.82 (s, 1H), 7.65 (d, J=8.7 Hz, 1H), 7.38 (d, J=8.5 Hz, 2H), 7.32-7.14 (m, 7H), 7.11-6.81 (m, 6H), 6.63-6.47 (m, 2H), 6.43-6.30 (m, 1H), 4.33 (p, J=7.1 Hz, 1H), 4.07 (s, 1H), 3.32-3.22 (m, 4H), 3.19-3.03 (m, 9H), 2.89 (s, 4H), 2.67 (s, 4H), 2.31-1.55 (m, 8H), 1.35 (d, J=7.0 Hz, 6H).

Example 11. Establishment of Ibrutinib-Resistant DOHH2R Cell Line

DOHH2 is a human follicular lymphoma (FL, belonging to the NHL) cell line provided by Dr. Shaomeng Wang (University of Michigan, Ann Arbor, Mich.). DOHH2 cells were cultured in RPM11640 medium containing 10% calf serum, 1% antibiotics and 5 ug/ml verapamil (calcium ion channel blocker), and ibrutinib was added at a gradually increasing concentration from 0.5 uM to 10 uM. After exposure for about three months, a ibrutinib-resistant DOHH2R cell line was obtained, also referred to as DOHH2$^{R-ibrutinib}$. After DOHH2$^{R-ibrutinib}$ was stabilized, it was continued to be cultured in culture medium containing 10 uM Ibrutinib to maintain its resistance. Ibrutinib is absent only in the susceptibility test with Compound 6 or 88.

Cell Viability Assays

Cell viability was determined by using the CellTiter-Glo® luminescent cell viability assay (Promega, China) according to manufacturer's instruction. Briefly, 5000 DOHH2$^{R-ibrutinib}$ cells were seeded in 96-well plates and treated with test drugs for 24 or 72 hours. CellTiter-Glo reagent was added into the 96-well plates (30 μL/well) after drug treatment and incubated with the cells for 15 minutes. Relative light units (RLU) were determined by a microplate reader (BioTek, Synergy H1 MF, USA). Cell viability was calculated as cell viability=(mean RLU sample−mean RLU blank)/(RLU cell control−RLU blank)×100. IC$_{50}$ values were calculated using GraphPad Prism. IC$_{50}$ was expressed as mean±standard deviation (SD).

The cell viability assay of ibrutinib showed that the IC$_{50}$ value of ibrutinib to DOHH2 cells was 0.07352 μM, but the IC$_{50}$ value of ibrutinib to the DOHH2$^{R-ibrutinib}$ cell line was 12.19 μM, which was a 160-fold increase (FIG. 8), indicating that DOHH2$^{R-ibrutinib}$ cells were resistant to ibrutinib.

The effect of BCL-2 inhibitors on cell viability was tested in DOHH2 cells and Ibrutinib-resistant DOHH2$^{R-ibrutinib}$ cells, respectively. Two BCL-2 inhibitors, Compound 6 and ABT-199, were compared. The results showed (FIG. 9) that both Compound 6 and ABT-199 were both effective in inhibiting the growth of DOHH2 cells and showed similar IC$_{50}$ values (0.0484 μM for Compound 6, and 0.0511 μM for ABT-199), but Compound 6 showed significantly higher inhibitory effect on the growth of DOHH2$^{R-ibrutinib}$ cells than ABT-199, indicating that Compound 6 can better overcome the resistance of the DOHH2$^{R-ibrutinib}$ cell line to ibrutinib. The IC$_{50}$ value of Compound 6 to the DOHH2$^{R-ibrutinib}$ cell line was 0.648 μM, while the IC$_{50}$ value of ABT-199 to the DOHH2$^{R-ibrutinib}$ cell line was 1.189 μM, which was significantly inferior to the effect of Compound 6.

The effect of BCL-2/BCL-xL dual inhibitor Compound 88 on cell viability was further tested in DOHH2 cells and ibrutinib-resistant DOHH2$^{R-ibrutinib}$ cells, respectively. The results showed that Compound 88 potently inhibited the growth of ibrutinib-resistant DOHH2$^{R-ibrutinib}$ cells with an IC$_{50}$ value of 0.017 μM, and led to cell death within 24 hours.

What is claimed is:

1. A combination comprising
   a) a Bcl-2 inhibitor;

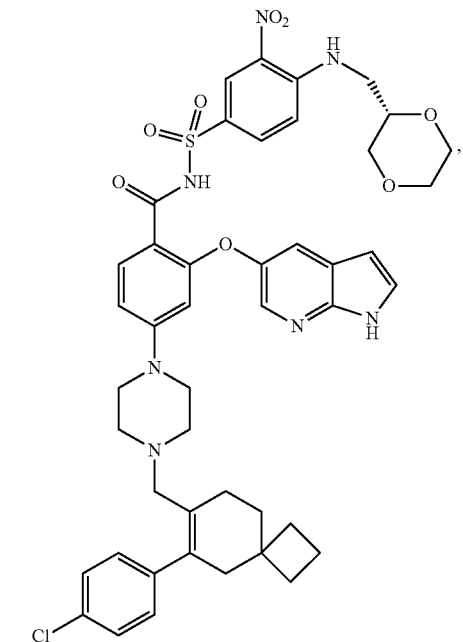 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt, thereof; and
   b) a BTK inhibitor; Ibrutinib.

2. The combination according to claim 1, wherein the combination product is in the form of a pharmaceutical composition.

3. The combination according to claim 1, wherein the Bcl-2 inhibitor and the BTK inhibitor are each in a separate preparation.

4. The combination according to claim 1, wherein the Bcl-2 inhibitor and the BTK inhibitor are administered simultaneously or sequentially.

5. The combination according to claim 1, further comprising a pharmaceutically acceptable carrier, diluent, or excipient.

6. The combination according to claim 1, further comprising a tablet, a capsule, a granule, a syrup, a powder, a lozenge, a sachet, a cachet, an elixir, a suspension, a emulsion, a solution, a syrup, an aerosol, an ointment, a cream, or an injection.

7. A method of treating a disease, comprising administering to a subject in need thereof a prophylactically and/or therapeutically effective amount of:
  a) a Bcl-2 inhibitor;

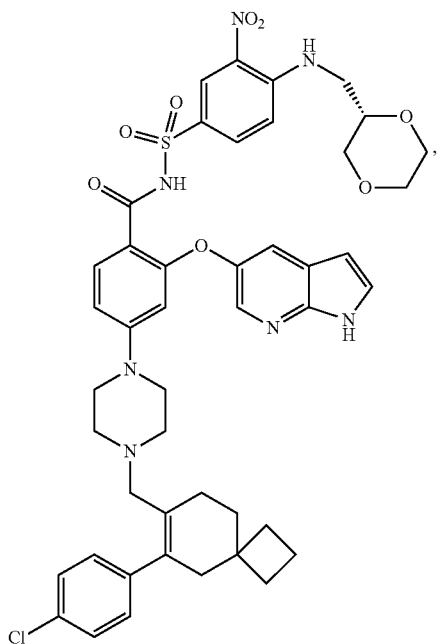 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt or solvate, thereof; and b) a BTK inhibitor; Ibrutinib or a pharmaceutically acceptable salt or solvate thereof, wherein the disease is selected from the group consisting of cancer, autoimmune disease, and inflammatory disease.

8. The method of claim 7, wherein the cancer is selected from the group consisting of acute myeloid leukemia (AML), acute lymphoblastic leukemia (ALL), diffuse large B-cell lymphoma (DLBCL), follicular lymphoma (FL), chronic lymphocytic leukemia (CLL)/small lymphocytic lymphoma (SLL), marginal zone lymphoma (MZL), chronic myelogenous leukemia (CML), mantle cell lymphoma (MCL), Waldenstrom's macroglobulinemia (WM), multiple myeloma (MM), and small cell lung cancer (SCLC).

9. The method according to claim 7, wherein the Bcl-2 inhibitor, or the pharmaceutically acceptable salt or solvate thereof is administered in an amount of from about 0.0025 to 1500 mg/day.

10. The method according to claim 7, wherein the BTK inhibitor or pharmaceutically acceptable salt or solvate thereof is administered in an amount of from about 0.0025 to 1000 mg per day.

11. The method according to claim 7, wherein the subject is refractory or is resistant to treatment with a BTK inhibitor.

* * * * *